(12) United States Patent
Baird et al.

(10) Patent No.: US 6,472,537 B1
(45) Date of Patent: Oct. 29, 2002

(54) POLYAMIDES FOR BINDING IN THE MINOR GROOVE OF DOUBLE STRANDED DNA

(75) Inventors: Eldon E. Baird, Foster City, CA (US); Peter B. Dervan, San Marino, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 09/372,473

(22) Filed: Aug. 11, 1999

Related U.S. Application Data

(63) Continuation-in-part of application No. PCT/US97/12722, filed on Jul. 21, 1997, and a continuation-in-part of application No. PCT/US97/03332, filed on Feb. 20, 1997, and a continuation-in-part of application No. 08/853,522, filed on May 8, 1997, now abandoned, and a continuation-in-part of application No. 08/837,524, filed on Apr. 21, 1997, now Pat. No. 6,143,901, and a continuation-in-part of application No. 08/607,078, filed on Feb. 26, 1996, now Pat. No. 6,090,947.

(60) Provisional application No. 60/042,022, filed on Apr. 6, 1997, provisional application No. 60/043,444, filed on Apr. 8, 1997, provisional application No. 60/038,384, filed on Feb. 14, 1997, provisional application No. 60/026,713, filed on Sep. 25, 1996, provisional application No. 60/024,374, filed on Aug. 1, 1996, and provisional application No. 60/023,309, filed on Jul. 31, 1996.

(30) Foreign Application Priority Data

Jan. 28, 1998 (WO) ................................ PCT/US98/01006

(51) Int. Cl.$^7$ .................... C07D 231/02; C07D 403/02; C07D 233/04; C07N 19/00; C07N 21/02
(52) U.S. Cl. ................. 548/312.2; 548/312.4; 548/312.7; 548/313.1; 548/314.7; 548/334.5; 548/557
(58) Field of Search ........................ 548/312.2, 313.1; 536/22.1, 23.1

(56) References Cited

U.S. PATENT DOCUMENTS

| | | | |
|---|---|---|---|
| 4,795,700 A | 1/1989 | Dervan et al. .................. 435/5 |
| 5,539,083 A | 7/1996 | Cook et al. .................. 530/333 |
| 5,563,250 A | 10/1996 | Hylarides et al. | |
| 5,578,444 A | 11/1996 | Edwards et al. ................ 435/6 |
| 5,693,463 A | 12/1997 | Edwards et al. ................ 435/6 |
| 5,698,674 A | 12/1997 | Bruice et al. | |
| 5,726,014 A | 3/1998 | Edwards et al. ................ 435/6 |
| 5,738,990 A | 4/1998 | Edwards et al. ................ 435/6 |
| 5,801,155 A | 9/1998 | Kutyavin et al. | |
| 6,143,901 A | * 11/2000 | Dervan .................... 548/312.4 |

FOREIGN PATENT DOCUMENTS

| | | |
|---|---|---|
| CA | 2 005 039 | 6/1991 |
| DE | 43 31 012 A1 | 3/1995 |
| EP | 0 246 868 A1 | 11/1987 |
| EP | 0 388 948 A1 | 9/1990 |
| GB | 2 261 661 A | 5/1993 |
| WO | 92/09574 | 6/1992 |
| WO | 92/13838 | 8/1992 |
| WO | 92/14707 | 9/1992 |
| WO | 93/00446 | 1/1993 |
| WO | 94/03434 | 2/1994 |
| WO | 94/14980 | 7/1994 |
| WO | 94/20463 | 9/1994 |
| WO | 94/25436 | 11/1994 |
| WO | 95/04732 | 2/1995 |
| WO | 96/05196 | 2/1996 |
| WO | 96/32496 | 10/1996 |
| WO | 97/03957 | 2/1997 |
| WO | 97/2812 | 8/1997 |

OTHER PUBLICATIONS

Chen et al, Structural Biology, vol. 1, No. 3, pp. 169–175, Mar., 1994.*

Howard et al., Biochem. Biophys. Research Comms, vol. 17, No. 1, pp. 93–102, 1964.*

Kissinger ER et al., Biochemistry, vol. 26, pp 5590 to 5595, 1987.*

Kopka et al I, J. Mol. Biol., vol. 183, pp 553 to 563, 1985.*

Kopka et al II, Proc. Natl. Acad. Sci, USA, vol. 82, pp. 1376 to 1380, 1985.*

Krugh, Current Opinion In Structural Biology, vol. 4, pp. 351 to 364, 1994.*

Lee et al, Biochemistry, vol. 32, pp 4237 to 4245, 1993.*

Pelton et al, Proc. Natl. Acad. Sci USA, vol. 86, pp. 5723 to 5727, 1989.*

Abu–Daya et al., "DNA sequence preferences of several AT–selective minor groove binding ligands," *Nucleic Acids Research* 23:3385–3392 (1995).

Abu–Daya et al., "Interaction of minor groove binding ligands with long AT tracts," *Nucleic Acids Research* 25:4962–4969 (1997).

Ades et al., "Specificity of minor–groove interaction in a homeodomain–DNA complex," *Biochemistry* 34:14601–14608 (1995).

Al Said et al., "Synthesis of novel cross–linked bis–lexitropsins," *Tet. Lett.* 35:7577–7580 (1994).

(List continued on next page.)

*Primary Examiner*—Deborah C. Lambkin
(74) *Attorney, Agent, or Firm*—Foley & Lardner

(57) ABSTRACT

The invention encompasses improved polyamides for binding to specific nucleotide sequences in the minor groove of double stranded DNA. The 3-hydroxy-N-methylpyrrole/N-methylpyrrole carboxamide pair specifically recognizes the T·A base pair, while the N-methylpyrrole/3-hydroxy-N-methylpyrrole pair recognizes A·T nucleotide pairs. Similarly, an N-methylimidizole/N-methylpyrrole carboxamide pair specifically recognizes the G·C nucleotide pair, and the N-methylpyrrole/N-methylimidizole carboxamide pair recognizes the C·G nucleotide pair.

17 Claims, 18 Drawing Sheets

OTHER PUBLICATIONS

Aleman et al., "Toward an Understanding of the Drug–DNA Recognition Mechanism. Hydrogen–Bond Strength in Netropsin–DNA Complexes," *J. Phys. Chem.* 100:11480–11487 (1996).

Al–Said et al., "A convenient synthesis of cross–linked homodimeric bis–lexitropsins," *Synth. Commun.* 25(7):1059–1070 (1995).

Al–Said et al., "Synthesis of novel cross–linked bis–lexitropsins," *Tetrahedron Lett.* 35(41):7577–7580 (1994).

Adronikashvili et al., "Spectral Manifestations of the Action of $Zn^{2+}$ Ions on DNA Complexes with Distamycin," *Biophysics* 33:824–829 (1988).

Arcamone et al., "Distamicina A. Nota I. Isolamento e struttura dell'agente antivirale distamicina A," pp. 1097–1109 (In Spanish with English Abstract).

Arcamone et al., "Structure and synthesis of Distamycin A," *Nature* 203:1064–1065 (1964).

Arcamone et al., "Synthesis, DNA binding and antiviral activity of distamycin analogues containing different heterocyclic moieties," *Anti–Cancer Drug Design* 1:235–244 (1986).

Bailly et al., "Depsipeptide Analogs of the Antitumor Drug Distamycin Containing Thiazole Amino Acids Residues," *Tetrahedron* 44:5833–5843 (1988).

Bailly et al., "Design, Synthesis, DNA Binding, and Biological Activity of a Series of DNA Minor–Groove–Binding Intercalating Drugs," *Journal of Pharmaceutical Sciences* 78:910–917 (1989).

Bailly et al., "Subcellular Distribution of a Nitroxide Spin–Labeled Netropsin in Living KB Cells," *Biochemical Pharmacology*, 38:1625–1630 (1989).

Baird and Dervan, "Solid Phase Synthesis of Polyamides Containing Imidazole and Pyrrole Amino Acids," *J. Am. Chem. Soc.* 118:6141–6146 (1996).

Baird et al., "Solid phase synthesis of polyamides containing imidazole and pyrrole amino acids," *J. Am. Chem. Soc.* 118:6141–6146 (1996).

Baker and Dervan, "70. Sequence Specific Cleavage of Double Helical DNA. N–Bromoacetyldistamycin" (Abstract).

Baker and Dervan, "Sequence–Specific Cleavage of DNA by N–Bromoacetyldistamycin. Product and Kinetic Analyses," *J. Am. Chem. Soc.* 111:2700–2712 (1989).

Baker and Dervan, "Sequence–Specific Cleavage of Double–Helix DNA. N–Bromoacetyldistamycin," *J. Am. Chem. Soc.* 107:8266–8268 (1985).

Baliga et al., "RecA–oligonucleotide filaments bind in the minor groove of double–stranded DNA," *Proc. Natl. Acad. Sci. USA* 92:10393–10397 (1995).

Beal and Dervan, "Recognition of Double Helical DNA by Alternate Strand Triple Helix Formation," *J. Am. Chem. Soc.* 114:4976–4982 (1992).

Best and Dervan, "Energetics of Formation of Sixteen Triple Helical Complexes Which Vary at a Single Position within a Pyrimidine Motif," *J. Am. Chem Soc.* 117:1187–1193 (1995).

Bianchi et al., "Alteration of the Expression of Human Estrogen Receptor Gene by Distamycin," *J. Steroid Biochem. Molec. Biol.* 54:211–215 (1995).

Borodulin et al., "Interaction of Ligand of the bis–Netropsin Type with Poly(dA)•Poly(dT). Optical, Structural, and Energetic Characteristics of AT–Specific Binding," *Institute of Molecular Biology,* Academy of Sciences of USSR, pp. 929–934 (1987) translated from *Molekulyarnaya Biologiya* 20(4):1144–1149 (1986).

Borodulin et al., "New Modes of Ligand Interaction with DNA: A Trimeric bis–Netropsin Complex with Poly-(dA–dT)," *Molecular Biology* 30:661–665 (1996).

Botella and Nieto, "The C–terminal DNA–binding domain of Chironomus BR gene products shows preferentially affinity for (dA•dT)–rich sequences," *Mol Gen Genet* 251:422–427 (1996).

Brabec and Balcarova, "459—The Effect of Netropsin on the Electrochemical Oxidation of DNA at a Graphite Electrode," *Biotechnology & Bioenergetics* 9:245–252 (1982).

Braun et al., "Stereoselective Aldol Reactions with (R)– and (S)–2–Hydroxy–1,2,2–triphyenylethyl Acetate ("HYTRA") " (Abstract).

Breslauer et al., "The origins of the DNA binding affinity and specificity of minor groove directed ligands: Correlations of thermodynamic and structural data," Structure & Expression 2:273–289 (1988).

Broeker et al., "The Mixed Lineage Leukemia (MLL) Protein Involved in 11q23 Translocations Contains a Domain that Binds Cruciform DNA and Scaffold Attachment Region (SAR) DNA," pp. 259–268.

Broggini et al., "Modulations of transcription factor–DNA interactions by anticancer drugs," *Anti–Cancer Drug Design* 9:373–387 (1994).

Bruice et al., "A microgonotropen branched decaaza decabutylamine and its DNA and DNA/transcription factor interactions," Bioorg. Med. Chem. 5:685–692 (1997).

Bruice et al., "Rational design of tripyrrole peptides that complex with DNA by both selective minor–groove binding and electrostatic interaction with the phosphate backbone," Proc. Natl. Acad. Sci. USA 89:1700–1704.

Bruzik et al., "Specific Activation of Transcription Initiation by the Sequence–Specific DNA–Binding Agents Distamycin A and Netropsin," *Biochemistry* 26:950–956 (1987).

Burckhardt et al., "Reversal of the Z– to B–Conformation of Poly(dA–dT)•Poly(dA–dT) Induced dby Netropsin and Distamycin A," *Journal of Biomolecular Structure & Dynamics* 12:671–676 (1996).

Burckhardt et al., "Two Binding Modes of Netropsin are Involved in the Complex Formation with Poly(dA–dT)•Poly(dA–dT) and other Alternating DNA Duplex Polymers," *Journal of Biomolecular Structure and Dynamics* 2:721–736 (1985).

Burridge et al., "Electrostatic potential and binding of drugs to the minor groove of DNA," 5(3):165–166 (Sep. 1987).

Cartwright et al., "Cleavage of chromatin with methidiumpropyl–EDTA•iron(II)," *Proc. Natl. Acad. Sci. USA* 80:3213–3217 (1983).

Chai and Alonso, "Distamycin–induced inhibition of formation of a nucleoprotein complex between the terminase small subunit of G1P and the non–encapsulated end (pacL site) of *Bacillus subtilis* bacteriophage SPP1," *Nucleic Acids Research* 24:282–288 (1996).

Chaloupka and Kucerova, "Netropsin increases formation of mRNA coding for a neutral metalloproteinase in *Bacillus megaterium,*" *J. Basic Microbiol.* 28:11–16 (1988).

Chandra et al., "Some Structural Requirements for the Antibiotic Action of Distamycins," *FEBS Letters* 16:249–252 (1971).

Chang et al., "On the importance of van der Walls interaction in the groove binding of DNA with ligands: restrained molecular dynamics study," International Journal of Biological Macromolecules 19:279–285 (1996).

Chen et al., "Design of Distamicin Analogues to Probe the Physical Origin of the Antiparallel Side by Side Oligopeptide Binding Motif in DNA Minor Groove Recognition," *Biochemical and Biophysical Research Communications* 220:213–218 (1996).

Chen et al., "Only one of the two DNA–bound orientations of AP–1 found in solution cooperates with NFATp," *Current Biology* 5:882–889 (1995).

Chen et al., "Optimization of Cross–Linked Lexitropsins," *Journal of Biomolecular Structure & Dynamics* 14:341–355 (1996).

Chen et al., "A new DNA minor groove binding motif: Cross–linked lexitropsins," *J. Am. Chem. Soc.* 116(16):6995–7005 (1994).

Chen et al., "Binding of 1 distamycin–A molecules in the minor groove of an alternating B–DNA duplex," Nature Struct. Biol. 1:169–175 (1994).

Chen et al., "Crystal structure of the side by side binding of distamycin to AT–containing DNA octamers d(ICITACIC)," J. Mol. Biol. 267:1157–1170 (1997).

Chen et al., "Design and synthesis of sequence–specific DNA minor groove recognizing ligands of the cross–linked lexitropsin class," *Heterocycles* 41(8):1691–1707 (1995).

Chen et al., "DNA minor groove binding of cross–linked lexitropsins: Experimental conditions required to observe the covalently linked WPPW (Groove wall peptide–peptide–groove wall)motif," *Biophy. J.* 68(5):2041–2048 (1995).

Chen, "Design, synthesis and evaluation of novel bismustard cross–linked lexitropsins," *Bioorg. Med. Chem. Lett.* 5(19):2223–2228 (1995).

Chiang et al., "Effect of DNA–binding Drugs on Early Growth Response Factor–I and TATA Box–binding Protein Complex Formation with the Herpes Simplex Virus Latency Promoter," *J. Biol. Chem.* 271:23999–24004 (1996).

Chiang et al., "Targeting E2F1–DNA complexes with microgonotropen DNA binding agents," Proc. Natl. Acad. USA 94:2811–2816 (1997).

Cho et al., "Cyclic polyamides for recognition in the minor groove of DNA," *Proc. Natl. Acad. Sci. USA* 92:10389–10392 (1995).

Church et al., Biochemistry 29:6827–2838 (1990).

Colocci and Dervan, "Cooperative Binding of 8–mer Oligonucleotides Containing 5–(1–Propynyl)–2'–deoxyuridine to Adjacent DNA Sites by Triple–Helix Formation," *J. Am. Chem. Soc.* 116:785–786 (1994).

Colocci and Dervan, "Cooperative Triple–Helix Formation of Adjacent DNA Sites: Sequence Composition Dependence at the Junction," *J. Am. Chem. Soc.* 117:4781–4787 (1995).

Colocci et al., "Cooperative Oligonucleotide–Directed Triple Helix Formation at Adjacent DNA Sites," *J. Am. Chem.Soc.* 115:4468–4473 (1993).

Colson et al., "Electric linear dichroism as a new tool to study sequence preference in drug binding to DNA," *Biophysical Chemistry* 58:125–140 (1996).

Dale et al., J. Am. Chem. Soc. 95:512–519 (1973).

Dasgupta et al., "DNA–Binding Characteristics of a Synthetic Analogue of Distamycin," *Biochemical and Biophysical Research Communications* 140:626–631 (1986).

Dasgupta et al., "Interaction of Synthetic Analogues of Distamycin with Poly(dA–dT): Role of the Conjugated N–Methylpyrrole System," *Biochemistry* 26:6381–6386 (1987).

de Clairac et al.,"NMR characterization of hairpin polyamide complexes with the minor groove of DNA," J. Am. Chem. Soc. 119:7909–7916 (1997).

Debart et al., "Synthesis, DNA Binding, and Biological Evaluation of Synthetic Precursors and Novel Analogues of Netropsin," *J. Med. Chem.* 32:1074–1083 (1989).

Dervan and Baker, "Design of Sequence–Specific DNA Cleaving Molecules," *Annals of the New York Academy of Sciences* pp. 51–59.

Dervan, "113. A Chemical Approach to the Single Site Cleavage of Human Chromosomes," *Abstracts, Division of Biological Chemistry* 31:2209 (1992).

Dervan, "117. A Chemical Approach to the Single Site Cleavage of Human Chromosomes" (Abstracts).

Dervan, "122. Design of Sequence Specific DNA Binding Molecules" (Abstract).

Dervan, "7. Design of Sequence Specific DNA Cleaving Molecules" (Abstract).

Dervan, "83. Design of Sequence Specific DNA Cleaving Molecules" (Abstract).

Dervan, "83. Synthetic Sequence Specific DNA Binding Molecules," *Abstracts, Division of Biological Chemistry* 26:4171 (1987).

Dervan, "Design of Sequence–Specific DNA–Binding Molecules," *Science* 232:464–471 (1986).

Dervan, "Reagents for the site–specific cleavage of megabase DNA," *Nature* 359:87–88 (1992).

Di Marco et al., "Experimental Studies on Distamycin A—A New Antibiotic with Cytotoxic Activity," *Cancer Chemotherapy Reports* 18:15–19 (1962).

Di Marco et al., "Selective Inhibition of the Multiplication of Phage T1 in *E. coli* K12," *Experientia* 19:134–136 (1963).

Di Marco et al., "The Antimitotic Activity of Antibiotic Distamycin A," pp. 423–426.

Di Pietro et al., "N–Formimidoyl analogues of distamycin," *J. Chem. Soc., Perkin Trans. 1*, pp. 1333–1335 (1996).

D'Incalci et al., "Studies on the Mode of Action of FCE 24517, a New Distamycin A Derivative," *Proceedings of AACR* 29:329 at abstract No. 1310 (1988).

Ding et al., "Synthesis and antiviral activity of three pyrazole analogues of distamycin A," Acta Chemica Scandinavica 48:498–505 (1994).

Ding et al., "The preparation of partially protected 3–amino–1–methylpyrazole–5–carboxylic acids to be used as intermediates in the synthesis of analogs of distamycin–A," Acta Chemica Scandivavica 44(1):75–81 (1990).

Distefano and Dervan, "Energetics of cooperative binding olgionucleotides with discrete dimerization domains to DNA by triple helix formation," Proc. Natl. Acad. Sci. USA 90:1179–1183 (1993).

Distefano and Dervan, "Ligand–Promoted Dimerization of Oligonucleotides Binding Cooperatively to DNA," *J. Am. Chem. Soc.* 114:11006–11007 (1992).

Dorn et al., "Dystamycin–induced inhibitor of homeodomain DNA complexes," EMBO Journal 11:279–286 (1992).

Dreyer and Dervan, "Sequence–specific cleavage of single–stranded DNA: Oligonucleotide–EDTA•Fe(II)," *Proc. Natl. Acad. Sci. USA* 82:968–972 (1985).

Dunner et al., "Enhancement of a Fra(16)(q22) with Distamycin A: A Family Ascertained Through an Abnormal Proposita," *American Journal of Medical Genetics* 16:277–284 (1983).

Durand and Maurizot, "Distamycin A Complexation with a Nucleic Acid Triple Helix," *Biochemistry* 35:9133–9139 (1986).

Duval–Valentin et al., "Specific–inhibition of transcription by triple–helix forming oligonucleotides," Proc. Natl. Acad. Sci. USA 89:504–508 (1992).

Dwyer et al., "Structural Analysis of Covalent Peptide Dimers, Bis(pyridine–2–carboxamidonetropsin)$(CH_2)_{3-6}$, in Complex with 5'TGACT-3' Sites by Two–Dimensional NMR", *J. Am. Chem. Soc.* 115:9900–9906 (1993).

Dwyer et al., J. Am. Chem. Soc. 114:5911–5919 (1992).

Eliadis et al., "The Synthesis and DNA Footprinting of Acridine–linked Netropsin and Distamycin Bifunctional Mixed Ligands," *J. Chem. Soc. Chem. Commun.* 1049–1052 (1988).

Feng et al., "Crystallization and preliminary X–ray analysis of the DNA binding domain of the Hin recombinase with its DNA binding site," J. Mol. Biol. 232:982–986 (1993).

Fesen and Pommier, "Topoisomerase Inhibition by Anticancer Drugs is Antagonized by Distamycin," *Proceedings of AACR* 29:276 at abstract No. 1095 (1988).

Filipowsky et al., "Linked lexitropsins and the in vitro inhibition of HIV–1 reverse transcriptase RNA–directed DNA polymerization: A novel induced–fit 3,5 m–pyridyl bisdistamycin to enzyme–associated template primer," Biochemistry 35(48)15397–15410 (1996).

Fish et al., "Determination of Equilibrium Binding Affinity of Distamycin and Netropsin to the Synthetic Deoxyoligonucleotide Sequence d(GGTATACC)$_2$ by Quantitative DNase 1 Footprinting," *Biochemistry* 27:6026–6032 (1988).

Fox and Waring, "DNA structural variations produced by actinomycin and distamycin as revealed by DNAse I footprinting," *Nucleic Acids Research* 12:9271–9285 (1984).

Fransson et al., "High–performance liquid chromatography of distamycin A and its primary decomposition products as well as some synthetic analogues," *Journal of Chromatography* 268:347–351 (1983).

Fregeau et al., "Characterization of a CPI–lexitropsin conjugate–oligonucleotide covalent complex by 1H NMR and restrained molecular dynamics simulations," J. Am. Chem. Soc. 117(35):8917–8925.

Frigero et al., "Determination of FCE 26644, a new polysulphonated derivative of distamycin A, in monkey plasma by reversed–phase ion–pair high–performance liquid chromatography with ultraviolet detection," *Journal of Chromatography A* 729:237–242 (1996).

Gao et al., "Comparative NMR Studies of Oligo–N–Methylpyrrolecarboxamide d[CGAAATTTCG] Complexes" (Abstract).

Gartenberg et al., "DNA–sequence determinants of CAP–induced bending and protein–binding affinity," Nature 333:824–829 (1988).

Geierstanger et al., "Design of a G•C–Specific DNA Minor Groove–Binding Peptide," *Science* 266:646–650 (1994).

Geierstanger et al., "Extending the recognition site of designed minor groove binding molecules," *Nature Structural Biology* 3:321–324 (1996).

Geierstanger et al., "Structural and Dynamic Characterization of the Heterodimeric and Homodimeric Complexes of Distamycin and 1–Methylimidazole–2–carboxamide–Netropsin Bound to the Minor Groove of DNA," *Biochemistry* 33:3055–3062 (1994).

Geierstanger et al., *J. Am. Chem. Soc.* 115:4474–4483 (1993).

Geierstanger, Bernard Hubert,, PhD Thesis entitled *NMR Studies of Peptides, Distamycin and its Analogs Bound to the Minor Groove of DNA,* University of California, Berkeley (1994).

Genelabs, PCR Newswire—"Genelabs Receives Seven Patent Allowances for its DNA–Binding Technology" (1987—exact date unknown).

Germann et al., "Relative Stability of Parallel– and Antiparallel–Stranded Duplex DNA," *Biochemistry* 27:8302–8306 (1988).

Giuliani et al., "Distamycin A derivatives: in vitro and in vivo activity of a new class of antitumor agents," *Proceedings of AACR* 29:330 at abstract No. 1311 (1988).

Goodsell et al., "Structure of dicationic monoimidazole lexitropsin bound to DNA," *Biochemistry* 34(51):16654–16661 (1995).

Gottesfeld et al., "Regulation of gene expression by small molecules," Nature 387:202–205 (1997).

Greenberg et al., "Energetics of Formation of Sixteen Triple Helical Complexes Which Vary at a Single Position within a Purine Motif," *J. Am. Chem. Soc.* 117:5016–5022 (1995).

Grehn et al. "Synthesis and Antiviral Activity of Distamycin A Analogues: Substitutions on the Different Pyrrole Nitrogens and the Amidine Function," *J. Med. Chem.* 26:1042–1049 (1983).

Grehn et al., "A convenient method for the preparation of 1% Tert–butyloxycarbonyl <Pyrroles," Angewandte Chemie International Edition in English v23(4)296 (1984).

Grehn et al., "Novel efficient total synthesis of antiviral antibiotic distamycin A," *Journal of Organic Chemistry* 46:3492–3497 (1981).

Grehn et al., "Removal of formyl, acetyl, and benzoyl groups from amides with conversion into the corresponding tert–butyl carbamates," Journal of the Chemical Society Chemical Communications 19(2):1317–1318 (1985).

Grehn et al., "Structure–activity–relationships in distamycin–A analogs—effect of alkyl groups on the pyrrole nitrogen at the non–amidine end of the molecule combined with methylelimination in the following ring," Acta Chemica Scandivavica 40(2):145–151 (1986).

Grehn et al., "The preparation and properties of partially protected 4–amino–1–methylimidazole–2–carboxylic acids to be used as intermediates in the synthesis of analogs of dystamycin–A," *Acta Chemica Scandivavica* 44(1):67–74 (1990).

Griffin and Dervan, "207. Sequence Specific Recognition of DNA by Chiral (Bis(Netropsin)s" (Abstract).

Griffin and Dervan, "98. Designed, Synthetic, Metalloregulatory DNA Binding Molecules" (Abstract).

Griffin and Dervan, "Recognition of Thymine–Adenine Base Pairs by Guanine in a Pyrimidine Triple Helix Motif," *Science* 245:967–971 (1989).

Griffin and Dervan, "Sequence–Specific Chiral Recognition of Right–Handed Double–Helical DNA by (2S,3S)– and (2R,3R)–Dihydroxybis(netropsin)succinamide," *J. Am. Soc. Chem.* 108:5008–5009 (1986).

Griffin, Dreyer and Dervan, "68. Sequence Specific Cleavage of Single Stranded DNA: Oligodeoxynucleotide–EDTA–FE(II)" (Abstract).

Griffin, John Hampton, PhD Thesis entitled *Structure–, Stereochemistry–, and Metal–Regulated DNA Binding/Cleaving Molecules,* California Institute of Technology, Pasadena, California (Submitted Jul. 11, 1989).

Grygon and Spiro, "Ultraviolet Resonance Raman Spectroscopy of Distamycin Complexes with Poly(dA)–(dT) and Poly(dA–dT): Role of H–Bonding," *Biochemistry* 28:4397–4402 (1989).

Guo et al., "DNA sequence–selective binding of head–to–tail linked bis–lexitropsins: relation of phasing to dytotoxic potency," *Anti–Cancer Drug Des.* 8(5):369–397 (1993).

Gupta et al., "Design, synthesis and topoisomerase II inhibition activity of 4'–demethylepipodo–phyllotoxin– lexitropsin conjugates," *Anti–Cancer Drug Design* 11:325–338 (1996).

Gupta et al., "Hybrid molecules containing propargylic sulfones and DNA minor groove–binding lexitropsins: Synthesis, sequences specificity of reaction with DNA and biological evaluation," *Gene* 149(1):81–90 (1994).

Gupta et al., "Novel DNA–directed alkylating agents consisting of naphthalimide, nitrogen mustard and lexitropsin moieties: synthesis, DNA sequence specificity and biological evaluation," *Anti–Cancer Drug Des.* 11:581–596 (1996).

Hacia et al., "Inhibition of Klenow Fragment DNA Polymerase on Double–Helical Templates by Oligonucleotide–Directed Triple–Helix Formation," *Biochemistry* 33:6192–6200 (1994).

Hacia et al., "Phosphorothioate Oligonucleotide–Directed Triple Helix Formation," *Biochemistry* 33:5367–5369 (1994).

Han and Dervan, "Different conformational families of pyrimidine•purine•pyrimidine triple helices depending on backbone composition," *Nucleic Acids Research* 22:2837–2844 (1994).

Han and Dervan, "Sequence–specific recognition of double helical RNA and RNA•DNA by triple helix formation," *Proc. Natl. Acad. Sci. USA* 90:3806–3810 (1993).

Han and Dervan, "Visulation of RNA tertiary structure by RNA–EDTA•Fe(II) autocleavage: Analysis of tRNA$^{Phe}$ with uridine–EDTA•Fe(II) at position 47," *Proc. Natl. Acad. Sci. USA* 91:4955–4959 (1994).

Han et al., "Mapping RNA Regions in Eukaryotic Ribosomes That Are Accessible to Methidiumpropyl–EDTA•Fe(II) and EDTA•Fe(II)," *Biochemistry* 33:9381–9844 (1994).

Harapanhalli et al., "[$^{125}$I/$^{127}$I]IodoHoechst 33342: Synthesis, DNA Binding, and Biodistribution, *J. Med. Chem.* 39:4804–4809 (1996).

Harshman and Dervan, "Molecular recognition of B–DNA by Hoechst 33258," *Nucleic Acids Research* 13:4825–4835 (1985).

He et al., *J. Am. Chem. Soc.* 115:7061–7071 (1993).

Herman et al., "Stereochemical control of the DNA binding affinity, sequence specificity, and orientation preference of chiral hairpin polyamides in the minor groove," J. Am. Chem. Soc. 120:1382–1391 (1998).

Hertzberg and Dervan, "Cleavage of DNA with Methidiumpropyl–EDTA–Iron(II): Reaction Conditions and Product Analyses," *Biochemistry* 23:3934–3945 (1984).

Hinsberg et al., "Direct Studies of 1,1–Diazenes. Syntheses, Infrared and Electronic Spectra, and Kinetics of the Thermal Decomposition of N–(2,2,6,6–Tetramethylpiperidyl)nitrene and N–(2,2,5,5–Tetramethylpyrrolidyl)nitrene," *J. Amer. Chem. Soc.* 104:766–773 (1982).

Ho et al., "Specific inhibition of formation of transcription complexes by a calicheamicin oligosaccharide: A paradigm for the development of transcriptional antagonists," Proc. Natl. Acad. Sci. USA 91:9203–9207 (1994).

Huang et al., "Design of DNA–cleaving molecules which incorporate a simplified metal–complexing moiety of bleomycin and lexitropsin carriers," *Bioorg. Med. Chem. Lett.* 3(8):1751–1756 (1993).

Huang et al., "Design, synthesis, and sequence selective DNA cleavage of functional models of bleomycin. 1. Hybrids incorporating a sample metal–complexing moiety of bleomycin and lexitropsin carriers," *Bioconjugate Chem.* 6(1):21–33 (1995).

Huang et al., "Synthesis of designed functional models of bleomycin incorporating imidazole–containing lexitropsins as novel DNA recognition sites," *Heterocycles* 41(6):1181–1196 (1995).

Huntington's Disease Collaborative Research Group, "A Novel Gene Containing a Trinucleotide Repeat That is Expanded and Unstable on Huntington's Disease Chromosomes," *Cell* 72:971–983 (1993).

Hunziker et al., "Design of an N$^7$Glycosylated Purine Nucleoside for Recognition of GC Base Pairs by Triple Helix Formation," *J. Am. Chem. Soc.* 117:2661–2662 (1995).

Hyde et al., "Some 'difficult sequences' made easy—a study of interchain association in solid–phase peptide synthesis," Int. J. Peptide Protein Res. 43:431–440 (1994).

Ikeda and Dervan, "Sequence–Selective Inhibition of Restriction Endonucleases by the Polyintercalator Bis(methidium)spermine," *J. Am. Chem. Soc.* 104:296–297 (1982).

Iverson and Dervan, "69. Cleavage of Complementary Strands of Nucleic Acids with Single Base Specificity. Enzymatic Incorporation of Modified Uridine Triphosphates" (Abstract).

Iverson and Dervan, "Adenine–Specific DNA Chemical Sequencing Reaction," *Methods in Enzymology* 218:222–227 (1993).

Iverson and Dervan, "Piperdine specific DNA chemical sequencing reaction," *Nucleic Acids Research* 14:7823–7830 (1987).

Jensen and Lysek, "Differences in the mycelial growth rhythms in a population of *Sclerotinia fructigena* (Pers.) Schroter," *Experientia* 39:1401–1402 (1983).

Jotterand–Bellomo, "The effects of distamycin A on cultured amniotic fluid cells," *Ann. Genet.* 26:27–30 (1983) (In French with English Abstract).

Kelly et al., "Binding site size limit of the 2:1 pyrrole–imidazole polyamide–DNA motif," *Proc. Natl. Acad. Sci. USA* 93:6981–6985 (1996).

Kent, *Annu. Rev. Biochem.* 57:957–989 (1988).

Kharatishvili et al., "Formation of the Left Helix On Simultaneous Exposure to Poly [d(GC)] bis–Netropsin and Zn(II) Ions," *Biophysics* 30:764–766 (1985).

Kielkopf et al., "Structural basis for G C recognition in the DNA minor groove," Nature Struct. Biol. 5(2):104–109 (1998).

Kiessling et al., "Flanking Sequence Effects within the Pyrimidine Triple–Helix Motif Characterized by Affinity Cleaving," *Biochemistry* 31:2829–2834 (1992).

Kim et al., "Crystal structure of yeast TBP/TATA–box complex," *Nature* 365:512–520 (1993).

Koh and Dervan, "Design of a Nonnatural Deoxyribonucleoside for Recognition of GC Base Pairs by Oligonucleotice–Directed Triple Helix Formation," *J. Am. Chem. Soc.* 114:1470–1478 (1992).

Kopka et al., "Defining CG–specificity in the minor groove: Side by side binding of the diimidazole lexitropsin to C–A–T–G–G–C–C–A–T–G," *Structure* 5:1033–1046 (1997).

Koppel et al., "Basicity of 3–Aminopropionamidine Derivatives in Water and Dimethyl Sulphoxide, Implication for a Pivotal Step in the Synthesis of Distamycin A Analogues," *Journal of Physical Organic Chemistry* 9:265–268 (1996).

Koshlap et al., "Nonnatural Deoxyribonucleoside $D_3$ Incorporated in an Intramolecular DNA Triplex Binds Sequence–Specifically by Intercalation," *J. Am. Chem. Soc.* 115:7908–7909 (1993).

Kothekar et al., "Influence of Local Excitations in DNA Conformation on Binding of Nonintercalating Antitumor Antibiotic in the Minor Groove," *International Journal of Quantum Chemistry: Quantum Biology Symposium* 13:175–183 (1986).

Krauch et al., "New Base Pairs for DNA and RNA" (abstract).

Krowicki and Lown, "Synthesis of Novel Imidazole–Containing DNA Minor Groove Binding Oligopeptides Related to the Antiviral Antibiotic Netropsin," *J. Org. Chem.* 52:3493–3501 (1987).

Kucerova et al., "Netropsin stimulates the formation of an extracellular proteinase and suppresses protein turnover in sporulating *Bacillus megaterium*," *FEMS Microbiology Letters* 34:21–26 (1986).

Kumar et al., "Molecular recognition and binding of a GC site–avoiding thiazole–lexitropsin to the decadeoxyribonucleotide d–[CGCAATTCGC]$_2$: *An H–NMR evidence for thiazole intercalation*," *J. Biol. Struct. Dyn.* 8(1):99–121 (1990).

Kumar et al., "Structural and dynamic aspects of non–intercalative (1:1) binding of a thiazole–lexitropsin to the decadeoxyribonucleotide d–[CGCAATTCGC]$_2$: An H–NMR and molecular modeling study," *J. Biomol. Struct. Dyn.* 9(1):1–21 (1991).

Kuroda et al., "Intelligent compounds which read DNA base sequences," *Supramolecular Chemistry* 6:95–102 (1995).

Kurreck et al., "ENDOR spectroscopy—A promising technique for investigating the structure of organic radicals," *Angew. Chem. Int. Ed. Engl.* 23:173–194 (1984).

Lane et al., "Sequence specificity of actinomycin D and Netropsin binding to pBR322 DNA analyzed by protection by Dnase I," *Proc. Natl. Acad. Sci. USA* 80:3260–3264 (1983).

Larsen and Dickerson, "As the Helix Turns, or, Rational Design of Sequence Specific DNA Minor Groove Binding Drugs," *J. Mol. Graphics* 6:211 (1988).

Lee and Walker, "Ch. 3—Sequence–Selective Binding of DNA by Oligopeptides as a Novel Approach to Drug Design," in *Polymeric Drugs and Drug Administration* American Chemical Society, pp. 29–46 (1994).

Lee et al., "Structural and Dynamic Aspects of the Sequence Specific Binding of Netropsin and its Bis–Imidazole Analogue on the Decadeoxyribonucleotide d–[CGCAATTGCG]$_2$," *Journal of Biomolecular Structure & Dynanmics* 5:939–949 (1988).

Lee et al., "Molecular recognition between oligopeptides and nucleic acids. Specificity of binding of a monocationic bis–furan lexitropsin to DNA deduced from footprinting and H NMR studies," *J. Mol. Recognit.* 2(2):84–93 (1989).

Lee et al., "Sequence specific molecular recognition and binding of a monocationic bis–imidazole lexitropsin to the decadeoxyribonucleotide d–[(GATCCGTATG) (CATACG-GATC)]: structural and dynamic aspects of intermolecular exchange studied by H–NMR," *J. Biomol. Struct. Dyn.* 5(5):1050–1987 (1988).

Leinsoo et al., "Attachment of Trivaline to a Netropsin Analog Changes the Specificity of its Binding to DNA," *Institute of Molecular Biology*, Academy of Sciences of USSR, pp. 134–148 (1988) translated from *Molekulyarnaya Biologiya* 22(1):159–175 (1988).

Levina et al., "Conjugates of Minor Groove DNA Binders with Oligodeoxynucleotides: Synthesis and Properties," *Antisense & Nucleic Acid Drug Development* 7:75–85 (1996).

Liquier et al., "FTIR Study of Netropsin Binding to Poly d(A–T) and Poly dA•PolydT," *J. Biomolecular Structure & Dynamics* 7:119–126 (1989).

Liu et al., "Sequence–selective carbohydrate–DNA interaction: dimeric and monomeric forms of the calilcheamicin oligosacccaride interfere with transcription factor function," *Proc. Natl. Acad. Sci. USA* 93:940–944 (1996).

Lombardi and Crisanti, "Antimalarial Activity of Synthetic Analogues of Distamycin," *Pharmacol. Ther.* 76:125–133 (1977).

Lown and Krowicki, "Efficient Total Synthesis of the Oligopeptide Antibiotics Netropsin and Distamaycin," *J. Org. Chem.* 50:3774–3779 (1985).

Lown et al., "Molecular Recognition between Oligopeptides and Nucleic Acids: Novel Imidazole–Containing Oligopeptides Related to Netropsin That Exhibit Altered DNA Sequence Specificity," *Biochemistry* 25:7408–7416 (1986).

Lown et al., "Novel Linked Antiviral and Antitumor Agents Related to Netropsin and Distamycin: Synthesis and Biological Evaluation," *J. Med. Chem.* 32:2368–2375 (1989).

Lown et al., "Structure–Activity Relationship of Novel Oligopeptide Antiviral and Antitumor Agents Related to Netropsin and Distamycin," *J. Med. Chem.* 29:1210–1214 (1986).

Lown, "Design and Development of Sequence Selective Lexitropsin DNA Minor Groove Binders," *Drug Development Research* 34:145–183 (1995).

Lown, "Design of sequence–specific agents: Lexitropsins," *Mol. Aspects Anticancer Drug—DNA Interact* Ch. 11:322–355 (1993).

Lown, "DNA recognition by lexitropsins, minor groove binding agents," *J. Mol. Recognit.* 7(2):79–88 (1994).

Lown, "Lexitropsins in antiviral drug development," *Antiviral Res.* 17(3):179–196 (1992).

Lown, "Synthetic chemistry of naturally ocurring oligopeptide antibiotics and related lexitropsins," *Org. Prep. Proced. Int.* 21(1):1–46 (1989).

Lu–D et al., "Synthesis and antiviral activity of 3 pyrazole analogs of distamycin–A," *Acta Chemica Scandivavica* v48(6):498–505 (1994).

Luebke and Dervan, "Nonenzymatic Ligation of Oligodeoxyribonucleotides on a Duplex DNA Template by Triple–Helix Formation," *J. Am. Chem. Soc.* 111:8733–8735 (1989).

Lythgoe and Ramsden, "4–Unsubstituted, 5–Amino and 5–Unsubstituted, 4–Aminoimidazoles," *Advances in Heterocyclic Chemistry* 61:1–58 (1994).

Mack and Dervan, "Sequence–Specific Oxidative Cleavage of DNA by a Designed Metalloprotein, Ni(II)•GGH(Hin139–190)," *Biochemistry* 31:9399–9405 (1992).

Maher et al., "Analysis of Promoter–Specific Repression by Triple–Helical DNA Complexes in a Eukaryotic Cell–Free Transcription System," *Biochemistry* 31:70–81 (1992).

Maher et al., "Inhibition of DNA Binding Proteins by Oligonucleotide–Directed Triple Helix Formation," *Science* 245:725–730 (1989).

Malcolm and Snounou, "Netropsin Increases the Linking Number of DNA," pp. 323–326.

Marck et al., "Specific interaction of netropsin, distamycin–3 and analogs with I.C. duplexes: reversion towards the B form of the 2–deoxy–, 2'–deoxy–2'–fluoro–hybrid duplexes upon specific interactions with netropsin, distamycin–3 and analogs," *Nucleic Acids Research* 10:6147–6161 (1982).

Marky et al., "Calorimetric and spectroscopic investigation of drug–DNA interactions. I. The Binding of netropsin to poly d(AT)," *Nucleic Acids Research* 11:2857–2871 (1983).

Marky, "Interaction of a Non–Intergalative Drug with DNA: Netropsin," pp. 417–418.

Martello et al., "Specific Activation of Open Complex Formation at an *Escherichia coli* Promoter by Oligo(N–methylpyrrolecarboxamide)s: Effects of Peptide Length and Identification of DNA Target Sites," *Biochemistry* 28:4455–4461 (1989).

Matyasek et al., "Evidence for a sequence–directed conformation periodicity in the genomic highly repetitive DNA detectable with single–strand–specific chemical probe potassium permangante," *Chromosome Research* 4:340–349 (1996).

Mazurek et al., "The binding of prototype lexitropsins to the minor groove of DNA: Quantum chemical studies," *J. Biomol. Struct. Dyn.* 9(2)299–313 (1991).

Milton et al., "Total chemical synthesis of a D–enzyme: The enantiomers of HIV–1 protease show demonstration of reciprocal chiral substrate specificity," *Science* 256:1445–1448 (1992).

Mitchell and Dervan, "Interhelical DNA–DNA Cross–linking. Bis(monoazidomethidium) octaoxahexacosanediamine: A Probe of Packaged Nucleic Acid," *J. Am. Chem. Soc.* 104:4265–4266 (1982).

Momose et al., "3–hydroxypyrroles. I. A general synthetic route to 4,5–unsubstituted alkyl 3–hydroxypyrrole–2–carboxylates," *Chemical Pharmacology Bulletin* 26:2224–2232 (1978).

Momose et al., "3–hydroxypyrroles. II. The reaction of 4,5–unsubstituted alkyl 3–hydroxypyrrole–2–carboxylates with some electrophiles," *Chemical Pharmacology Bulletin* 26:3521–3529 (1978).

Moser and Dervan, "Sequence–Specific Cleavage of Double Helical DNA by Triple Helix Formation," *Science* 238:645–650 (1987).

Mosher et al., "Synthesis of N–Methyl–2–trichloroacetylpyrrole—A Key Building Block in Peptides that Bind DNA: Micro–, Semimicro–, and Macro–Scale Organic Lab Experiments," *Journal of Chemical Education* 73:1036–1039 (1996).

Mrksich and Dervan, "Antiparallel Side–by–Side Heterodimer for Sequence–Specific Recognition in the Minor Groove of DNA by a Distamycin/1–Methylimidazole–2–carboxamide–netropsin Pair," *J. Am. Chem. Soc.* 115:2572–2576 (1993).

Mrksich and Dervan, "Design of a Covalent Peptide Heterodimer of Sequence–Specific Recognition in the Minor Groove of Double–Helix DNA," *J. Am. Chem. Soc.* 116:3663–3664 (1994).

Mrksich and Dervan, "Enhanced Sequence Specific Recognition in the Minor Groove of DNA by Covalent Peptide Dimers: Bis(pyridine–2–carboxamidonetropsin) $(CH_2)_{3-6}$," *J. Am. Chem. Soc.* 115:9892–9899 (1993).

Mrksich and Dervan, "Recognition in the Minor Groove of DNA at 5'–(A,T) GCGC(A,T)–3' by a Four Ring Tripeptide Dimer. Reversal of the Specificity of the Natural Product Distamycin," *J. Am. Chem. Soc.* 117:3325–3332 (1995).

Mrksich et al., "Antiparallel side–by–side dimeric motif for sequence–specific recognition in the minor groove of DNA by the designed peptide 1–methylimidazole–2–carboxamide netropsin," *Proc. Natl. Acad. Sci. USA* 89:7586–7590 (1992).

Mrksich et al., "Hairpin Peptide Motif. A New Class of Oligopeptides for Sequence–Specific Recognition in the Minor Groove of Double–Helical DNA," *J. Am. Chem. Soc.* 116:7983–7988 (1994).

Mrksich et al., "Design of a covalent peptide heterodimer for sequence–specific recognition in the minor groove of double–helical DNA," *J. Am. Chem. Soc.* 116:3663–1664 (1994).

Mrksich et al., Abstracts of the American Chemical Society 206 Part 2:413 (1993).

Mrksich, Milan, phD Thesis entitled *Design of Peptides for Sequence–Specific Recognition of the Minor Groove of DNA*, California Institute of Technology, Pasadena, California (submitted Mar. 8, 1994).

Nealy et al., "Importance of minor groove binding zinc fingers within the transcriptional factor IIIA DNA complex," *J. Mol. Biol.* in press 439–445 (1997).

Nechipurenko et al., "Cooperative Interactions Between Analogs of Distamycin A, Adsorbed on DNA," *Institute of Molecular Biology*, Academy of Sciences of USSR, pp. 263–272 (1984) translated from *Molekulyarnaya Biologiya* 18(2):332–342 (1984).

Nielsen, "Design of sequence–specific DNA–binding ligands," Chem. Eur. J. 3:505–508 (1997).

Nikolaev et al., "Design of Sequence–Specific DNA Binding Ligands that Use a Two–Stranded Peptide Motif for DNA Sequence Recognition," *Journal of Biomolecular Structure & Dynamics* 14:31–47 (1996).

Nilsson et al., "Structure at restriction endonuclease Mbol cleavage sites protected by actinomycin D or distamycin A," *FEBS Letters* 145:360–364 (1982).

Nishiwaki et al., "Efficient Synthesis of Oligo–N–Methylpyrrolecarboxamides and Related Compounds," *Heterocycles* 27:1945–1952 (1988).

Oakley et al., "Synthesis of a Hybrid Protein Containing the Iron–Binding Ligand of Bleomycin and the DNA–Binding Domain of Hin," *Bioconjugate Chem.* 5:242–247 (1994).

Oakley et al., "Evidence that a major groove–binding peptide can simultaneously occupy a common site on DNA," *Biochemistry* 31:10969–10975 (1992).

Oakley, thesis entitled "Design, Synthesis and characterization of sequence–specific DNA, cleaning metallophoteths," California Institute of Technology, Pasadena, California Submitted Nov. 8, 1993.

Ochi et al., "New Heritable Fragile Site on Chromosome 8 Induced by Distamycin A," *Jpn. J. Cancer Res.* 79:145–147 (1988).

Parks et al., "Optimization of the Hairpin Polyamide Design for Recognition of the Minor Groove of DNA," *J. Am. Chem. Soc.* 118:6147–6152 (1996).

Parks et al., "Recognition of 5'–(A,T)GG(A,T)$_2$–3' Sequences in the Minor Groove of DNA by Hairpin Polyamides," *J. Am. Chem. Soc.* 118:6153–6159 (1996).

Parrack et al., "Interaction of synthetic analogs of distamycin with DNA: Role of the conjugated N–methylpyrrole system in specificity of binding," *FEBS Letters* 212:297–301 (1987).

Pelton et al., "Binding modes of distamycin–A with d(CGCAAATTTGCG) determined by 2–dimensional NMR," J. Am. Chem. Soc. 112:1393–1399 (1990).

Pelton et al., "Structural characterization of a 2–1 distamycin A–d(CGCAAATTTGGC) complex by two dimensional NMR," Proc. Natl. Acad. Sci. USA 86:5723–5727 (1989).

Pilch et al.,. "Binding of a hairpin polyamide in the minor groove of DNA: Sequence–specific enthalpic discrimination," Proc. Natl. Acad. Sci. USA 93:8306–8311 (1996).

Portugal and Waring, "Comparison of binding sites in DNA for berenil, netropsin and distamycin: A footprinting study," *Eur. J. Biochem.* 167:281–289 (1987).

Portugal and Waring, "Hydroxyl radical footprinting of the sequence–selective binding of netropsin and distamycin to DNA," *FEBS Letters* 225:195–200 (1987).

Portugal and Waring, "Interaction of nucleosome core particles with distamycin and echinomycin: analysis of the effect of DNA sequences," *Nucleic Acids Research* 15:885–903 (1987).

Povsic and Dervan, "Triple Helix Formation by Oligonucleotides on DNA Extended to the Physiological pH Range," *J. Am. Chem. Soc.* 111:3059–3061 (1989).

Priestley and Dervan, "Sequence Composition Effects on the Energetics of Triple Helix Formation by Oligonucleotides Containing a Designed Mimic of Protonated Cytosine," *J. Am. Chem. Soc.* 117:4761–4765 (1995).

Pullman, *Adv. Drug. Res.* 18:1–113 (1990).

Radhakrishnan and Patel, "NMR Structural Studies on a Nonnatural Deoxyribonucleoside Which Mediates Recognition of GC Base Pairs in Pyrimidine•Purine•Pyrimidine DNA Triplexes," *Biochemistry* 32:11228–11234 (1993).

Rajagopalan et al., "Interaction of non–intercalative drugs with DNA: Distamycin analogues," *J. Biosci.* 7:27–32(1985).

Rajagopalan et al., "Synthesis of a Distamycin Analogue: Tris(m–benzamido) Compound," *Indian Journal of Chemistry* 26B:1021–1024 (1987).

Rao et al., "Interaction of Synthetic Analogues of Distamycin and Netropsin with Nucleic Acids. Does Curvature of Ligand Play a Role in Distamycin–DNA Interactions?" *Biochemistry* 27:3018–3024 (1988).

Rao et al., "Molecular recognition between ligands and nucleic acids: Sequence preferences and binding of Pyrrolo [3,2–d] and [2,3–d]thiazole–containing lexitropsins deduced from MPE–Fe(II) footprinting," *Actual. Chim. Ther.* 20:159–188 (1993).

Rao et al., "Molecular recognition between oligopeptides and nucleic acids: DNA binding selectivity of a series of 1,2,4–triazole–containing lexitropsins," *Chem. Res. Toxicol.* 4(2):241–252 (1991).

Rao et al., "Psoralen–lexitropsin hybrids: DNA sequence selectivity of photoinduced cross–linking from MPE footprinting and exonuclease III stop assay, and mode of binding from electric linear dichroism," *Anti–Cancer Drug Des.* 9(3):221–237 (1994).

Rao et al., "Sequence–selective DNA binding by linked Bis–N–methylpyrrole dipeptides: an analysis of MPE footprinting and force field calculations," *J. Org. Chem.* 56(2):786–797 (1991).

Reinert et al., "Deformyldistamycin—DNA Interaction; DNA Conformational Changes as Revealed by Titration Rotational Viscometry," *J. Biomolecular Structure & Dynamics* 14(2):245–253 (1996).

Reinert et al., "DNA interaction of the imidazole–containing lexitropsin ImPy: Titration viscometric study in comparison to Netropsin," *J. Biomol. Struct. Dyn.* 12(4):847–855 (1995).

Ronne et al., "The effect of in vitro distamycin A exposure on metaphase chromosome structure," *Hereditas* 96:269–277 (1982).

Royyuru et al., "Theoretical Study of Conformational Flexibility of Distamycin–A Analog and its Binding to DNA," *Current Science* 56:581–584 (1987).

Rubin et al., "An unexpected major groove binding of netropsin and distamycin A to tRNA$^{phe}$," *Journal of Biomolecular Structure and Dynamics* 2:165–174 (1984).

Sakaguchi et al., "Effect of netropsin on plasmid DNA cleavage by BAL 31 nuclease," *FEBS Letters* 191:59–62 (1985).

Salmanova et al., "Interaction of DNA with Synthetic Ligands Containing N,4–Disubstituted Mono– and Diphthalimides," *Molecular Biology* 29:491–498 (1995).

Sanfilippo et al., "Activity of the Distamycin A on the Induction of Adaptive Enzymes in *Escherichia coli*," *J. gen. Microbiol.* 43:369–374 (1966).

Sarma et al., "Structure of Poly(dA)•Poly(dT) is not Identical to the AT Rich Regions of the Single Crystal Structure of CGCGAATT$^{Br}$CGCG. The Consequence of this to Netropsin Binding to Poly(dA)•Poly(dT)," *J. Biomolecular Structure & Dynamics* 3(3):433–436 (1985).

Schabel et al., "Observations on Antiviral Activity of Netropsin," *Proceedings of the Society for Experimental Biology and Medicine* 83:1–3 (1953).

Schmid et al., "Characterization of a Y/15 translocation by banding methods, distamycin A treatment of lymphocytes and DNA restriction endonuclease analysis," *Clinical Genetics* 24:234–239 (1983).

Schmid et al., "The use of distamycin A in human lymphocyte cultures," *Human Genet* 65:377–384 (1984).

Schuhmann et al., "Wirkung von Distamycin A und Netropsin auf normale und zellwandlose Zellen von *Escherichia coli* W 1655F$^+$," *Zeitschrift fur Allg. Mikrobiologie* 14:321–327 (1974) (In German with English Abstract).

Schultz and Dervan, "Distamycin and Penta–N–Methylpyrrolecarboxamide Binding Sites on Native DNA—A Comparison of Methidiumpropyl–EDTA–Fe(II) Footprinting and DNA Affinity Cleaving," *J. Biomolecular Structure & Dynamics* 1:1133–1147 (1984).

Schultz and Dervan, "Sequence–specific double–strand cleavage of DNA by penta–N–methylpyrrolecarboxamide–EDTA•Fe(II)," *Proc. Natl. Acad. Sci. USA* 80:6834–6837 (1983).

Schultz, "141. Design and Synthesis of Sequence Specific DNA Cleaving Molecules" (Abstract).

Schultz, thesis entitled "I. Ground and excited state studies of persistent 1,1–diazenes," and "II. Design of sequence specific DNA cleaving molecules," California Institute of Technology, Pasadena, California Submitted Feb. 2, 1989.

Schulz and Dervan, "Sequence–Specific Double–Strand Cleavage of DNA by Bis(EDTA–distamycin–Fe$^{II}$) and EDTA–Bis(distamycin)•Fe$^{II}$," *J. Am. Chem. Soc.* 105:7748–7750 (1983).

Seeman et al., "Sequence specific recognition of double helical nucleic acids by proteins," *Proc. Natl. Acad. Sci. USA* 73:804–808 (1976).

Sengupta et al., "A Microgonotropen Pentaaza Pentabutylamine and its Interactions with DNA," *Bioorganic & Medicinal Chemistry* 4:803–813 (1996).

Shabtai et al., "Familial fragile site found at the cancer breakpoint (1)(q32): Inducibility by distamycin A, concomitance with gragile (16)(q22)," *Hum Genet* 73:232–234 (1986).

Shabtai et al., "Familial Fragility on Chromosome 16 (Fra 16q22) Enhanced by Both Interferon and Distamycin A," *Hum Genet* 63:341–344 (1983).

Shin, Sluka, Horvath, Simon and Dervan, "99. Synthetic DNA–Cleaving Proteins" (Abstract).

Shishido et al., "Enhancement of S1 Nuclease–Susceptibility of Negatively Superhelical DNA by Netropsin," *Biochemical & Biophysical Research Communications* 124:388–392 (1984).

Sidorova et al., "Competition between Netropsin and Restriction Nuclease EcoRI for DNA Binding," *J. Biomolecular & Dynamics* 13(2):367–385 (1995).

Singh et al., "Isohelicity and Strand Selectivity in the Minor Groove Binding of Chiral (1R,2R)– and (1S,2S)–Bis(netropsin)–1,2–cyclopropanedicarboxamide Ligands to Duplex DNA," *J. Am. Chem. Soc.* 116:7006–7020 (1994).

Singh et al., "A H–NMR study of the DNA binding characteristics of thioformyldistamycin an amide isoteric lexitropsin," *Biochemistry* 31(28):6453–6461 (1992).

Singh et al., "Relative binding affinities of distamycin an its analog to d(CGCAAGTTCCG) d(GCCAACTTGCG): Comparison of simulation results with experiment," Proc. Natl. Acad. Sci. USA 91:7673–7677 (1994).

Singh et al., "Structural characterization of side–by–side binding for a cross–linked lexitropsin dimer designed to target G–C base pairs in the DNA minor groove," *Magn. Reson. Chem.* 34:S55–S66 (1996).

Singleton and Dervan, "Equilibrium Association Constants for Oligonucleotide–Directed Triple Helix Formation at Single DNA Sites: Linkage to Cation Valence and Concentration," *Biochemistry* 32:13171–13179 (1993).

Singleton and Dervan, "Influence of ph on the Equilibrium Association Constants for Oligodeoxyribonucleotide–Directed Triple Helix Formation at Single DNA Sites," *Biochemistry* 31:10995–11003 (1992).

Singleton and Dervan, "Temperature Dependence of the Energetics of Oligonucleotide–Directed Triple–Helix Formation at a Single DNA Site," *J. Am. Chem. Soc.* 116:10376–10382 (1994).

Skamrov et al., "Specific Protection of DNA from the Action of Dnase I by Distamycin A, Netropsin, and Bis–Netropsins," Institute of Molecular Biology, Academy of Sciences of USSR, pp. 153–167 (1985) translated from *Molekulyarnaya Biologiya* 19(1):177–195 (1985).

Sluka et al., "Synthesis of a Sequence–Specific DNA–Cleaving Peptide," *Science* 238:1129–1132 (1987).

Sluka et al., "Structural studies of protein–nucleic acid interaction: The source of sequence–specific binding," *Quart. Rev. Biophys.* 23:203–280 (1990).

Snounou and Malcolm, "Production of Positively Supercoiled DNA by Netropsin," *J. Mol. Biol.* 167:211–216 (1983).

Sponar and Votavova, "Selective Binding of Synthetic Polypeptides to DNA of Varying Composition and Sequence: Effect of Minor Groove Binding Drugs," *J. Biomolecular Structure & Dynamics* 13(6):979–987 (1996).

Stanchev et al., "Netropsin, Distamycin A, bis–Netropsins as Selective Inhibitors of the Effect of Restrictase and DNase I," Institute of Molecular Biology, Academy of Sciences of USSR, pp. 1324–1333 (1987) translated from *Molekulyarnaya Biologiya* 20(6):1614–1624 (1986).

Staubli and Dervan, "Sequence specificity of the non–natural pyrido[2,3–d]pyrimidine nucleoside in triple helix formation," *Nucleic Acids Research* 22:2637–2642 (1994).

Stilz and Dervan, "Specific Recognition of CG Base Pairs by 2–Deoxynebularine within the Purine•Purine•Pyrimidine Triple–Helix Motif," *Biochemistry* 32:2177–2185 (1993).

Strobel and Dervan, "Cooperative Site Specific Binding of Oligonucleotides to Duplex DNA," *J. Am. Chem. Soc.* 111:7286–7287 (1989).

Strobel and Dervan, "Triple Helix–Mediated Single–Site Enzymatic Cleavage of Megabase Genomic DNA," *Methods in Enzymology* 216:309–321 (1992).

Surovaya et al., "Construction of Peptide β–Hairpins Recognizing DNA Sequences," *Molecular Biology* 30:818–825 (1996).

Swalley et al., "Recognition of a 5'–(A,T)GGG(A,T)$_2$–3' Sequence in the Minor Groove of DNA by an Eight–Ring Hairpin Polyamide," *J. Am. Chem. Soc.* 118:8198–8206 (1996).

Swalley et al., *Chem. Eur. J.* 3:1600–1607 (1997).

Swalley et al., "Discrimination of 5'–GGGG–3', 5'–GCGC–3' sequences in the minor groove of DNA by eight–ring hairpin polyamides," *J. Am. Chem. Soc.* 119:6953–6961 (1997).

Szewczyk et al., "Cooperative triple–helix formation via a minor groove dimerization domain," *J. Am. Chem. Soc.* 118:6778–6779 (1996).

Szewczyk et al., "Sequence–specific recognition of DNA by a major and minor groove binding ligand," Angew. Chem. Int. Ed. Engl. 35:1487–1489 (1996).

Takahashi et al., "82. Distamycin A–Induced Fragility on Chromosomes 16, Fra(16)(q22), in a Japanese Population," *Proc. Japan Acad.* 61(B):299–302 (1985).

Takahashi et al., "A new rare distamycin A–inducible fragile site, fra(11)(p15.1), found in two acute nonlymphocytic leukemia (ANLL) patients with t(7;11)(p15–p13;p15)," *Hum Genet* 80:124–126 (1988).

Taylor et al., "DNA Affinity Cleaving—Sequence Specific Cleavage of DNA by Distamycin–EDTA•Fe(II) and EDTA–Distamycin•Fe(II)," *Tetrahedron* 40:457–465 (1984).

Tenette et al., "Force field development and conformational search strategy in the simulation of biomolecular recognition processes," *Biochemical Society Transactions* 24:268–274 (1996).

Thuong et al., "Sequence–specific recognition and modification of double–helical DNA by oligonucleotides," Angew Chem. Int. Ed. Engl. 32:666–690 (1993).

Tor and Dervan, "Site–Specific Enzymatic Incorporation of an Unnatural Base, $N^6$–(6–Aminohexyl)isoguanosine, into RNA," *J. Am. Chem. Soc.* 115:4461–4467 (1993).

Trauger et al., "Recognition of DNA by designed ligands at subnanomolar concentrations," *Nature* 382:559–561 (1996).

Trauger et al., "Extended hairpin polyamide motif for sequence–specific recognition in the minor groove of DNA," Chem. & Biol. 3:369–377 (1996).

Trauger et al., "Extension of sequence–specific recognition and modification of double–helical DNA by pyrrole–imidazole polyamides to 9–13 base pairs," J. Am. Chem. Soc. 118:6160–6166 (1996).

Turner et al., "The mutagenic properties of DNA minor–groove binding ligands," *Mutation Research* 355:141–149 (1996).

Turner et al., "Recognition of 7 base–pair sequences in the minor groove of DNA by 10 ring pyrrole–imidazole polyamides," J. Am. Chem. Soc. 119:7636–7644 (1997).

Uchida et al., "High resolution footprinting of EcoRI and distamycin with $Rh(phi)_2(bpy)^{3+}$, a new photofootprinting reagent," *Nucleic Acids Research* 17:10259–10279 (1989).

Van Dyke and Dervan, "Chromoycin, Mithramycin, and Olivomycin Binding Sites on Heterogeneous Deoxyribonucleic Acid. Footprinting with (Methidiumpropyl–EDTA) iron (II)," *Biochemistry* 22:2373–2377 (1983).

Van Dyke and Dervan, "Echinomycin Binding Sites on DNA," *Science* 225:1122–1127 (1984).

Van Dyke and Dervan, "Footprinting with MPE•Fe(II). Complementary–strand Analyses of Distamycin– and Actinomycin–binding Sites on Heterogeneous DNA," pp. 347–353.

Van Dyke and Dervan, "Methidiumpropyl–EDTA•Fe(II) and DNase I footprinting report different small molecule binding site sizes on DNA," *Nucleic Acids Research* 11:5555–5567 (1983).

Van Dyke et al., "Map of distamycin, netropsin, and actinomycin binding sites on heterogeneous DNA: DNA cleavage–inhibition patterns with methidiumpropyl–EDTA•FE(II)," *Proc. Natl. Acad. Sci. USA* 79:5470–5474 (1982).

Vigneswaran et al., "Influence of GC and AT Specific DNA Minor Groove Binding Drugs on Intermolecular Triplex Formation in the Human c–Ki–ras Promoter," *Biochemistry* 35:1106–1114 (1996).

Wade and Dervan, "Alteration of the Sequence Specificity of Distamycin on DNA by Replacement of an N–Methylpyrrolecarboxamide with Pyridine–2–carboxamide," *J. Am. Chem. Soc.* 109:1574–1575 (1987).

Wade et al., "Binding Affinities of Synthetic Peptides, Pyridine–2–carboxamidonetropsin and 1–Methylimidazole–2–carboxamidonetropsin, That Form 2:1 Complexes in the Minor Groove of Double–Helical DNA," *Biochemistry* 32:11385–11389 (1993).

Wade et al., "Design of Peptides That Bind in the Minor Groove of DNA at 5'–(A,T)G(A,T)C(A,T)–3' Sequences by a Dimeric Side–by–Side Motif," *J. Am. Chem. Soc.* 114:8783–8794 (1992).

Wade et al., "Recognition of G,C Base Pairs in the Minor Groove of DNA" (Abstract).

Wade, thesis entitled Sequence specific complexation of BDNA at sites containing G, C base pairs, California Institute of Technology, Pasadena, California Submitted Feb. 2, 1989.

Walker et al., "Estimation of the DNA sequence discriminatory ability of hairpin–linked lexitropsins," Proc. Natl. Acad. Sci. USA 94:5634–5639 (1997).

Wang et al., "Interactions Between a Symmetrical Minor Groove Binding Compound and DNA Oligonucleotides: $^1H$ and $^{19}F$ NMR Studies," *J. Biomolecular Structure & Dynamics* 7:101–117 (1989).

Wang et al., "Anti HIV–1 activity of linked lexitropsins," *J. Med. Chem.* 35(15):2890–2897 (1992).

Wang et al., "Convenient synthesis of pyrroloiminoquinone and its lexitropsin–linked derivative," *Tetrahedron Lett.* 35(24):4085–4086 (1994).

Wang et al.,"Design, synthesis, cytotoxic properties and preliminary DNA sequencing evaluation of CPI–N–methylpyrrole hybrids. Enhancing effect of a trans double bond linker and role of the terminal amide functionality on cytotoxic potency," *Anti–Cancer Drug Des.* 11(1):15–34 (1996).

Ward et al., "Determination of Netropsin–DNA Binding Constants from Footprinting Data," *Biochemistry* 27:1198–1205 (1988).

Ward et al., "Quantitative Footprinting Analysis of the Netropsin—DNA Interaction," *J. Biomolecular Structure & Dynamics* 4(5):685–695 (1987).

Wemmer et al., "Targeting the minor groove of DNA," *Curr. Opin. Struct. Biol.* 7:355–361 (1997).

Wemmer et al., *Abstracts of the American Chemical Society* 208 Part 2:9 (1994).

White et al., "Effects of the A●T/T●A degeneracy of pyrrole–imidazole polyamide recognition in the minor groove of DNA," *Biochemistry* 35:12532–12537 (1996).

White et al., "On the pairing rules for recognition in the minor groove of DNA by pyrrole–imidazole polyamides," *Chem. & Biol.* 4:569–578 (1997).

White et al., "Orientation preferences of pyrrole–imidazole in the minor groove of DNA," *J. Am. Chem. Soc.* 119:756–765 (1997).

White et al., "Recognition of the Watson–Crick base pairs in the DNA minor groove by synthetic ligands," *Nature* 391:468–471 (1998).

Wiederholt et al., "DNA–Tethered Hoechst Groove–Binding Agents: Duplex Stabilization and Fluorescence Characteristics," *J. Amer. Chem. Soc.* 118:7055–7062 (1996).

Wilkins, "Selective binding of actinomycin D and distamycin A to DNA," *Nucleic Acids Research* 10:7273–7282 (1982).

Williamson et al., "Phase–Sensitive Heteronuclear Multiple– Bond Correlation in the Presence of Modest Homonuclear Coupling. Application to Distamycin A," *Journal of Magnetic Resonance* 82:605–612 (1989).

Wong and Bateman, "TBP—DNA interactions in the minor groove discriminate between A:T and T:A base pairs," *Nucleic Acids Research* 22:1890–51896 (1994).

Woynarowski et al., "DNA Minor–Groove Binding Agents Interfere with Topoisomerase II–Medidated Effects of VM–26 and m–AMSA," *Proceedings of AACR* 29:274 at abstract No. 1089 (1988).

Xie et al., "Synthesis and DNA cleaving properties of hybrid molecules containing propargylic sulfones and minor groove binding lexitropsins," *Bioorg. Med. Chem. Lett.* 3(8):1565–1570 (1993).

Yamaguchi et al., Nuclear magnetic resonance analysis using chiral derivatives. In: Asymmetric Synthesis (vol. 1), Analytical Methods, Ed. J.D. Morrison pp. 125–152 Academic Press (1993).

Yamamoto et al., "Synthesis and DNA Binding Properties of Amide Bond–Modified Analogues Related to Distamycin," *Tetrahedron Letters* 37:7801–7804 (1996).

Yang et al., "Studies on Cooperative Binding of an Extended Distamycin A Analogue in the Minor Groove of DNA by NMR Spectroscopy," *Biochemical and Biophysical Research Communications* 222:764–769 (1996).

Youngquist and Dervan, "Sequence–specific recognition of B–DNA by oligo(N–methylpyrrolecarboxamide)s," *Proc. Natl. Acad. Sci. USA* 82:2565–2569 (1985).

Youngquist and Dervan, "Sequence–specific recognition of B–DNA by Bis(EDTA–distamycin)fumaramide," *J. Am. Chem. Soc.* 107:5528–5529 (1985).

Zakrzewska and Pullman, "Theoretical Study of the Sequence Selectivity of Isolexins, Isohelical DNA Groove Binding Ligands. Proposal for the GC Minor Groove Specific Compounds," *Journal of Biomolecular & Development* 5(5):1043–1058 (1988).

Zakrzewska et al., "Drug Recognition of DNA. Proposal for GC Minor Groove Specific Ligands: Vinylexins," *Journal of Biomolecular Structure & Development* 6(2):331–344 (1988).

Zasedatelev et al., "Mono–, di– and trimeric binding of bis–netropsin to DNA," *FEBS Letters* 375:304–306 (1995).

Zimmer and Wahnert, "Nonintercalating DNA–Binding Ligands. Specificity of the Interaction and Their Use as Tools in Biophysical, Biochemical and Biological Investigations of the Genetic Material," *Prog. Biophys. molec Biol.* 47:31–112 (1986).

Zimmer et al., "Binding of Analogues of the Antibiotics Distamycin A and Netropsin to Native DNA," *Eur. J. Biochem.* 26:81–89 (1972).

Zimmer et al., "Chain Length–Dependent Association of Distamycin–Type Oligopeptides with A•T and G•C Pairs in Polydeoxynucleotide Duplexes," *Biochimica et Biophysica Acta* 741:15–22 (1983).

Zimmer et al., "Differential stabilization by netropsin of inducible B–like conformations in deoxyribo–, ribo– and 2'–deoxy–2'–fluororibo–adenosine containing duplexes of $(dA)_n \cdot (dT)_n$ and $(dA)_n \cdot (dU)_n^a$," *Nucleic Acids Research* 10:1721–1732 (1982).

Zimmer et al., "Effects of the Antibiotics Netropsin and Distamycin A on the Structure and Function of Nucleic Acids," pp. 285–318.

Zimmer et al., "Z–DNA and other non–B–DNA structures are reversed to B–DNA by interaction with netropsin," *FEBS Letters* 154:156–160 (1983).

\* cited by examiner

1  ImImPyPy–γ–ImPyPyPy–β–Dp

2  ImImPyPy–γ–ImHpPyPy–β–Dp

3  ImImHpPy–γ–ImPyPyPy–β–Dp

Py/Py with T·A

Py/Py with A·T

Py/Hp with T·A

Py/Hp with A·T

Hp/Py with T·A

Hp/Py with A·T

POLYAMIDES FOR BINDING IN THE MINOR GROOVE OF DOUBLE STRANDED DNA

CROSS REFERENCE TO RELATED APPLICATIONS

This application claims priority to PCT/US98/01006 filed Jan. 28, 1998, and is a continuation-in-part of PCT/US97/12722, filed Jul. 27, 1997, and a continuation-in-part of PCT/US97/03332, filed Feb. 20, 1997, and a continuation-in-part of Ser. No. 08/837,524, filed Apr. 21, 1997, now U.S. Pat. No. 6,143,901, and a continuation-in-part of 08/607,078, filed Feb. 26, 1996, now U.S. Pat. No. 6,090,947, which claims the benefit of Provisional applications Ser. No. 60/044,444, filed Apr. 8, 1997, Ser. No. 60/042,022, filed Apr. 6, 1997, Ser. No. 60/038,384, filed Feb. 14, 1997, Ser. No. 60/026,713, filed Sep. 25, 1996, Ser. No. 60/024,374, filed Aug. 1, 1996, and Ser. No. 60/023,309, filed Jul. 31, 1996.

The U.S. Government has certain rights in this invention pursuant to Grant Nos. GM 26453, 27681 and 47530 awarded by the National Institute of Health.

BACKGROUND OF THE INVENTION

1. Field of the Invention

This invention relates to polyamides which bind to predetermined sequences in the minor groove of double stranded DNA.

2. Description of the Related Art

The design of synthetic ligands that read the information stored in the DNA double helix has been a long standing goal of chemistry. Cell-permeable small molecules which target predetermined DNA sequences are useful for the regulation of gene-expression. Oligodeoxynucleotides that recognize the major groove of double-helical DNA via triple-helix formation bind to a broad range of sequences with high affinity and specificity. Although oligonucleotides and their analogs have been shown to interfere with gene expression, the triple helix approach is limited to purine tracks and suffers from poor cellular uptake. The. development of pairing rules for minor groove binding polyamides derived from N-methylpyrrole (Py) and N-methylimidazole (Im) amino acids provides another code to control sequence specificity. An Im/Py pair distinguishes G·C from C·G and both of these from A·T or T·A base pairs. Wade, W. S., Mrksich, M. & Dervan, P. B. describes the design of peptides that bind in the minor groove of DNA at 5'-(A,T)G(A,T)C(A,T)-3' sequences by a dimeric side-by-side motif. *J. Am. Chem. Soc.* 114, 8783–8794 (1992); Mrksich, M. et al. describes antiparallel side-by-side motif for sequence specific-recognition in the minor groove of DNA by the designed peptide 1-methylimidazole-2-carboxamidenetropsin. *Proc. Natl. Acad. Sci. USA* 89, 7586–7590 (1992); Trauger, J. W., Baird, E. E. Dervan, P. B. describes the recognition of DNA by designed ligands at subnanomolar concentrations. *Nature* 382, 559–561 (1996). A Py/Py pair specifies A·T from G·C but does not distinguish A·T from T·A. Pelton, J. G. & Wemmer, D. E. describes the structural characterization of a 2-1 distamycin A-d (CGCAAATTTGGC) complex by two-dimensional NMR. *Proc. Natl. Acad. Sci. USA* 86, 5723–5727 (1989); White, S., Baird, E. E. & Dervan, P. B. Describes the effects of the A·T/T·A degeneracy of pyrrole-imidazole polyamide recognition in the minor groove of DNA. *Biochemistry* 35, 6147–6152 (1996); White, S., Baird, E. E. & Dervan, P. B. describes the pairing rules for recognition in the minor groove of DNA by pyrrole-imidazole polyamides. *Chem. & Biol.* 4, 569–578 (1997); White, S., Baird, E. E. & Dervan, P. B. describes the 5'-3' N-C orientation preference for polyamide binding in the minor groove. In order to break this degeneracy, a new aromatic amino acid, 3-hydroxy-N-methylpyrrole (Hp) incorporated into a polyamide and paired opposite Py, has been found to discriminate A·T from T·A. The replacement of a single hydrogen atom on the pyrrole with a hydroxy group in a Hp/Py pair regulates affinity and specificity of a polyamide by an order of magnitude. Utilizing Hp together with Py and Im in polyamides to form four aromatic amino acid pairs (Im/Py, Py/Im, Hp/Py, and Py/Hp) provides a code to distinguish all four Watson-Crick base pairs in the minor groove of DNA.

SUMMARY OF THE INVENTION

The invention encompasses improved polyamides for binding to the minor groove of double stranded ("duplex") DNA. The polyamides are in the form of a hairpin comprising two groups of at least three consecutive carboxamide residues, the two groups covalently linked by an aliphatic amino acid residue, preferably y-aminobutyric acid or 2,4 diaminobutyric acid, the consecutive carboxamide residues of the first group pairing in an antiparallel manner with the consecutive carboxamide residues of the second group in the minor groove of double stranded DNA. The improvement relates to the inclusion of a binding pair of Hp/Py carboxamides in the polyamide to bind to a T·A base pair in the minor groove of double stranded DNA or Py/Hp carboxamide binding pair in the polyamide to bind to an A·T base pair in the minor groove of double stranded DNA. The improved polyamides have at least three consecutive carboxamide pairs for binding to at least three DNA base pairs in the minor groove of a duplex DNA sequence that has at least one A·T or T·A DNA base pair, the improvement comprising selecting a Hp/Py carboxamide pair to correspond to a T·A base pair in the minor groove or a Py/Hp carboxamide pair to bind to an A·T DNA base pair in the minor groove. Preferably the binding of the carboxamide pairs to the DNA base pairs modulates the expression of a gene.

In one preferred embodiment, the polyamide includes at least four consecutive carboxamide pairs for binding to at least four base pairs in a duplex DNA sequence. In another preferred embodiment, the polyamide includes at least five consecutive carboxamide pairs for binding to at least five base pairs in a duplex DNA sequence. In yet another preferred embodiment, the polyamide includes at least six consecutive carboxamide pairs for binding to at least six base pairs in a duplex DNA sequence. In one preferred embodiment, the improved polyamides have four carboxamide binding pairs that will distinguish A·T, TEA, C·G and G·C base pairs in the minor groove of a duplex DNA sequence. The duplex DNA sequence can be a regulatory sequence, such as a promoter sequence or an enhancer sequence, or a gene sequence, such as a coding sequence or a non-coding sequence. Preferably, the duplex DNA sequence is a promoter sequence.

The preparation and the use of polyamides for binding in the minor groove of double stranded DNA are extensively described in the art. This invention is an improvement of the existing technology that uses 3-hydroxy-N-methylpyrrole to provide carboxamide binding pairs for DNA binding polyamides.

The invention encompasses polyamides having γ-aminobutyric acid or a substituted γ-aminobutyric acid to form a hairpin with a member of each carboxamide pairing on each side of it. Preferably the substituted γ-aminobutyric acid is a chiral substituted γ-aminobutyric acid such as (R)-2,4-diaminobutyric acid. In addition, the polyamides may contain an aliphatic amino acid residue, preferably a β-alanine residue, in place of a non-Hp carboxamide. The β-alanine residue is represented in formulas as β. The β-alanine residue becomes a member of a carboxamide binding pair. The invention further includes the substitution as a β-β binding pair for non-Hp containing binding pair. Thus, binding pairs in addition to the Hp/Py and Py/Hp are Im/β, β/Im, Py/β, β/Py, and β/β.

The polyamides of the invention can have additional moieties attached covalently to the polyamide. Preferably the additional moieties are attached as substituents at the amino terminus of the polyamide, the carboxy terminus of the polyamide, or at a chiral (R)-2,4-diaminobutyric acid residue. Suitable additional moieties include a detectable labeling group such as a dye, biotin or a hapten. Other suitable additional moieties are DNA reactive moieties that provide for sequence specific cleavage of the duplex DNA.

BRIEF DESCRIPTION OF THE DRAWINGS

FIG. 15 illustrates 8-ring hairpin polyamides which target 5'-WGANNW-3' sites.

FIG. 16 illustrates 8-ring hairpin polyamides which target 5'-WGGNNW-3' sites.

DETAILED DESCRIPTION OF THE INVENTION

Figure 1:
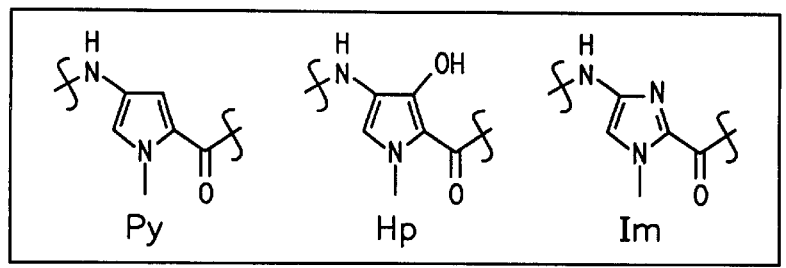
FIG. 1 illustrates the structure of polyamide 1, 2, and 3.
Figure 1:
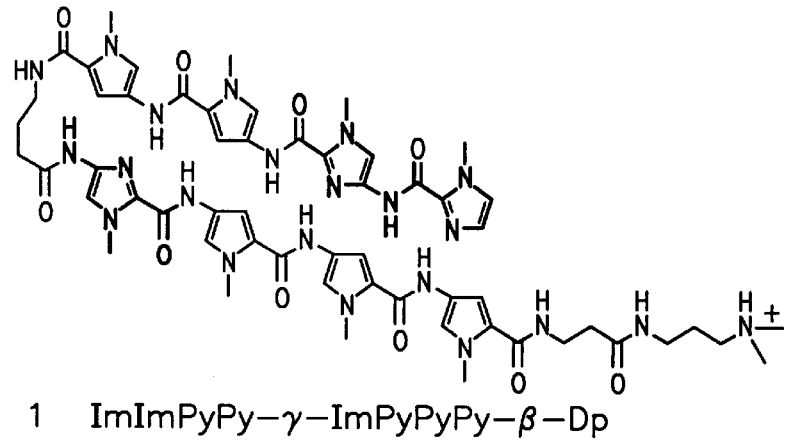
Figure 1:
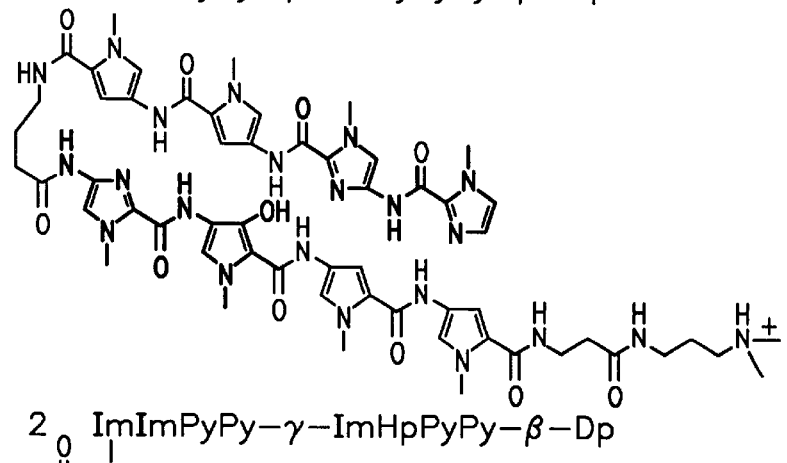
Figure 1:
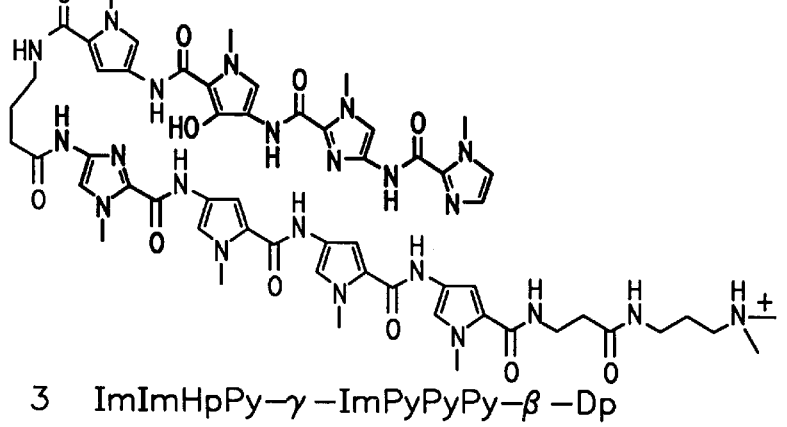

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Diego, Calif. (1990); Freshney, R. I., *Culture of Animal Cells: A Manual of Basic Technique*, 2$^{nd}$ Ed., Alan Liss, Inc. New York, N.Y. (1987); Murray, E. J., ed., *Gene Transfer and Expression Protocols*, pp. 109–128, The Humana Press Inc., Clifton, N.J. and Lewin, B., *Genes VI*, Oxford University Press, New York (1997).

For the purposes of this application, a promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("'5 to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogenous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the coding strand of DNA is positioned about 30 base pairs upstream of the transcription start site, the sequence forms part of the promoter region (Lewin, *Genes VI*, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, *Genes VI*, pp.213–215).

While not being held to one hypothesis, it is believed that the binding of the polyamides of this invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an improved polyamide of the present invention may be identified.

It is generally understood by those skilled in the art that the basic structure of DNA in a living cell includes both major and a minor groove. For the purposes of describing the present invention, the minor groove is the narrow groove of DNA as illustrated in common molecular biology references such as Lewin, B., *Genes VI*, Oxford University Press, New York (1997).

To affect gene expression in a cell, which may include causing an increase or a decrease in gene expression, a effective quantity of one or more polyamide is contacted with the cell and internalized by the cell. The cell may be contacted in vivo or in vitro. Effective extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated on tissue culture plates and various quantities of one or more polyamide are added to separate wells. Gene expression following exposure to a polyamide can be monitored in the cells or medium by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and western blot. Alternatively, gene expression following exposure to a polyamide can be monitored by the detecting the amount of messenger RNA present as determined by various techniques, including northern blot and RT-PCR.

The polyamides of this invention may be formulated into diagnostic and therapeutic compositions for in vivo or in vitro use. Representative methods of formulation may be found in *Remington: The Science and Practice of Pharmacy*, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected is compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral, psoralen, EDTA, methidium, acridine, Ni(II)·Gly-Gly-His, TO, Dansyl, pyrene, N-bromoacetamide, and gold particles. Such bifunctional polyamides are useful for DNA affinity capture, covalent DNA modification, oxidative DNA cleavage, DNA photocleavage. Such bifunctional polyamides are useful for DNA detection by providing a polyamide linked to a detectable label. Detailed instructions for synthesis of such bifunctional polyamides can be found in copending U.S. provisional application 60/043,444, the teachings of which are incorporated by reference.

DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microliter plate well to which microgram quantities of a contemplated polypamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

FIG. 1 shows representative structures of polyamides. ImImPyPy-γ-ImPyPyPy-β-Dp (1), ImImPyPy-γ-ImHpPyPy-β-Dp (2), and ImImHpPy-γ-ImPyPyPy-β-Dp (3). (Hp=3-hydroxy-N-methylpyrrole, Im=N-mehylimidazole, Py=N-methylpyrrole, β=β-alanine, γ=γ-aminobutyric acid, Dp=Dimethylaminopropylamide). Polyamides were synthesized by solid phase methods using Boc-protected 3-methoxypyrrole, imidazole, and pyrrole aromatic amino acids, cleaved from the support by aminolysis, deprotected with sodium thiophenoxide, and purified by reversed phase EPLC. Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. The identity and purity of the polyamides were verified by $^1$H NMR, analytical HPLC, and matrix-assisted laser-desorption ionization time-of-flight mass spectrometry (MALDI-TOF MS-monoisotopic): 1 1223.6 (1223.6 calculated), 2 1239.6 (1239.6 calculated); 3 1239.6 (1239.6 calculated).

Figure 2:
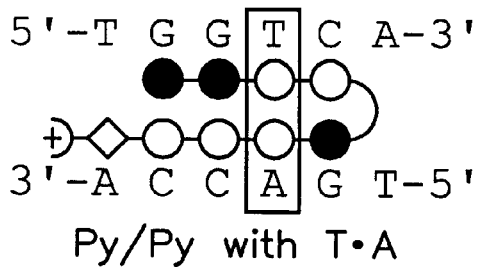
FIG. 2 illustrates the pairing of polyamides to DNA base pairs.
Figure 2:
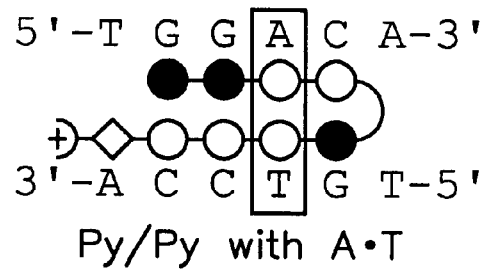
Figure 2:
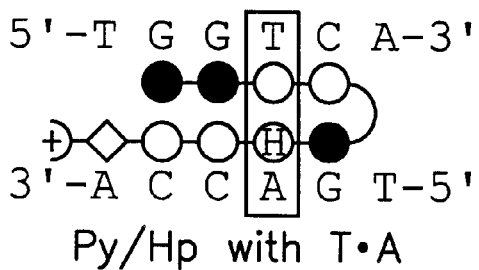
Figure 2:
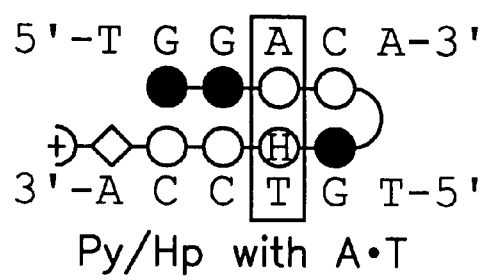
Figure 2:
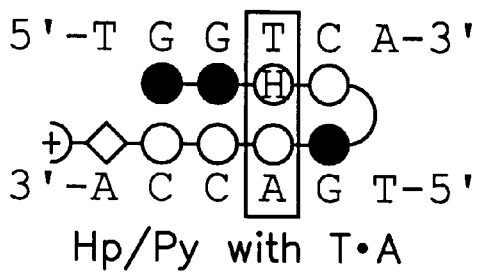
Figure 2:
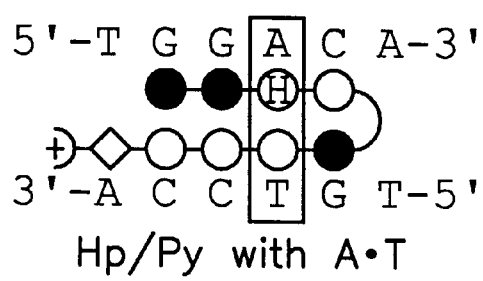

FIG. 2 illustrates binding models for polyamides 1-3 in complex with 5'-TGGTCA-3' and 5'-TGGACA-3' (A·T and T·EA in fourth position highlighted). Filled and unfilled circles represent imidazole and pyrrole rings respectively; circles containing an H represent 3-hydroxypyrrole, the curved line connecting the polyamide subunits represents γ-aminobutyric. acid, the diamond represents β-alanine, and the + represents the positively charged dimethylaminopropylamide tail group.

Figure 3:
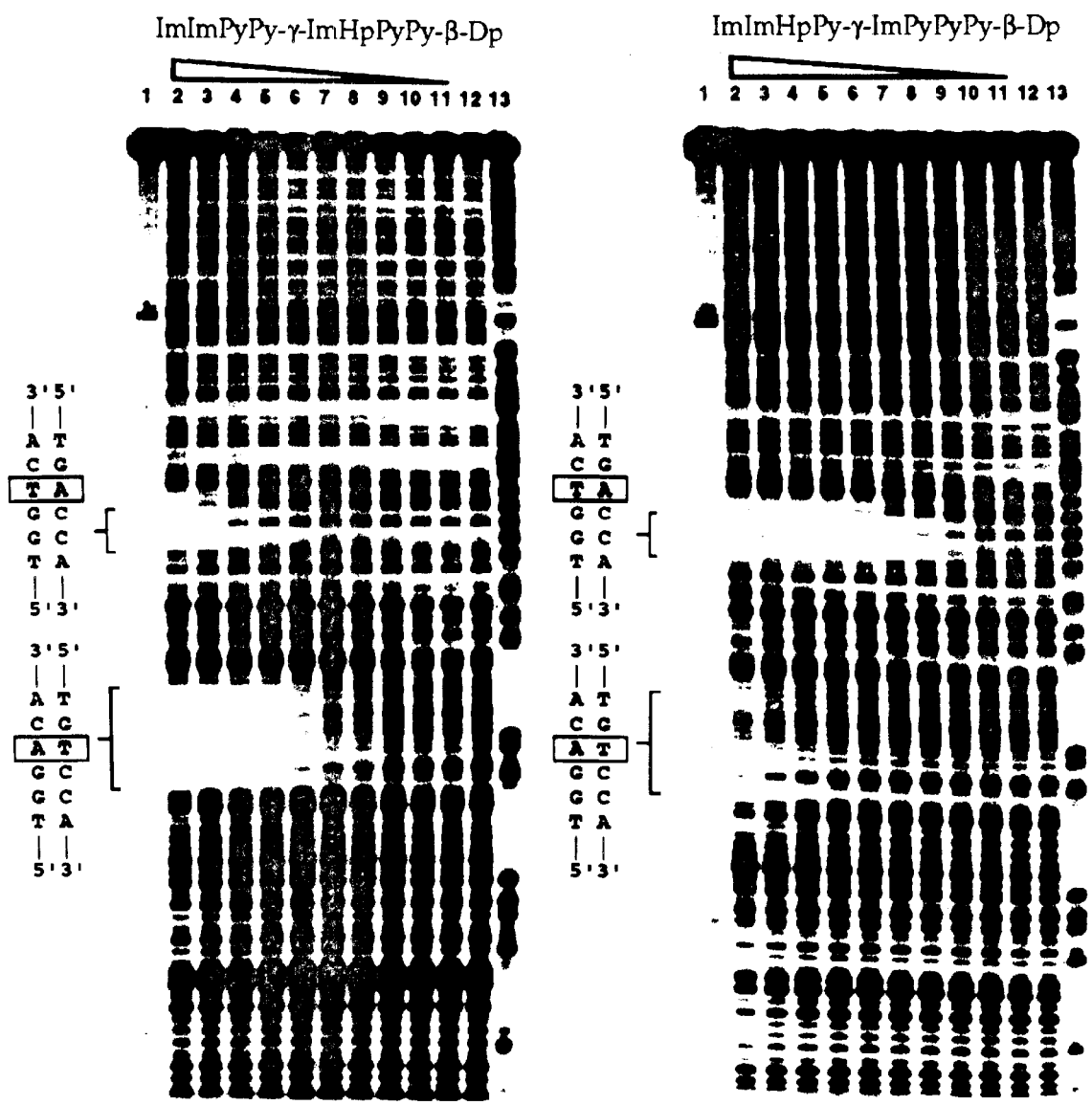
FIG. 3 illustrates the DNase footprint titration of compounds 2 and 3.

FIG. 3 shows quantitative DNase I footprint titration experiments with polyamides 2 and 3 on the 3'$^{32}$p labeled 250-bp pJK6 EcoRI/PvuII restriction fragment. Lane 1, intact DNA; lanes 2–11 DNase I digestion products in the presence of 100, 50, 20, 10, 5, 2, 1, 0.5, 0.2, 0.1 nM polyamide, respectively; lane 12, DNase I digestion products in the absence of polyamide; lane 13, adenine-specific chemical sequencing. Iverson, B. L. & Dervan, P. B. describes an adenine-specific DNA chemical sequencing reaction. *Methods Enzymol.* 15, 7823–7830 (1987). All reactions were done in a total volume of 400 μL. A polyamide stock solution or H$_2$O was added to an assay buffer containing radiolabeled restriction fragment, with the final solution conditions of 10 mM Tris-HCl, 10 mM KCl, 10 mM MgCl$_2$, 5 mM CaCl$_2$, pH 7.0. Solutions were allowed to equilibrate for 4–12 h at 22° C. before initiation of footprinting reactions. Footprinting reactions, separation of cleavage products, and data analysis were carried out as described. White, S., Baird, E. E. & Dervan, P. B. Effects of the A·T/T·A degeneracy of pyrrole-imidazole polyamide recognition in the minor groove of DNA. *Biochemistry* 35, 6147–6152 (1996).

Figure 4:
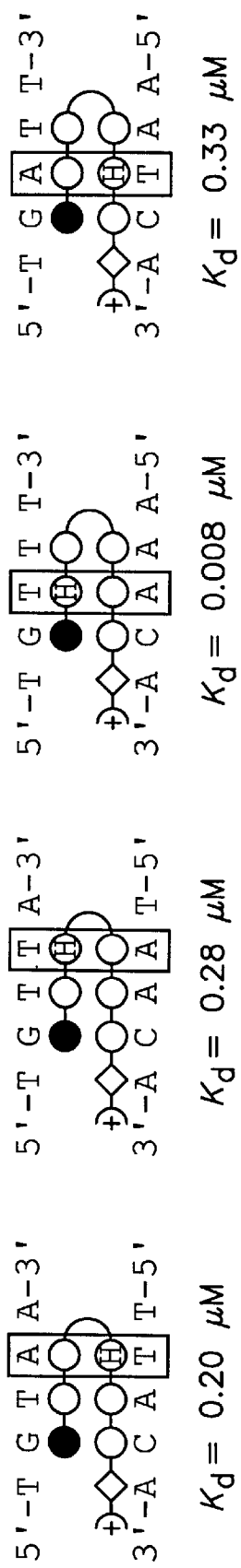
FIG. 4 illustrates a list of the structures of representative Hp containing polyamides.
Figure 4:
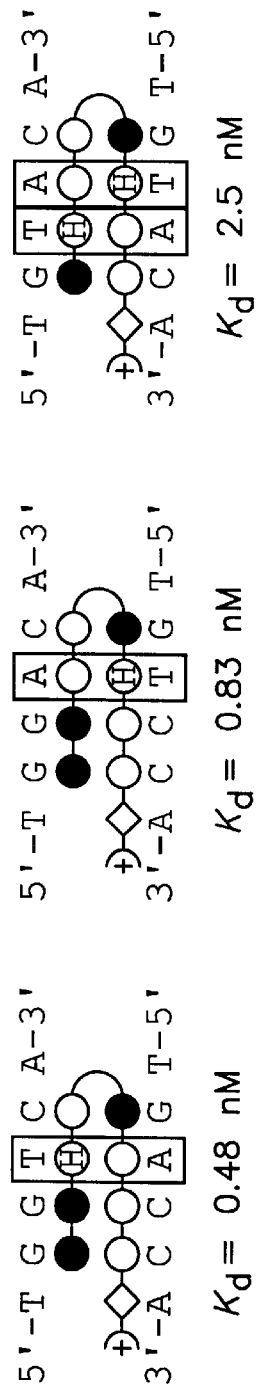
Figure 4:
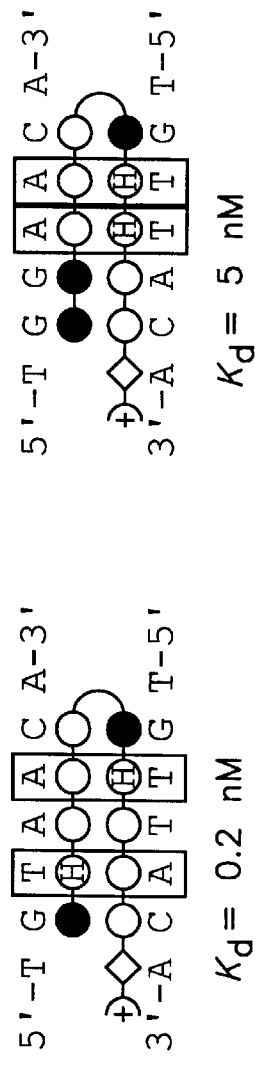

FIG. 4 shows the structure and equilibrium dissociation constant for numerous compounds of the present invention. Polyamides are shown in complex with their respective match site. Filled and unfilled circles represent imidazole (Im) and pyrrole (Py) rings, respectively; circles containing an H represent 3-hydroxypyrrole (Hp), the curved line connecting the polyamide subunits represents γ-aminobutyric acid (γ), the diamond represents β-alanine (β), and the + represents the positively charged dimethylaminopropylamide tail group (Dp). The equilibrium dissociation constants are the average values obtained from three DNase I footprint titration experiments. The standard deviation for each set is less than 15% of the reported number. Assays were carried out in the presence of 10 mM Tris·HCl, 10 mM KCl, 10 mM MgCl$_2$, and 5 mM CaCl$_2$ at pH 7.0 and 22° C.

Figure 5:
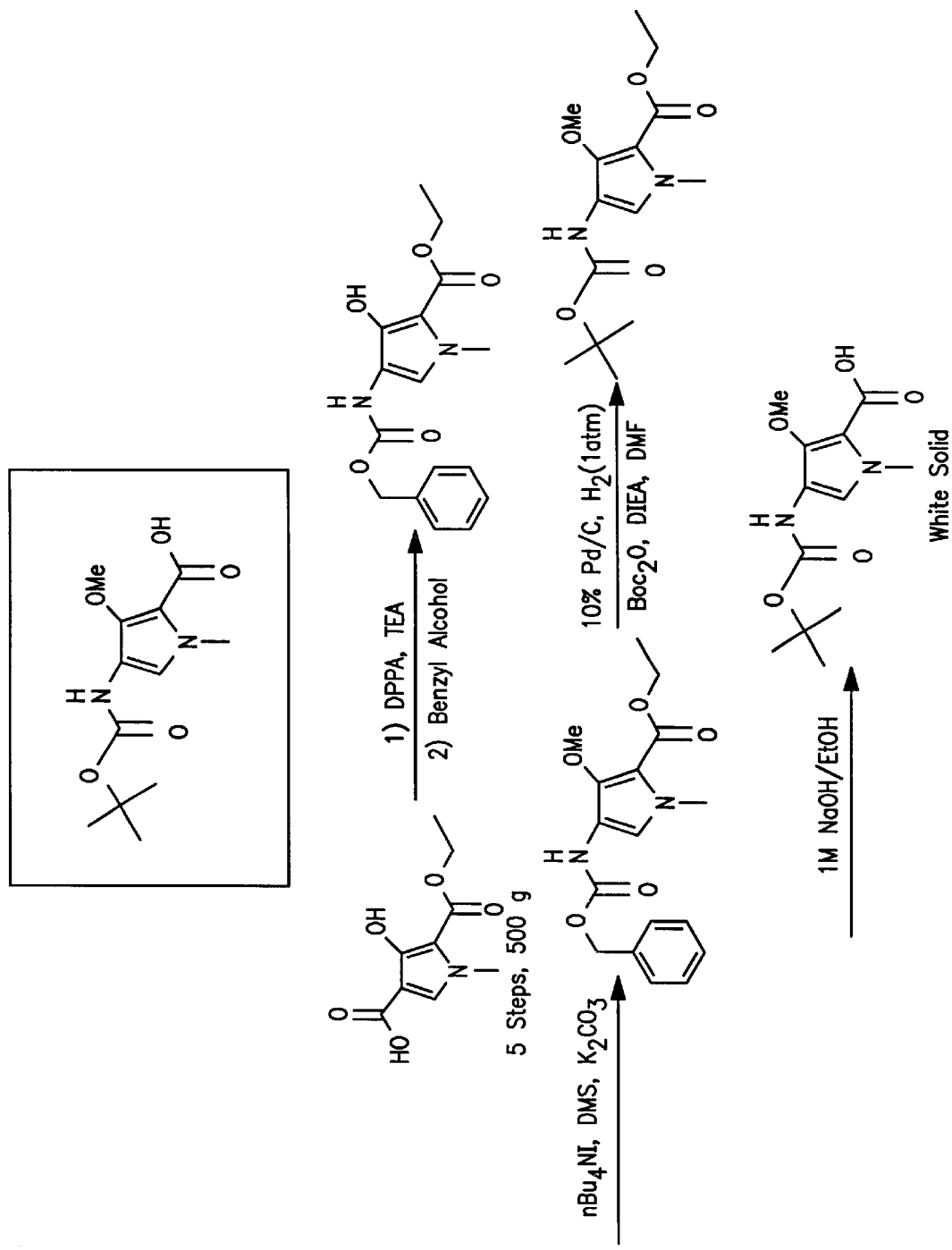
FIG. 5 illustrates the synthesis of a protected Hp monomer for solid phase synthesis.

FIG. 5 shows the synthetic scheme for 3-O-methyl-N-Boc protected pyrrole-2-carboxylate. The hydroxypyrrole monoester can be prepared in 0.5 kg quantity using published procedures on enlarged scale.

Figure 6:
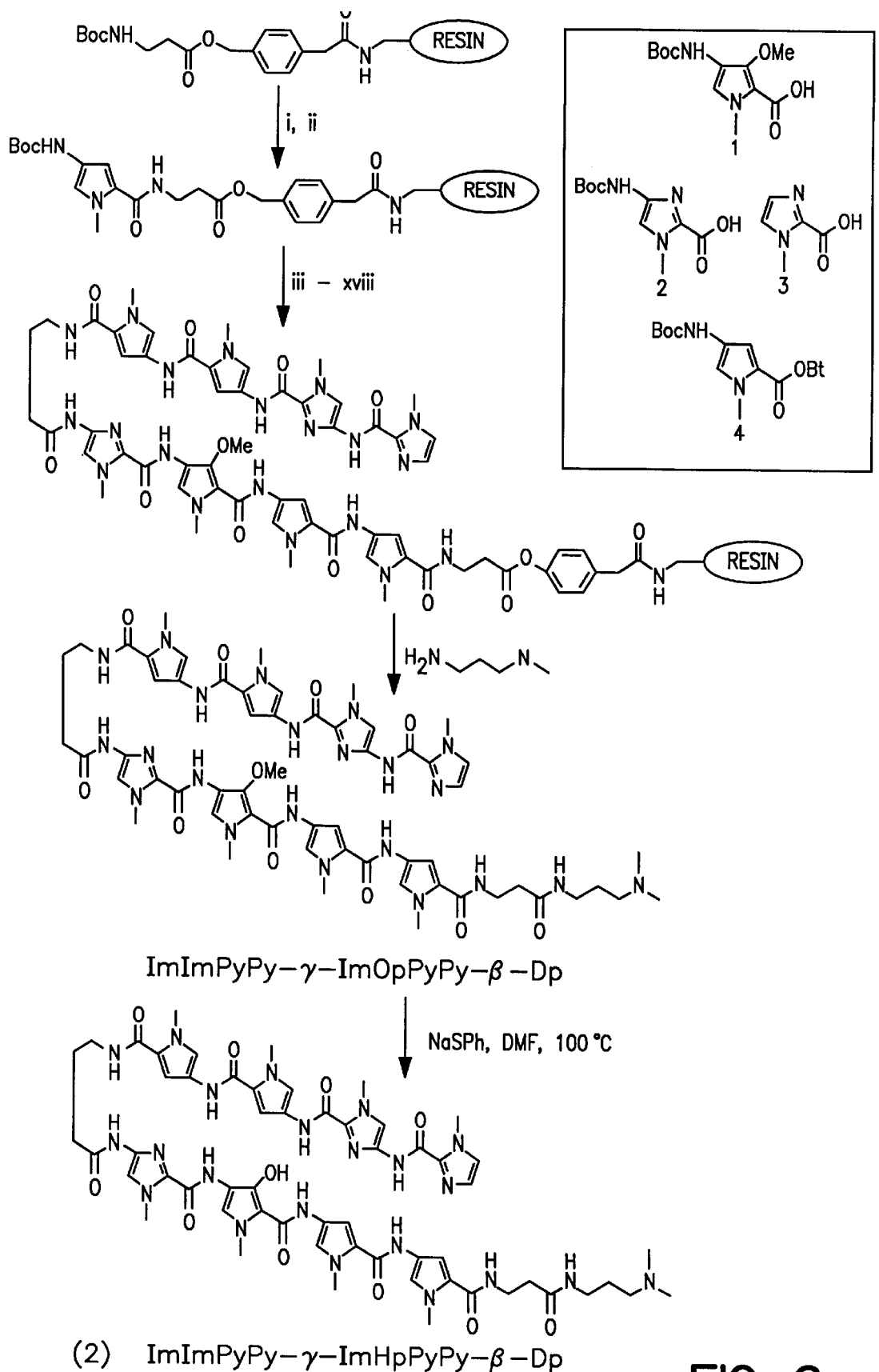
FIG. 6 illustrates the solid phase synthesis of polyamide 2.

FIG. 6 shows the solid phase synthetic scheme for ImImPyPy-γ-ImHpPyPy-β-Dp starting from commercially available Boc-β-Pam-Resin: (i) 80% TFA/DCM, 0.4 M PhSH; (ii) Boc-Py-OBt, DIEA, DMF; (iii) 80% TFA/DCM, 0.4 M PhSH; (iv) Boc-Py-OBt, DIEA, DMF; (v) 80% TFA/DCM, 0.4 M PhSH; (vi) Boc-3-OMe-Py-OH, HBTU, DMF, DIEA; (vii) 80% TFA/DCM, 0.4 M PhSH; (viii) Boc-Im-OH, DCC, HOBt; (ix) 80% TFA/DCM, 0.4 M PhSH; (x) Boc-γ-aminobutyric acid, DIEA, DMF; (xi) 80% TFA/DCM, 0.4 M PhSH; (xii) Boc-Py-OBt, DIEA, DMF; (xiii) 80% TFA/DCM, 0.4 M PhSH; (xiv) Boc-Py-OBt, DMF, DIEA; (xv) 80% TFA/DCM, 0.4 M PhSH; (vxi) Boc-Im-OH, DCC, HOBt (xvii) 80% TFA/DCM, 0.4 M PhSH; (xviii) imidazole-2-carboxylic acid, HBTU, DIEA; (xviv) dimethylaminopropylamine, 55° C., 18 h. Purification by reversed phase HPLC provides ImImPyPy-γ-ImOpPyPy-β-Dp. (Op=3-methoxypyrrole). Treatment of the 3-methyoxypyrrole polyamide with thiophenol, NaH, DMF, at 100° C. for 120 min provides polyamide 2 after reverse phase HPLC purification.

Figure 7A:
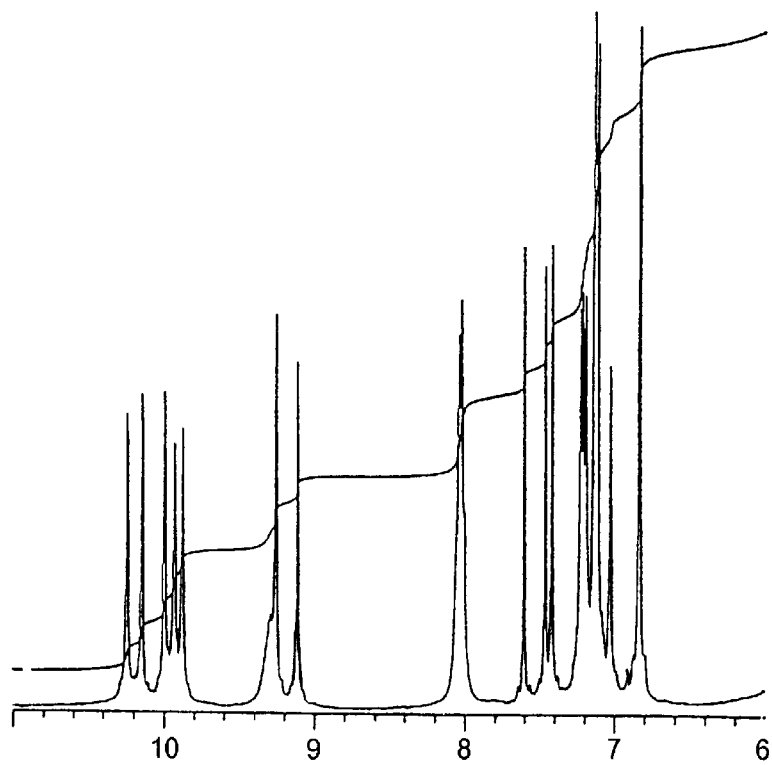
FIG. 7 illustrates the 1H-NMR characterization of polyamide 2.
Figure 7B:
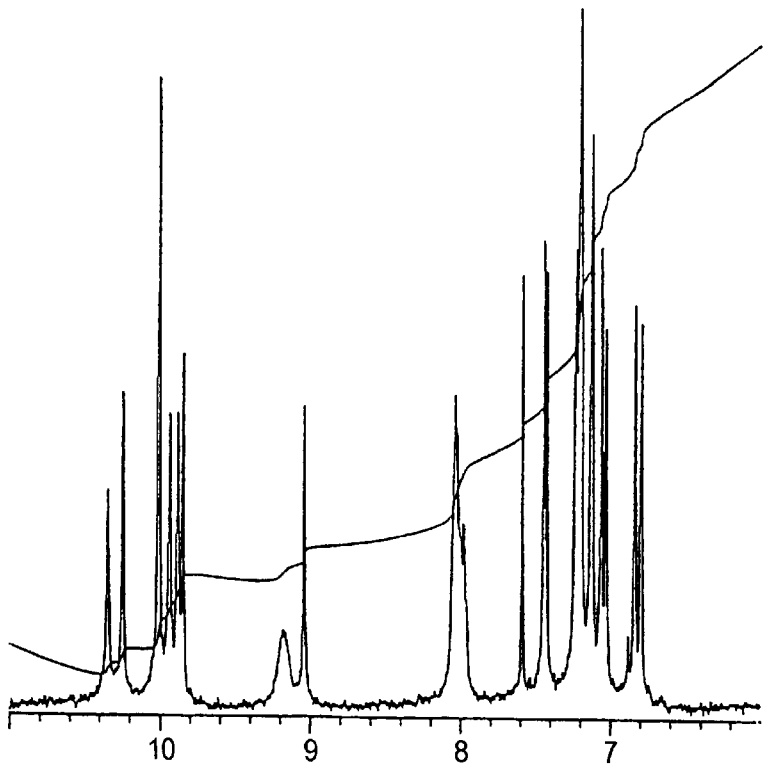

FIG. 7 shows the aromatic region from 7–11 ppm for the 1H-NMR spectrum determined at 300 MHz for ImImPyPy-γ-ImOpPyPy-β-Dp and ImImPyPy-γ-ImHpPyPy-β-Dp. This region of the spectrum may be used to determine compound identity and purity.

Figure 8A:
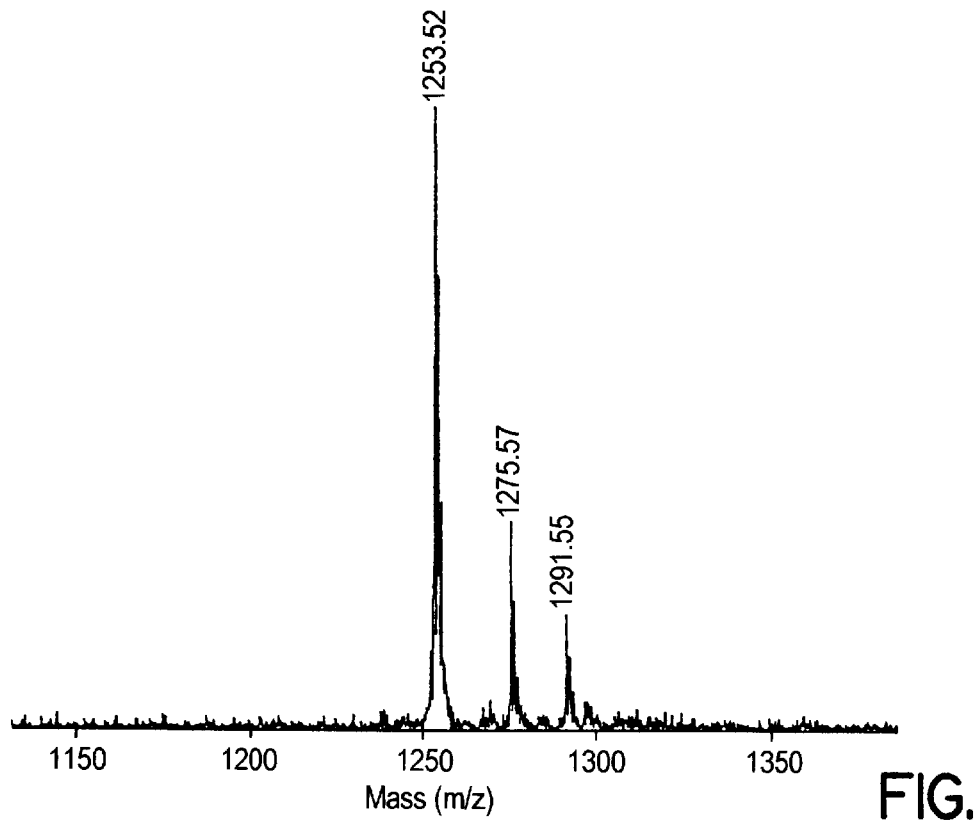
FIG. 8 illustrates the Mass spectral characterization of polyamide 2.
Figure 8B:
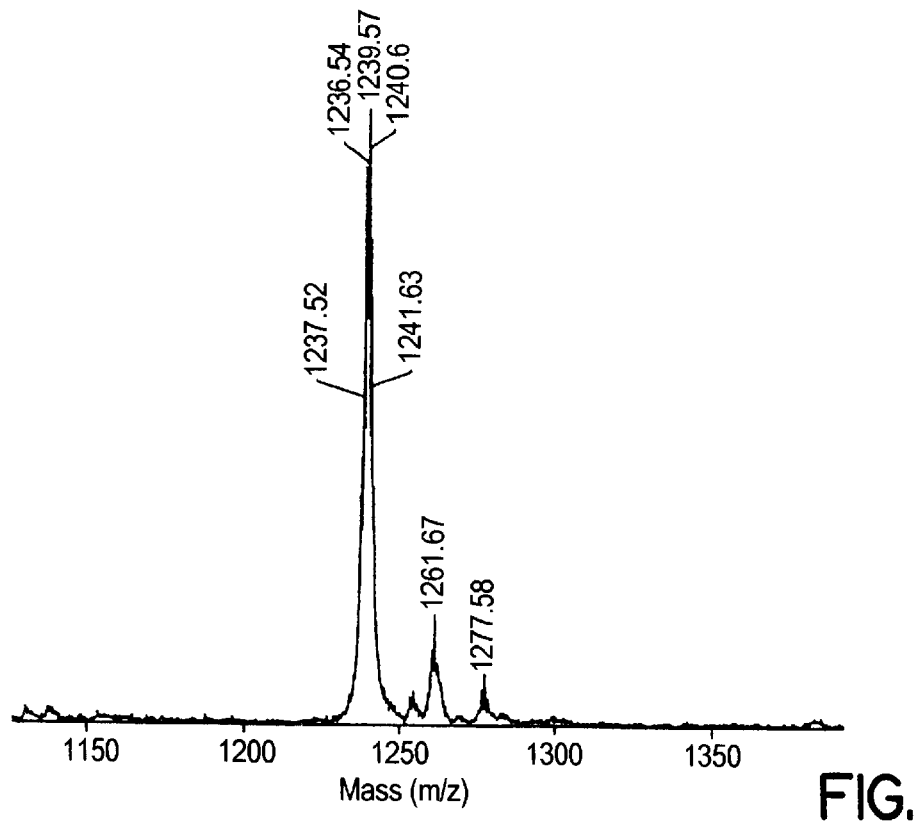

FIG. 8 shows the MALDI-TOF mass spectrum determined in positive ion mode with a monoisotopic detector for the polyamides for ImImPyPy-γ-hmOpPyPy-β-Dp and ImImPyPy-γ-ImHpPyPy-β-Dp. This spectrum may be used to determine compound identity and purity.

Figure 9A:
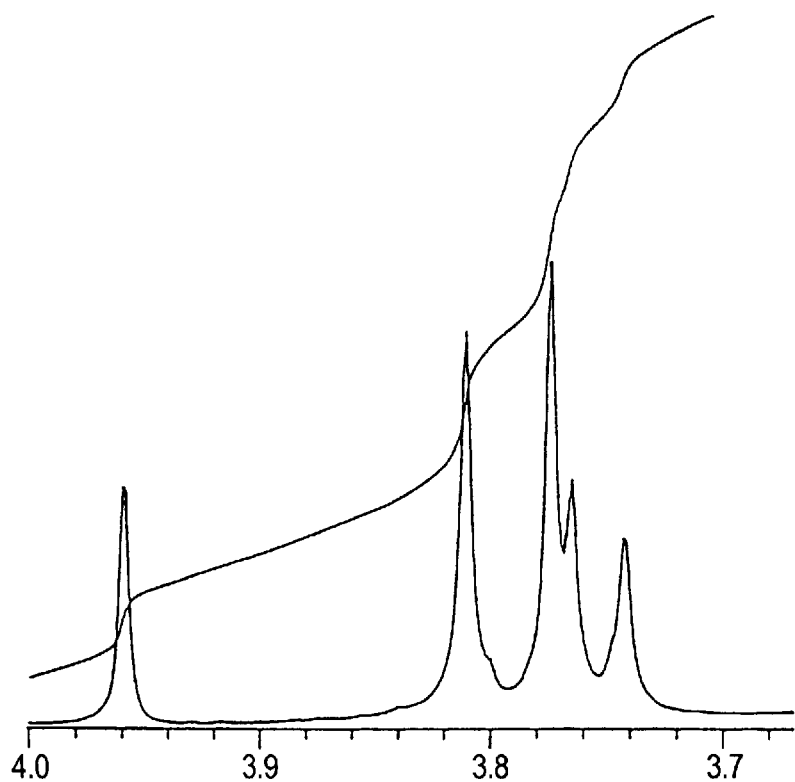
FIG. 9 illustrates 1H-NMR characterization of synthesis purity.
Figure 9B:
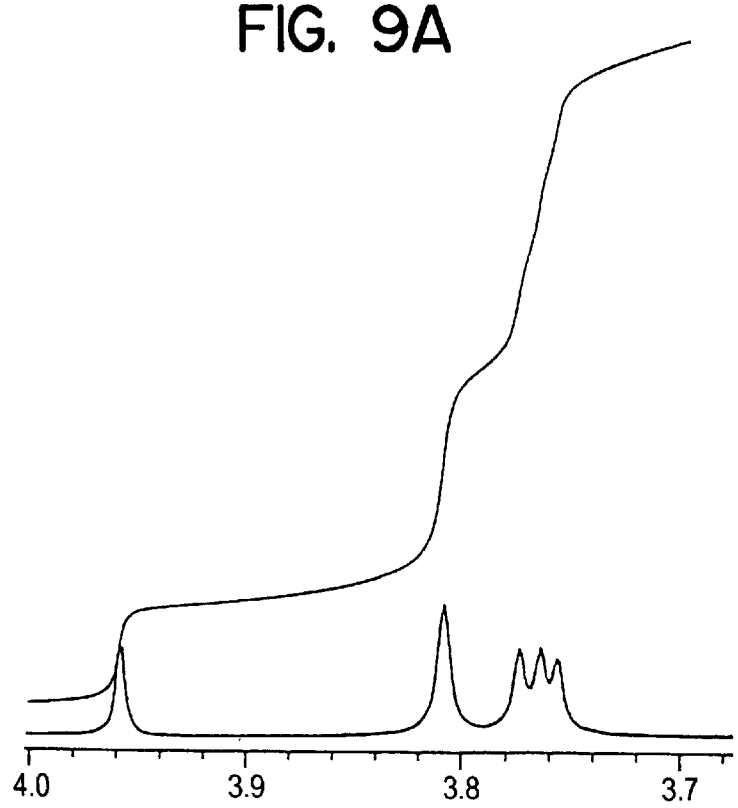

FIG. 9 shows the methyl group region from 3.5–4.0 ppm for the 1H-NMR spectrum determined at 300 MHz for ImPyPy-γ-OpPyPy-β-Dp and ImPyPy-γ-HpPyPy-β-Dp. This region of the spectrum may be used to directly follow the progress for conversion of 3-methoxypyrrole to 3-hydroxypyrrole.

Figure 10:
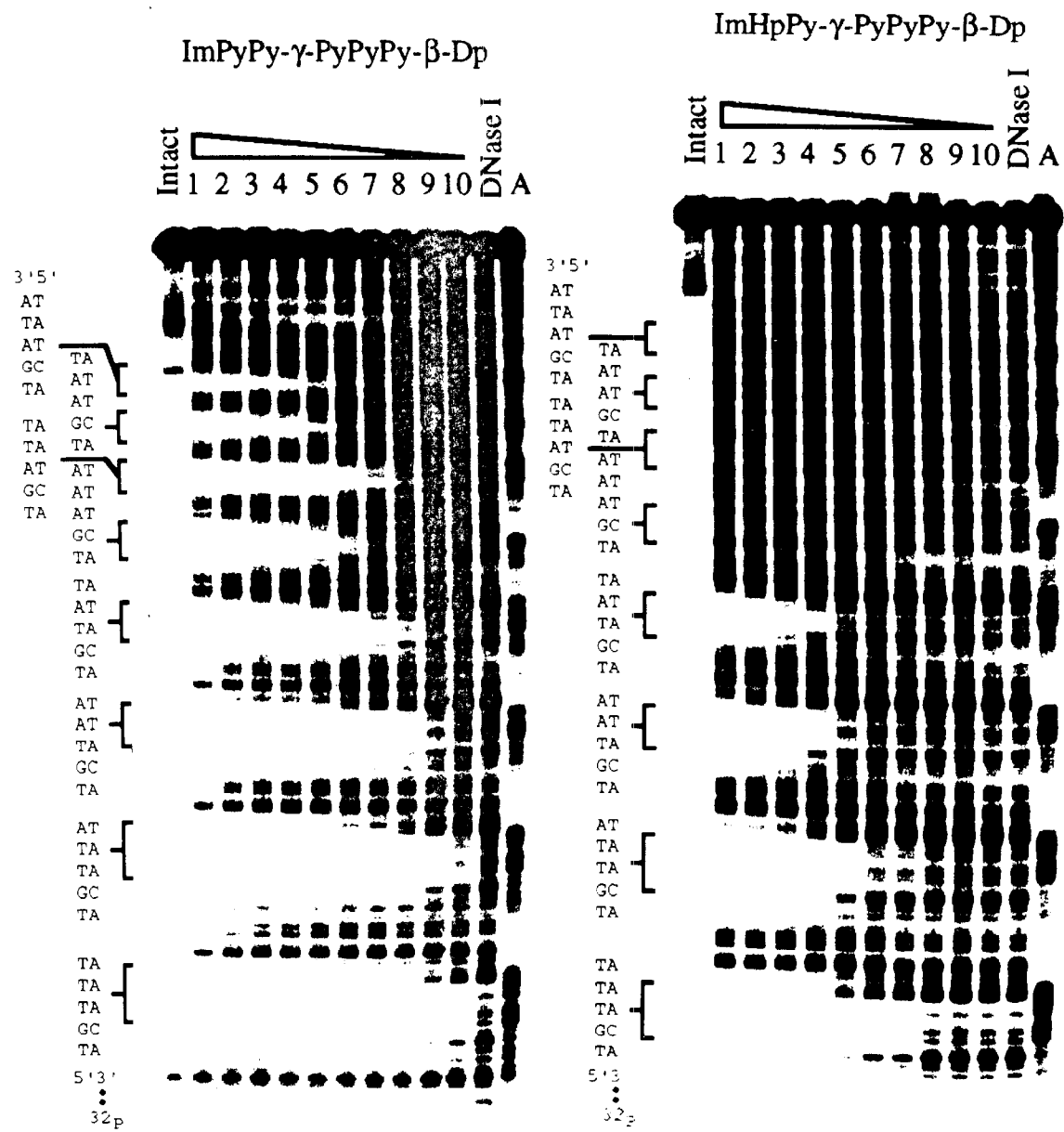
FIG. 10 illustrates DNaseI footprint titration experiment.

FIG. 10 shows quantitative DNase I footprint titration experiments with the polyamides ImPyPy-γ-PyHpPy-β-Dp and ImHpPy-γ-PyPyPy-β-Dp on the 3'-$^{32}$p labeled 370-bp pDEH1 EcoRI/PvuII restriction fragment. Intact lane, labeled restriction fragment no polyamide or DNase I added; lanes 1–10, DNase I digestion products in the presence of 10 μM, 5 μM, 2 μM, 1 μM, 500 nM, 200 nM, 100 nM, 50 nM, 20 nM, 10 nM ImPyPy-γ-PyPyPy-β-Dp, respectively or 1 μM, 500 nM, 200 nM, 100 nM, 50 nM, 20 nM, 10 nM, 5 nM, 2 nM, 1 nM ImHpPy-γ-PyPyPy-β-Dp, respectively; DNase I lane, DNase I digestion products in the absence of polyamide; A lane, adenine-specific chemical sequencing. Iverson, B. L. & Dervan, P. B. describes an adenine-specific DNA chemical sequencing reaction. *Methods Enzymol.* 15, 7823–7830 (1987). All reactions were done in a total volume of 40 μL. A polyamide stock solution or $H_2O$ was added to an assay buffer containing radiolabeled restriction fragment, with the final solution conditions of 10 mM Tris-HCl, 10 mM KCl, 10 mM $MgCl_2$, 5 mM $CaCl_2$, pH 7.0. Solutions were allowed to equilibrate for 4–12 h at 22° C. before initiation of footprinting reactions. Footprinting reactions, separation of cleavage products, and data analysis were carried out as described. White, S., Baird, E. E. & Dervan, P. describe the pairing rules for recognition in the minor groove of DNA by pyrrole-imidazole polyamides. *Chemistry & Biology* 4, 569–578 (1997).

Figure 11:
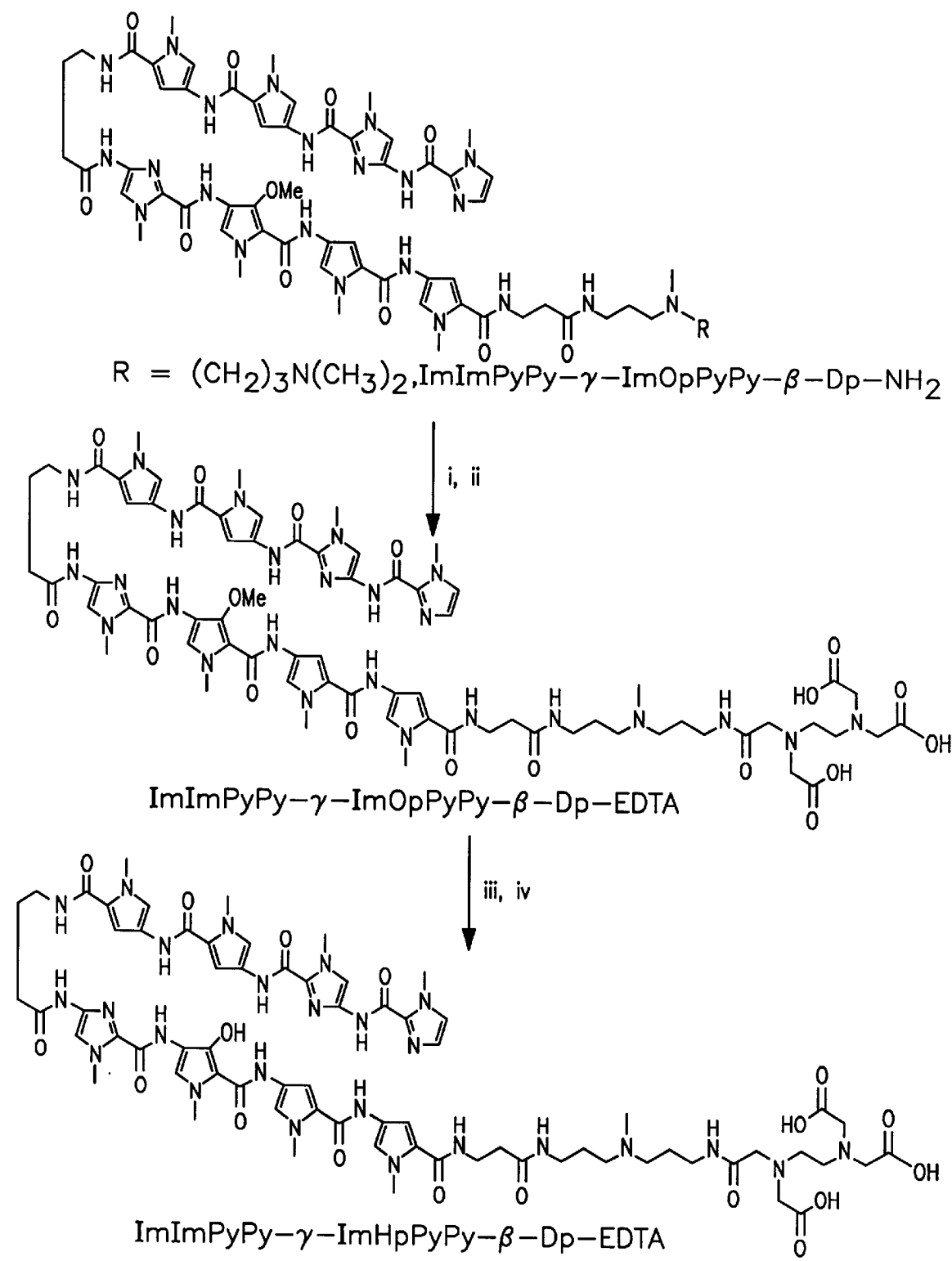
FIG. 11 illustrates the synthesis of bifunctional conjugate of polyamide 2.

FIG. 11 shows the synthesis of a bifunctional polyamide which incorporates the Hp/Py pair. Treatment of a sample of ImImPyPy-γ-ImHpPyPy-β-Pam-resin (see FIG. 6) with 3,3'-diamino-N-methyldipropylamine, 55° C., 18 h followed by reverse phase HPLC purification provides the Op polyamide with a free primary amine group which can be coupled to an activated carboxylic acid derivative. Treatment with (i) EDTA-dianhydride, DMSO/NMP, DIEA, 55° C.; (ii) 0.1M NaOH, followed by reverse phase HPLC purification provides the Op-Py-Im-polyamide-EDTA conjugate. Treatment of the 3-methyoxypyrrole polyamide with thiophenol, NaH, DMF, at 100° C. for 120 min provides polyamide 2 after reverse phase HPLC purification.

Figure 12A:
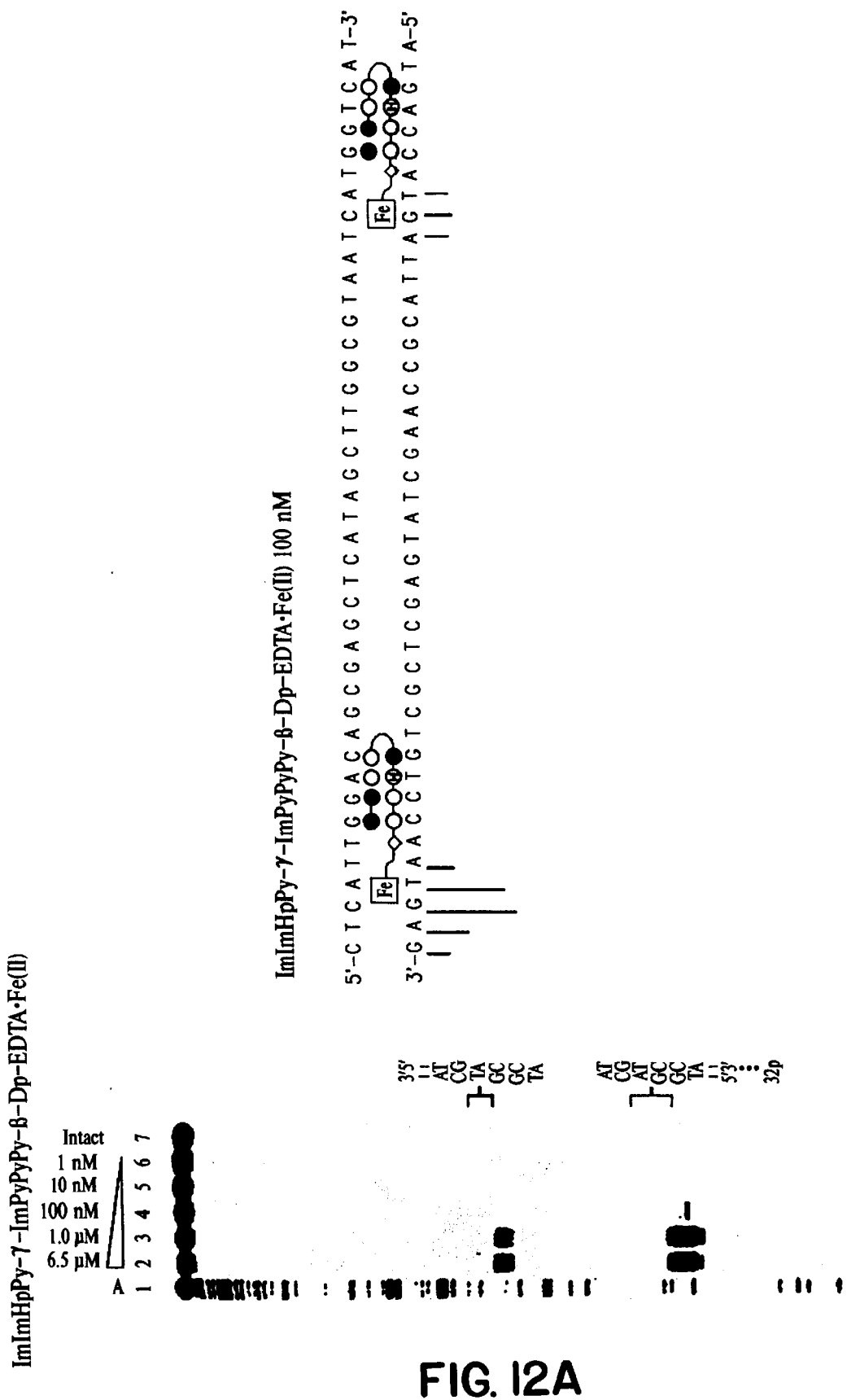
FIG. 12 illustrates affinity cleaving evidence for oriented hairpin formation.
Figure 12B:

FIG. 12 shows the determination of the binding orientation of hairpin polyamides ImImPyPy-γ-ImHpPyPy-β-Dp-EDTA·Fe(II) 2-E·Fe(II) and ImImHpPy-γ-ImPyPyPy-β-Dp-EDTA·Fe(II) 3-E·Fe(II) by affinity cleaving footprint titration. Top and bottom left: Affinity cleavage experiments on a $3'^{32}p$ labeled 250-bp pJK6 EcoRI/Pvu II restriction fragment. The 5'-TGGACA-3' and 5'-TGGTCA-3' sites are shown on the right side of the autoradiogram. Top left: lane 1, adenine-specific chemical sequencing reaction; lanes 2–6, 6.5 μM, 1.0 μM, 100 nM, 10 nM, 1 nM polyamide 2-E·Fe (II); lane 7, intact restriction fragment, no polyamide added. Bottom left: lane 1, A reaction; lanes 2–6, 8.5 nM, 1.0 μM, 100 nM, 10 μM, 1 nM polyamide 3-E·Fe(II); lane 7, intact DNA. All reactions were carried out in a total volume of 40 μL. A stock solution of polyamide or $H_2O$ was added to a solution containing 20 kcpm labeled restriction fragment, affording final solution conditions of 25 mM Tris-Acetate, 20 mM NaCl, 100 μM/bp calf thymus DNA, at pH 7.0. Solutions were allowed to equilibrate for a minimum of 4 h at 22°K before initiation of reactions. Affinity cleavage reactions were carried out as described White, S., Baird, E. E. & Dervan, P. B. Effects of the A·T/T·A degeneracy of pyrrole-imidazole polyamide recognition in the minor groove of DNA. *Biochemistry* 35, 6147–6152 (1996). Top and bottom right: Affinity cleavage patterns of 2-E·Fe(II) and 3-E·Fe(II) at 100 nM bound to 5'-TGGACA-3' and 5'-TGGTCA-3'. Bar heights are proportional to the relative cleavage intensities at each base pair. Shaded and nonshaded circles denote imidazole and pyrrole carboxamides, respectively. Nonshaded diamonds represent the β-alanine moiety. A curved line represents the γ-aminobutyric acid, and the + represents the positively charged dimethylaminopropylamide tail group. The boxed Fe denotes the EDTA·Fe(II) cleavage moiety.

Figure 13:
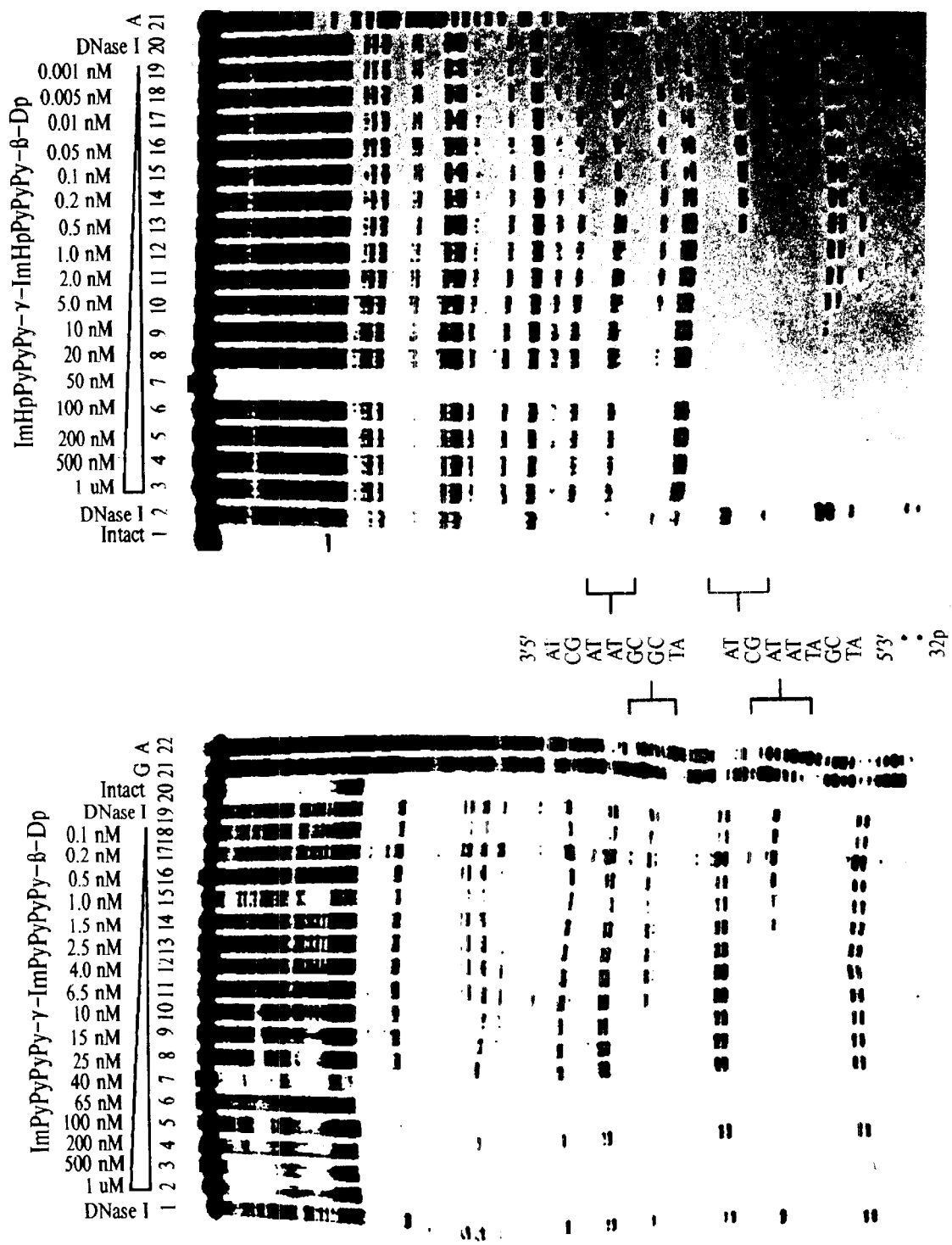
FIG. 13 illustrates increased sequence specificity of Hp/Py containing polyamides.

FIG. 13 shows quantitative DNase I footprint titration experiments with the polyamides ImPyPyPyPy-γ-ImPyPyPyPy-β-Dp and ImHpPyPyPy-γ-ImHpPyPyPy-β-Dp on the $3'^{32}P$ labeled 252-bp pJK7 EcoRI/Pvu II restriction fragment. For ImPyPyPyPy-γ-ImPyPyPyPy-β-Dp gel (left): lane 1, DNase I digestion products in the absence of polyamide; lanes 2–18, DNase I digestion products in the presence of 1.0 μM, 500 nM, 200, 100, 65, 40, 25, 15, 10, 6.5, 4.0, 2.5, 1.5, 1.0, 0.5, 0.2, 0.1 nM polyamide; lane 19, DNase I digestion products in the absence of polyamide; lane 20, intact restriction fragment; lane 21, guanine-specific chemical sequencing reaction; lane 22, adenine-specific chemical sequencing reaction. For ImHpPyPyPy-γ-ImHpPyPyPy-β-Dp gel (right): lane 1, intact DNA; lane 2, DNase I digestion products in the absence of polyamide; lanes 3–19, 1.0 μM, 500 nM, 200, 100, 50, 20, 10, 5, 2, 1, 0.5, 0.2. 0.1, 0.05, 0.01, 0.005, 0.001 nM polyamide; lane 20, DNase I digestion products in the absence of polyamide; lane 21, A reaction. All reactions were done in a total volume of 400 μL. A polyamide stock solution or $H_2O$ was added to an assay buffer containing radiolabeled restriction fragment, with the final solution conditions of 10 mM Tris-HCl, 10 mM KCl, 10 mM $MgCl_2$, 5 mM $CaCl_2$, pH 7.0. Solutions were allowed to equilibrate for 4–12 h at 22° C. before initiation of footprinting reactions. Footprinting reactions, separation of cleavage products, and data analysis were carried as described. White, S., Baird, E. E. & Dervan, P. B. Effects of the A·T/T·A degeneracy of pyrrole-imidazole polyamide recognition in the minor groove of DNA. *Biochemistry* 35, 6147–6152 (1996).

Figure 14:
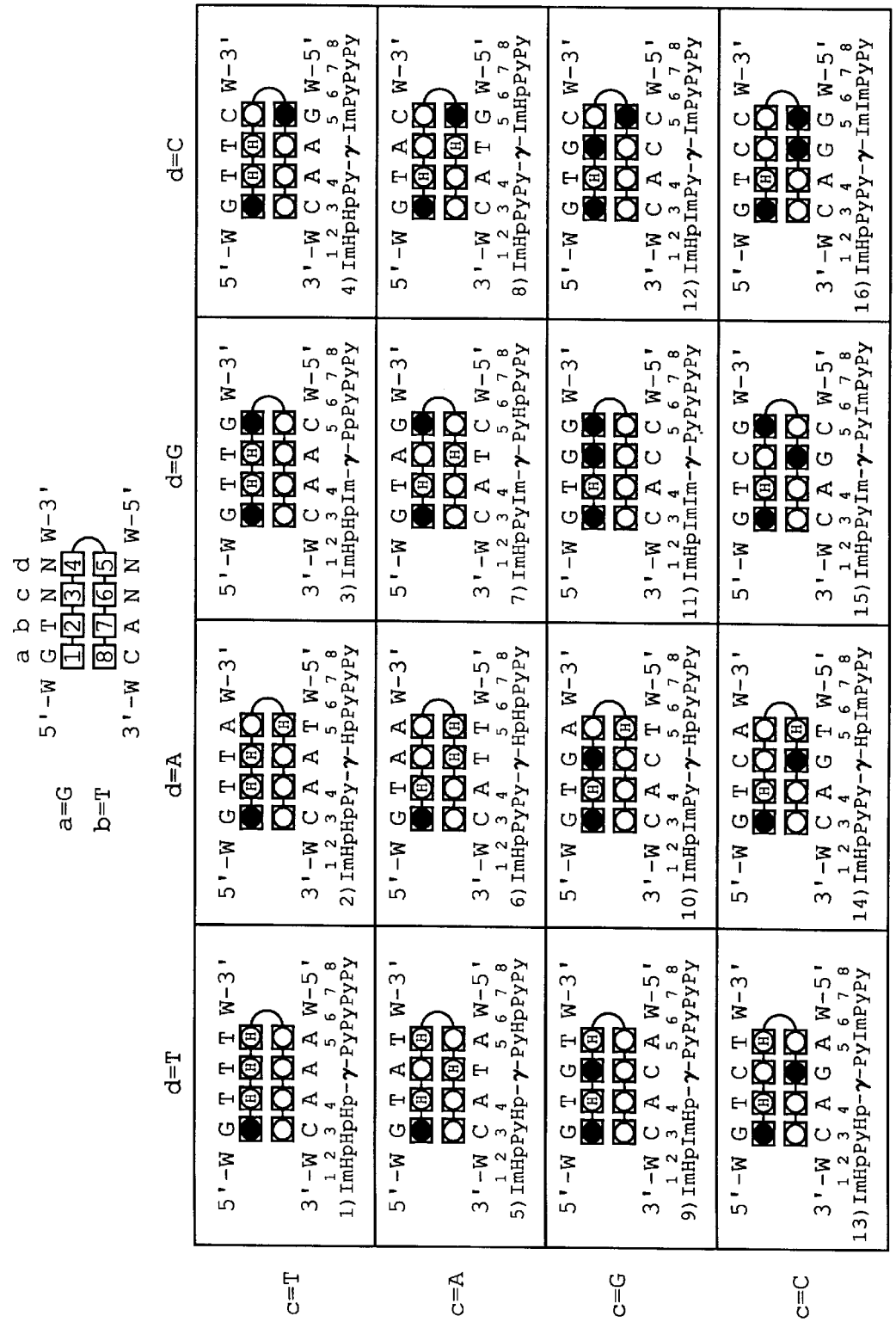
FIG. 14 illustrates 8-ring hairpin polyamides which target 5'-WGTNNW-3' sites.

FIG. 14 shows the 8-ring Hp-Py-Im-polyamide hairpins described by the pairing code of the present invention. The eight ring hairpin template is shown at the top. A polyamide having the formula $X_1X_2X_3X_{4-\gamma}-X_5X_6X_7X_8$ wherein γ is the —NH—$CH_2$—$CH_2$—$CH_2$—CONH— hairpin linkage derived from 7-aminobutyric acid or a chiral hairpin linkage derived from R-2,4-diaminobutyric acid; $X_4/X_5$, $X_3/X_6$, $X_2/X_7$, and $X_1/X_8$ represent carboxamide binding pairs which bind the DNA base pairs. The minor groove sequence to be bound is represented as 5'-WGTNNW-3', where the 5'-GTNN-3' core sequence is defined as position a, b, c, and d (W=A or T, N=A, G, C, or T). A linear sequence of aromatic amino acids fills the hairpin template in order to satisfy the ring pairing requirements to correspond to the DNA base pairs in the minor groove to be bound. The ring pairing code as applied is listed in Table 2. The 16 unique hairpin polyamides which target 16 5'-WGTNNW-3' sequences are drawn as binding models where filled and unfilled circles represent imidazole and pyrrole rings respectively; circles containing an H represent 3-hydroxypyrrole, and the curved line connecting the polyamide subunits represents γ-aminobutyric acid.

Figure 15:
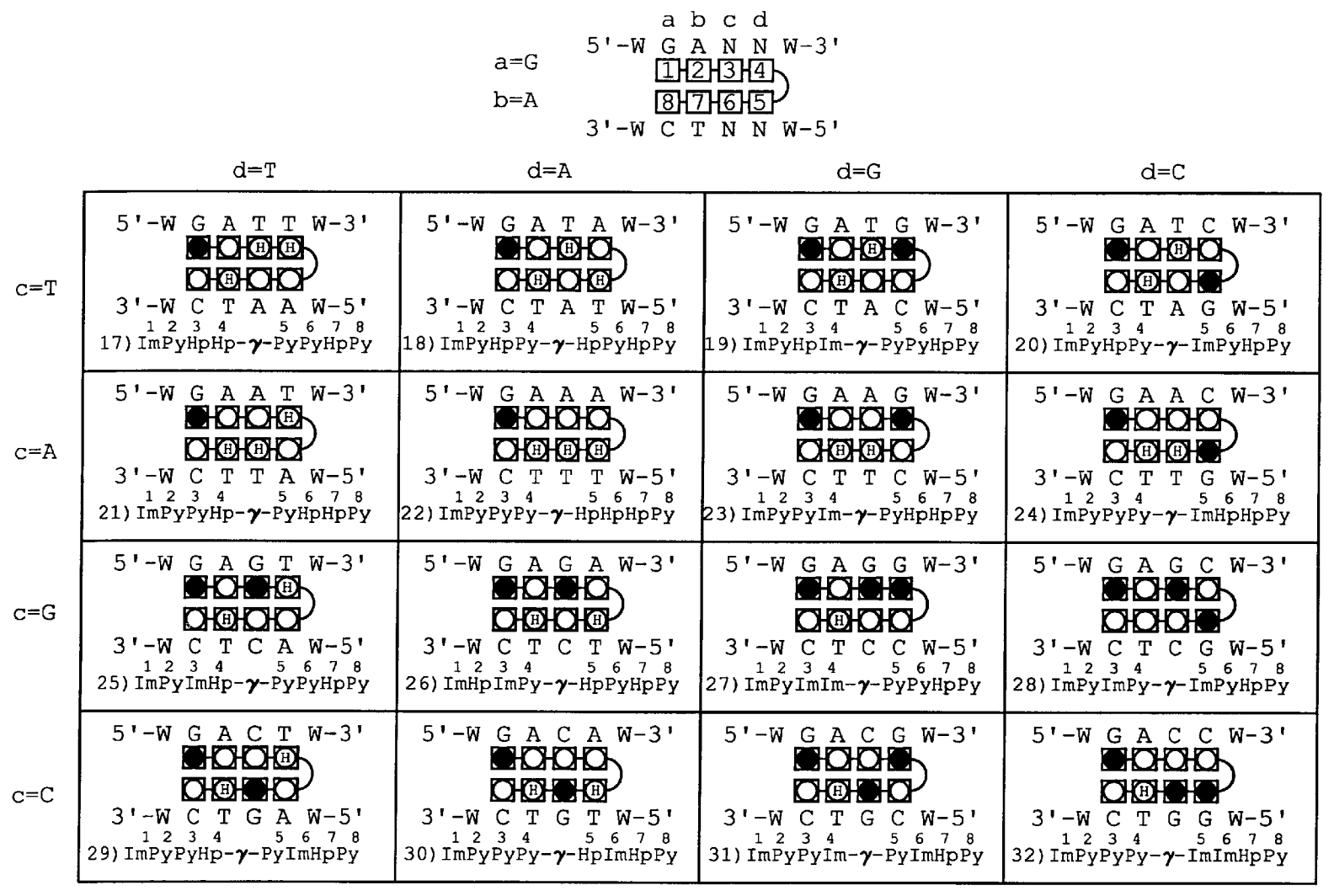

FIG. 15 shows the 8-ring Hp-Py-Im-polyamide hairpins described by the pairing code of the present invention. The eight ring hairpin template is shown at the top. A polyamide having the formula $X_1X_2X_3X_{4-\gamma}-X_5X_6X_7X_8$ wherein γ is the —NH—$CH_2$—$CH_2$—$CH_2$—CONH— hair linkage derived from γ-aminobutyric acid or a chiral hairpin linkage derived from R-2,4-diaminobutyric acid; $X_4/X_5$, $X_3/X_6$, $X_2/X_7$, and $X_1/X_8$ represent carboxamide binding pairs which bind the DNA base pairs. The minor groove sequence to be bound is represented as 5'-WGANNW-3', where the 5'-GANN-3' core sequence is defined as position a, b, c, and d (W=A or T, N=A, G, C, or T). A linear sequence of aromatic amino acids fills the hairpin template in order to satisfy the ring pairing requirements to correspond to the DNA base pairs in the minor groove to be bound. The ring pairing code as applied is listed in Table 2. The 16 unique hairpin polyamides which target 16 5'-WGANNW-3' sequences are drawn as binding models where filled and unfilled circles represent imidazole and pyrrole rings respectively; circles containing an H represent 3-hydroxypyrrole, and the curved line connecting the polyamide subunits represents γ-aminobutyric acid.

Figure 16:
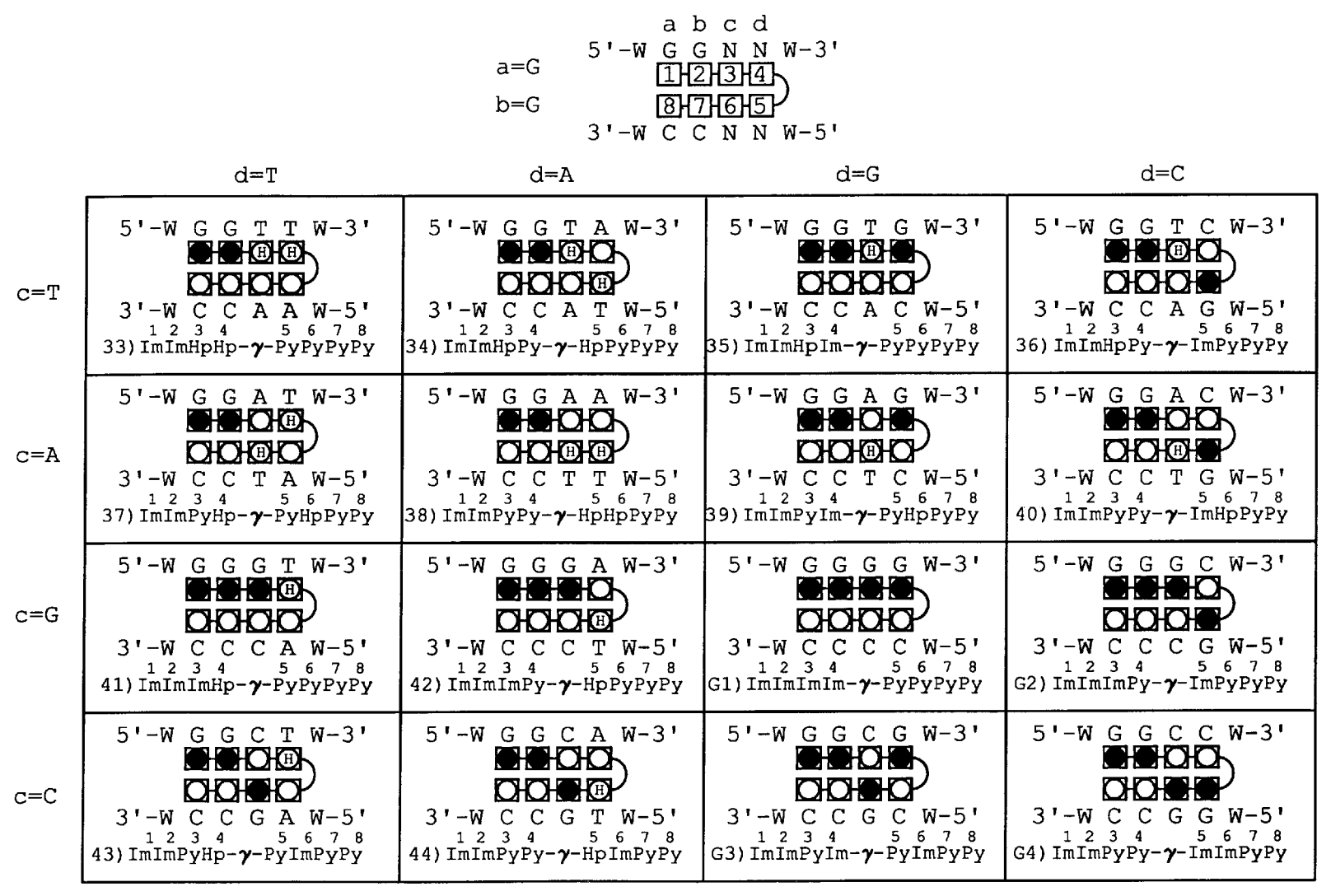

FIG. 16 shows the 8-ring Hp-Py-Im-polyamide hairpins described by the pairing code of the present invention. The eight ring hairpin template is shown at the top. A polyamide having the formula $X_1X_2X_3X_{4-\gamma}-X_5X_6X_7X_8$ wherein γ is the —NH—CH$_2$—CH$_2$—CH$_2$—CONH— hair linkage derived from γ-aminobutyric acid or a chiral hairpin linkage derived from R-2,4-diaminobutyric acid; $X_4/X_5$, $X_3/X_6$, $X_2/X_7$, and $X_1/X_8$ represent carboxamide binding pairs which bind the DNA base pairs. The minor groove sequence to be bound is represented as 5'-WGGNNW-3', where the 5'-GGNN-3' core sequence is defined as position a, b, c, and d (W=A or T, N=A, G, C, or T). A linear sequence of aromatic amino acids fills the hairpin template in order to satisfy the ring pairing requirements to correspond to the DNA base pairs in the minor groove to be bound. The ring pairing code as applied is listed in Table 2. The 16 unique hairpin polyamides which target 16 5'-WGGNNW-3' sequences are drawn as binding models where filled and unfilled circles represent imidazole and pyrrole rings respectively; circles containing an H represent 3-hydroxypyrrole, and the curved line connecting the polyamide subunits represents γ-aminobutyric acid.

Figure 17:
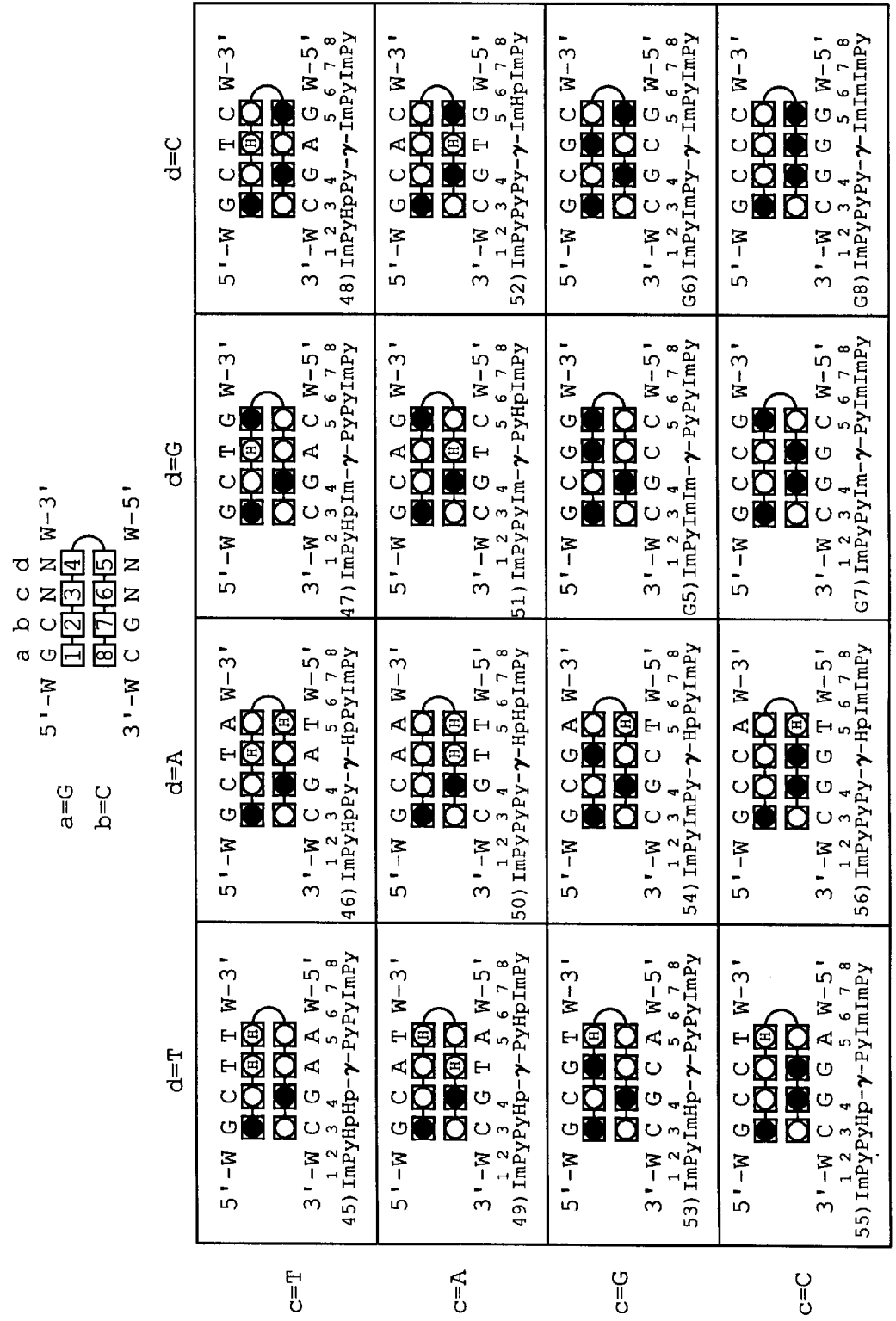
FIG. 17 illustrates 8-ring hairpin polyamides which target 5'-WGCNNW-3' sites.

FIG. 17 shows the 8-ring Hp-Py-Im-polyamide hairpins described by the pairing code of the present invention. The eight ring hairpin template is shown at the top. A polyamide having the formula $X_1X_2X_3X_{4-\gamma}-X_5X_6X_7X_8$ wherein γ is the —NH—CH$_2$—CH$_2$—CH$_2$—CONH— hairpin linkage derived from γ-aminobutyric acid or a chiral hairpin linkage derived from R-2,4-diaminobutyric acid; $X_4/X_5$, $X_3/X_6$, $X_2/X_7$, and $X_1/X_8$ represent carboxamide binding pairs which bind the DNA base pairs. The minor groove sequence to be bound is represented as 5'-WGCNNW-3', where the 5'-GCNN-3' core sequence is defined as position a, b, c, and d (W=A or T, N=A, G, C, or T). A linear sequence of aromatic amino acids fills the hairpin template in order to satisfy the ring pairing requirements to correspond to the DNA base pairs in the minor groove to be bound. The ring pairing code as applied is listed in Table 2. The 16 unique hairpin polyamides which target 16 5'-WGCNNW-3' sequences are drawn as binding models where filled and unfilled circles represent imidazole and pyrrole rings respectively; circles containing an H represent 3-hydroxypyrrole, and the curved line connecting the polyamide subunits represents γ-aminobutyric acid.

Four-ring polyamide subunits, covalently coupled to form eight-ring hairpin structures, bind specifically to 6-bp target sequences at subnanomolar concentrations. Trauger, J. W., Baird, E. E. & Dervan, P. B. describe the recognition of DNA by designed ligands at subnanomolar concentrations. *Nature* 382, 559–561 (1996); Swalley, S. E., Baird, E. E. & Dervan, P. B. describe the discrimination of 5'-GGGG-3', 5'-GCGC-3', and 5'-GGCC'3' sequences in the minor groove of DNA by eight-ring hairpin polyamides. *J. Am. Chem. Soc.* 119, 6953–6961 (1997). The DNA-binding affinities of three eight-ring hairpin polyamides shown in FIG. 1 as compound 1, 2, and 3 containing pairings of Im/Py, Py/Im opposite G·C, C·G and either Py/Py, Hp/Py, or Py/Hp at a common single point opposite T·A and A·T has been determined. Equilibrium dissociation constants ($K_d$) for ImImPyPy-γ-ImPyPyPy-β-Dp 1, ImImPyPy-γ-ImHpPyPy-β-Dp 2, ImImHpPy-γ-ImPyPyPy-β-Dp 3 of FIG. 1 are shown in Table 1. Brenowitz, M., Senear, D. F., Shea, M. A. & Ackers, G. K. describe a quantitative DNase footprint titration method for studying protein-DNA interactions. *Methods Enzymol.* 130, 132–181 (1986); The $K_d$ values were determined by quantitative DNase I footprint titration experiments: on a 3' $^{32}$P-labeled 250-bp DNA fragment containing the target sites, 5'-TGGACA-3' and 5'-TGGTCA-3' which differ by a single A·T base pair in the fourth position. The DNase footprint gels are shown in FIG. 3.

TABLE 1

Equilibrium dissociation constants*

| Polyamide† | 5'-TGGTCA-3' | 5'-TGGACA-3' | $K_{rel}$‡ |
|---|---|---|---|
| 1 Py/Py | 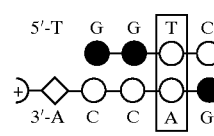 $K_d$ = 0.077 nM | 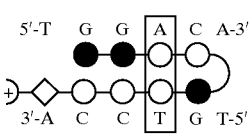 $K_d$ = 0.15 nM | 2.0 |
| 2 Py/Hp | 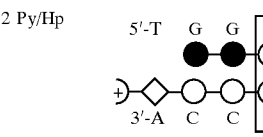 $K_d$ = 15 nM | 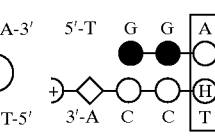 $K_d$ = 0.83 nM | 0.06 |

TABLE 1-continued

Equilibrium dissociation constants*

| Polyamide† | 5'-TGGTCA-3' | 5'-TGGACA-3' | $K_{rel}$‡ |
|---|---|---|---|
| 3 Hp/Py | 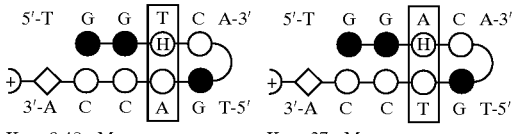 $K_d$ = 0.48 nM |  $K_d$ = 37 nM | 77 |

*The reported dissociation constants are the average values obtained from three DNase I footprint titration experiments. The standard deviation for each data set is less than 15% of the reported number. Assays were carried out in the presence of 10 mM Tris · HCl, 10 mM KCl, 10 mM MgCl$_2$, and 5 mM CaCl$_2$ at pH 7.0 and 22° C.
†Ring pairing opposite T · A and A · T in the fourth position.
‡Calculated as $K_d$(5'-TGGACA-3')/$K_d$(5'-TGGTCA-3').

Based on the pairing rules for polyamide-DNA complexes both of these sequences are a match for control polyamide 1 which places a Py/Py pairing opposite A·T and T·A at both sites. It was determined that in polyamide 1 (Py/Py) binds to 5'-TGGTCA-3' and 5'-TGGACA-3' within a factor of 2 ($K_d$=0.077 or 0.15 nM respectively). In contrast, polyamide 2 (Py/Hp) binds to 5'-TGGTCA-3' and 5'-TGGACA-3' with dissociation constants which differ by a factor of 18 ($K_d$=15 nM and 0.83 nM respectively). By reversing the pairing in polyamide 3 (Hp/Py) the dissociation constants differ again in the opposite direction by a factor of 77 ($K_d$=048 nM and 37 nM respectively. Control experiments performed on separate DNA fragments; reveal that neither a 5'-TGGGCA-3' or a 5'-TGGCCA-3' site is bound by polyamide 2 or 3 at concentrations <100 nM, indicating that the Hp/Py and Py/Hp ring pairings do not bind opposite G·C or C·G. The A·T vs. T·A discrimination is achieved preferably when the two neighboring base pairs are G·C and C·G (GTC vs. GAC).

The specificity of polyamides 2 and 3 for sites which differ by a single A·T/T·A base pair results from small chemical changes. Replacing the Py/Py pair in 1 with a Py/Hp pairing as in 2, a single substitution of C3-OH for C3-H, destabilizes interaction with 5'-TGGTCA-3' by 191-fold, a free energy difference of 3.1 kcal mol$^{-1}$. Interaction of 2 with 5'-TGGACA-3' is destabilized only 6-fold relative to 1, a free energy difference of 1.1 kcal mol$^{-1}$. Similarly, replacing the Py/Py pair in 1 with Hp/Py as in 3 destabilizes interaction with 5'-TGGACA-3' by 252-fold, a free energy difference of 3.2 kcal mol$^{-1}$. Interaction of 3 with 5'TGGTCA-3' is destabilized only 6-fold relative to 1, a free energy difference of 1.0 kcal mol$^{-1}$.

The polyamides of this invention provide for coded targeting of predetermined DNA sequences with affinity and specificity comparable to sequence specific DNA binding proteins. Hp, Im, and Py polyamides complete the minor groove recognition code using three aromatic amino acids which combine to form four ring pairings (Im/Py, Py/Im, Hp/Py, and Py/Hp) which complement the four Watson-Crick base pairs, as shown in TABLE 2. There are a possible 240 four base pair sequences which contain at least 1 A·T or T·A base pair and therefore can advantageously use an Hp/Py, or Py/Hp carboxamide binding. Polyamides binding to any of these sequences can be designed in accordance with the code of TABLE 2.

TABLE 2

| Pairing code for minor groove recognition* | | | | |
|---|---|---|---|---|
| Pair | G•C | C•G | T•A | A•T |
| Im/Py | + | − | − | − |
| Py/Im | − | + | − | − |
| Hp/Py | − | − | + | − |
| Py/Hp | − | − | − | + |

*favored (+), disfavored (−)

For certain G·C rich sequences the affinity of polyamide·DNA complexes may be enhanced by substitution of an Im/β pair for Im/Py at G·C and β/Im for Py/Im at C·G. At A·T and T·A base pairs, either a Py/β, β/Py, and β/β may be used. The alternate aliphatic/aromatic amino acid pairing code is described in Table 3.

TABLE 3

| Aliphatic/Aromatic substitution for ring pairings* | |
|---|---|
| Pair | Substitution |
| Im/Py | Im/β |
| Py/Im | β/Im |
| Hp/Py | Py/β, β/Py, Hp/β, β/β |
| Py/Hp | Py/β, β/Py, β/Hp, β/β |

U.S. Pat. No. 5,578,444 describes numerous promoter region targeting sequences from which base pair sequences for targeting a polyamide can be identified.

PCT U.S. 97/003332 describes methods for synthesis of polyamides which are suitable for preparing polyamides of this invention. The use of β-alanine in place of a pyrrole amino acid in the synthetic methods provides aromatic/aliphatic pairing (Im/β, β/Im, Py/β, and β/Py) and aliphatic/aliphatic pairing (β/β) substitution. The use of γ-aminobutyric acid, or a substituted γ-aminobutyric acid such as (R)-2,4 diaminobutyric acid, provides for preferred hairpin turns. The following examples illustrate the synthesis of polyamides of the present invention.

EXAMPLE 1

Preparation of a Protected Hp Monomer for Solid Phase Synthesis

Distamycin and its analogs have previously been considered targets of traditional multistep synthetic chemistry.

Arcamone, F., Orezzi, P. G., Barbieri, W., Nicolella, V. & Penco, S. describe a solution phase synthesis of distamycin *Gazz. Chim. Ital.* 1967, 97, 1097. The repeating amide of distamycin is formed from an aromatic carboxylic acid and an aromatic amine. The aromatic acid is often unstable to decarboxylation, and the aromatic amines have been found to be air and light sensitive. Lown, J. W. & Krowicki, K. describe a solution phase synthesis of Distamycin *J. Org. Chem.* 1985, 50, 3774. The variable coupling yields, long reaction times (often >24 h), numerous side products, and reactive intermediates (acid chlorides and trichloro ketones) characteristic of the traditional solution phase coupling reactions make the synthesis of the aromatic carboxamides problematic. B. Merrifield describes the solid phase synthesis of a tetrapeptide *J. Am. Chem. Soc.* 1963, 85, 2149. In order to implement an efficient solid phase methodology for the synthesis of the pyrrole-imidazole polyamides, the following components were developed: (1) a synthesis which provides large quantities of appropriately protected monomer or dimer building blocks in high purity, (2) optimized protocols for forming an amide in high yield from a support-bound aromatic amine and an aromatic carboxylic acid, (3) methods for monitoring reactions on the solid support, and (4) a stable resin linkage agent that can be cleaved in high yield upon completion of the synthesis. Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. In order to prepare polyamides which contain the 3-hydroxypyrrole monomer, a synthesis has been developed which allows the appropriately protected Boc-Op acid monomer to be prepared on 50 g scale. 1H NMR and $^{13}$C NMR spectra were recorded on a General Electric-QE 300 NMR spectrometer in $CD_3OD$ or $DMSO-d_6$, with chemical shifts reported in parts per million relative to residual $CHD_2OD$ or $DMSO-d_5$, respectively. IR spectra were recorded on a Perkin-Elmer FTIR spectrometer. High-resolution mass spectra were recorded using fast atom bombardment (FABMS) techniques at the Mass Spectrometry Laboratory at the University of California, Riverside. Reactions were executed under an inert argon atmosphere. Reagent grade chemicals were used as received unless otherwise noted. Still, W. C., Kahn, M. & Mitra, A. describe flash column chromatography *J. Org. Chem.* 1978, 40, 2923–2925. Flash chromatography was carried out using EM science Kieselgel 60 (230–400) mesh. Thin-layer chromatography was performed on EM Reagents silica gel plates (0.5 mm thickness). All compounds were visualized with short-wave ultraviolet light.

TABLE 4

Intermediates for preparation of Boc-protected 3-methoxypyrrole

| NAME | STRUCTURE |
|---|---|
| Ethyl 4-carboxy-3-hydroxy-1-methylpyrrole-2-carboxylate. | 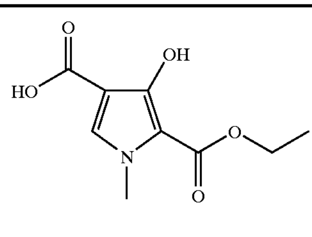 |

TABLE 4-continued

Intermediates for preparation of Boc-protected 3-methoxypyrrole

| NAME | STRUCTURE |
|---|---|
| Ethyl 4-[(Benzyl-oxycarbonyl)-amino]-3-hydroxy-1-methylpyrrole-2-carboxylate | |
| Ethyl 4-[(Benzyl-oxycarbonyl)-amino]-3-methoxy-1-methylpyrrole-2-carboxylate | |
| Ethyl 4-[(tert-Butyl-oxycarbonyl)-amino]-3-methoxy-1-methylpyrrole-2-carboxylate | |
| 4-[(tert-Butyloxy-carbonyl)amino]-3-methoxy-1-methyl-pyrrole-2-carboxylic acid | |

Ethyl 4-[(benzyloxycarbonyl)amino]-3-hydroxy-1-methylpyrrole-2-carboxylate Ethyl-4-carboxy-3-hydroxy-1-methylpyrrole-2-carboxylate (60 g, 281.7 mmol) was dissolved in 282 mL acetonitrile. TEA (28.53 g, 282 mmol) was added, followed by diphenylphosphorylazide (77.61 g, 282 mmol). The mixture was refluxed for 5 hours, followed by addition of benzyl alcohol (270 ml) and reflux continued overnight. The solution was cooled and volitiles removed in vacuo. The residue was absorbed onto silca and chromatagraphed, 4:1 hexanes ethyl acetate, to give a white solid (21.58 g, 24%) $^1$H NMR (DMSO-$d_6$) δ 8.73 (s, 1H), 8.31 (s, 1H), 7.31 (m, 5H), 6.96 (s, 1H), 5.08 (s, 2H), 4.21 (q, 2H, J=7.1 Hz), 3.66 (s, 3H), 1.25 (t, 3H, J=7.1 Hz); MS m/e 319.163 (M+H 319.122 calcd. for $C_{16}H_{18}N_2O_5$).

Ethyl 4-[(tert-butoxycarbonyl)amino]-3-methoxy-1-methylpyrrole-2-carboxylate. Ethyl 4-[(benzyloxycarbonyl)amino]-3-hydroxy1-methylpyrrole-2-carboxylate (13.4 g, 42.3 mmol) was dissolved in 110 mL acetone. Anhydrous $K_2CO_3$ (11.67 g, 84.5 mmol) was added, followed by methyliodide (5.96 g, 42.3 mmol) and dimethylaminopyridine (0.5 g, 4.23 mmol) and the mixture stirred overnight. The solid $K_2CO_3$ was removed by filtration and 200 ml water added. Volitiles were removed in vacuo and the solution made acidic with addition of 1N $H_2SO_4$. The aqueous layer was extracted with diethyl ether. Organic layers were combined, washed with 10% $H_2SO_4$, dried over $MgSO_4$, and dried to give a white solid. The solid was used without further purification and dissolved in 38 ml DMF. DIEA (11 ml), Boc anhydride (9.23 g, 42.3 mmol), and 10% Pd/C (500 mg) were added and the solution stirred under hydrogen (1 atm) for 2.1 h. The slurry was filtered through celite which was washed with methanol. Water 250 ml was added and volitiles removed in vacuo. The aqueous layer was extracted with ether. Organic layers were combined, washed with water and brine, and dried over $MgSO_4$. Solvent was removed in to give a white solid (8.94 g, 71%) $^1$H NMR (DMSO-$d_6$) δ 8.43 (s, 1H), 7.03 (s, 1H), 4.19 (q, 2H, J=7.1 Hz), 3.70 (s, 3H), 1.42 (s, 9H), 1.26 (t, 3H, J=7.1); MS m/e 299.161 (M+H 299.153 calcd. for $C_{14}H_{22}N_2O_5$).

Ethyl 4-[(benzyloxycarbonyl)amino]-3-hydroxy-1-methylpyrrole-2-carboxylate Ethyl 4-[(tert-butoxycarbonyl) amino]-3-methoxy-1-methylpyrrole-2-carboxylate (9.0 g, 30.2 mmol) was dissolved in 30 mL ethanol. NaOH (30 ml, 1 M, aq) was added and the solution stirred for 4 days. Water (200 ml) was added and ethanol removed in vacuo. The solution was extracted with diethyl ether, aqueous layer acidified to pH=2–3, and extracted again with diethyl ether. Organic layers were dried over $MgSO_4$, and solvent removed in vacuo to give a white solid (6.0 g, 20.5 mmol, 87% based on recovered SM) $^1$H NMR (DMSO-$d_6$) δ 12.14 (s, 1H), 8.37 (s, 1H), 6.98 (s, 1H), 3.69 (s, 3H), 3.66 (s, 3H), 1.42 (s, 9H); MS m/e 293.112 (M+H 293.104 calcd. for $C_{12}H_{18}N_2O_5$).

EXAMPLE 2

Solid Phase Synthesis of 2-Hydroxypyrrole Polyamides

Cycling protocols were optimized to afford high stepwise coupling yields (>99%). Deprotection by aminolysis affords up to 100 mg quantities of polyamide. Solid phase polyamide synthesis protocols were modified from the in situ neutralization Boc-chemistry protocols. Schnolzer, M., Alewood, P., Jones, A., Alewood, D., Kent, S. B. H. report rapid in situ neutralization for solid phase peptide synthesis *Int. J. Peptide. Protein. Res.* 1992, 40, 180. Coupling cycles are rapid, 72 min per residue for manual synthesis or 180 min per residue for machine-assisted synthesis, and require no special precautions beyond those used for ordinary solid phase peptide synthesis. Manual solid phase synthesis of a pyrrole-imidazole polyamide consists of a dichloromethane (DCM) wash, removal of the Boc group with trifluoroacetic acid (TFA)/DCM/thiophenol (PhSH), a DCM wash, a DMF wash, taking a resin sample for analysis, addition of activated monomer, addition of DIEA if necessary, coupling for 45 min, taking a resin sample for analysis, and a final DMF wash (FIG. 5, Table I). In addition, the manual solid phase protocol for synthesis of pyrrole-imidazole polyamides has been adapted for use on a ABI 430A peptide synthesizer. The aromatic amine of the pyrrole and imidazole do not react in the quantitative ninhydrin test. Stepwise cleavage of a sample of resin and analysis by HPLC indicates that high stepwise yields (>99%) are routinely achieved.

Dicyclohexylcarbodiimide (DCC), Hydroxybenzotriazole (HOBt), 2-(1H-Benzotriazole-1-yl)-1,1,3,3-tetramethyluronium hexa-fluorophosphate (HBTU) and 0.2 mmol/gram Boc-β-alanine-(-4-carboxamide)-benzyl-ester-copoly(styrene-divinylbenzene) resin (Boc-β-Pam-Resin) was purchased from Peptides International (0.2 mmol/gram), NovaBiochem (0.6 mmol/gram), or Peninsula (0.6 mmol/gram). ((R)-2-Fmoc-4-Boc-diaminobutyric acid, (S)-2-Fmoc-4-Boc-diaminobutyric acid, and (R)-2-amino-4-Boc-diaminobutyric acid were purchased from Bachem. N,N-diisopropylethylamine (DIEA), N,N-dimethylformamide (DMF), N-methylpyrrolidone (NMP), DMSO/NMP, Acetic anhydride ($Ac_2O$), and 0.0002 M potassium cyanide/pyridine were purchased from Applied Biosystems. Dichloromethane (DCM) and triethylamine (TEA) were reagent grade from EM, thiophenol (PhSH), dimethylaminopropylamine (Dp), Sodium Hydride, (R)-α-methoxy-α-(trifioromethyl)phenylacetic acid ((R)MPTA) and (S)-α-methoxy-α-(trifouromethyl)phenylacetic acid ((S)MPTA) were from Aldrich, trifluoroacetic acid (TFA) Biograde from Halocarbon, phenol from Fisher, and ninhydrin from Pierce. All reagents were used without further purification.

Quik-Sep polypropylene disposable filters were purchased from Isolab Inc. $^1$H NMR spectra were recorded on a General Electric-QE NMR spectrometer at 300 MHz with chemical shifts reported in parts per million relative to residual solvent. UV spectra were measured in water on a Hewlett-Packard Model 8452A diode array spectrophotometer. Optical rotations were recorded on a JASCO Dip 1000 Digital Polarimeter. Matrix-assisted, laser desorption/ionization time of flight mass spectrometry (MALDI-TOF) was performed at the Protein and Peptide Microanalytical Facility at the California Institute of Technology. HPLC analysis was performed on either a HP 1090M analytical HPLC or a Beckman Gold system using a RAINEN $C_{18}$, Microsorb MV, 5 μm, 300×4.6 mm reversed phase column in 0.1% (wt/v) TFA with acetonitrile as eluent and a flow rate of 1.0 mL/min, gradient elution 1.25% acetonitrile/min. Preparatory reverse phase HPLC was performed on a Beckman HPLC with a Waters DeltaPak 25×100 mm, 100 μm $C_{18}$ column equipped with a guard, 0.1% (wt/v) TFA, 0.25% acetonitrile/min. 18MΩ water was obtained from a Millipore MilliQ water purification system, and all buffers were 0.2 μm filtered.

Activation of Boc-3-methoxypyrrole acid. The amino acid (0.5 mmol) was dissolved in 2 mL DMF. HBTU (190 mg, 0.5 mmol) was added followed by DIEA (1 mL) and the resulting mixture was shaken for 5 min.

Activation of Inidazole-2-carboxylic acid, γ-aminobutyric acid, Boc-glycine, and Boc-β-alanine. The appropriate amino acid or acid (2 mmol) was dissolved in 2 mL DMF. HBTU (720 mg, 1.9 mmol) was added followed by DIEA (1 mL) and the solution shaken for at least 5 min.

Activation of Boc-Imidazole acid. Boc imidazole acid (257 mg, 1 mmol) and HOBt (135 mg, 1 mmol) were dissolved in 2 mL DMF, DCC (202 mg, 11 mmol) is then added and the solution allowed to stand for at least 5 min.

Acetylation Mix. 2 mL DMF, DIEA (710 μL, 4.0 mmol), and acetic anhydride (380 μL, 4.0 mmol) were combined immediately before use.

Manual Synthesis Protocol. Boc-β-alanine-Pam-Resin (1.25 g, 0.25 mmol) is placed in a 20 mL glass reaction vessel, shaken in DMF for 5 min and the reaction vessel drained. The resin was washed with DCM (2×30 s.) and the Boc group removed with 80% TFA/DCM/0.5M PhSH, 1×30s., 1×20 min The resin was washed with DCM (2×30 s.) followed by DMF (1×30 s.) A resin sample (5–10 mg) was taken for analysis. The vessel was drained completely and activated monomer added, followed by DIEA if necessary. The reaction vessel was shaken vigorously to make a slurry. The coupling was allowed to proceed for 90 min, and a resin sample taken. Acetic anhydride (1 mL) was added and the reaction shaken for 5 min. The reaction vessel was then washed with DMF, followed by DCM.

Machine-Assisted Protocols. Machine-assisted synthesis was performed on a ABI 430A synthesizer on a 0.18 mmol scale (900 mg resin; 0.2 mmol/gram). Each cycle of amino acid addition involved: deprotection with approximately 80% TFA/DCM/0.4M PhSH for 3 minutes, draining the reaction vessel, and then deprotection for 17 minutes; 2 dichloromethane flow washes; an NMP flow wash; draining the reaction vessel; coupling for 1 hour with in situ neutralization, addition of dimethyl sulfoxide (DMSO)/NMP, coupling for 30 minutes, addition of DIEA, coupling for 30 minutes; draining the reaction vessel; washing with DCM, taking a resin sample for evaluation of the progress of the synthesis by HPLC analysis; capping with acetic anhydride/DIEA in DCM for 6 minutes; and washing with DCM. A double couple cycle is employed when coupling aliphatic amino acids to imidazole, all other couplings are performed with single couple cycles.

The ABI 430A synthesizer was left in the standard hardware configuration for NMP-HOBt protocols. Reagent positions 1 and 7 were DIEA, reagent position 2 was TFA/0.5M thiophenol, reagent position 3 was 70% ethanolamine/methanol, reagent position 4 was acetic anhydride, reagent position 5 was DMSO/NMP, reagent position 6 was methanol, and reagent position 8 was DMF. New activator functions were written, one for direct transfer of the cartridge contents to the concentrator (switch list 21, 25, 26, 35, 37, 44), and a second for transfer of reagent position 8 directly to the cartridge (switch list 37, 39, 45, 46).

Boc-Py-OBt ester (357 mg, 1 mmol) was dissolved in 2 ml DMF and filtered into a synthesis cartridge. Boc-Im acid monomer was activated (DCC/HOBt), filtered, and placed in a synthesis cartridge imidazole-2-carboxylic acid was added manually. At the initiation of the coupling cycle the synthesis was interrupted, the reaction vessel vented and the activated monomer added directly to the reaction vessel through the resin sampling loop via syringe. When manual addition was necessary an empty synthesis cartridge was used. Aliphatic amino acids (2 mmol) and HBTU (1.9 mmol) were placed in a synthesis cartridge. 3 ml of DMF was added using a calibrated delivery loop from reagent bottle 8, followed by calibrated delivery of 1 ml DIEA from reagent bottle 7, and a 3 minute mixing of the cartridge.

The activator cycle was written to transfer activated monomer directly from the cartridge to m the concentrator vessel, bypassing the activator vessel. After transfer, 1 ml of DIEA was measured into the cartridge using a calibrated delivery loop, and the DIEA solution combined with the activated monomer solution in the concentrator vessel. The activated ester in 2:1 DMF/DIEA was then transferred to the reaction vessel. All lines were emptied with argon before and after solution transfers.

ImImOpPy-γ-ImPyPyPy-β-Dp. ImImOpPy-γ-ImPyPyPy-β-Pam-Resin was synthesized in a stepwise fashion by machine-assisted solid phase methods from Boc-β-Pam-Resin (0.66 mmol/g). Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. 3-hydroxypyrrole-Boc-amino acid (0.7 mmol) was incorporated by placing the amino acid (0.5 mmol) and HBTU (0.5 mmol) in a machine synthesis cartridge. Upon automated delivery of DMF (2 mL) and DIEA (1 mL) activation occurs. A sample of ImImOpPy-γ-ImPyPyPy-β-Pam-Resin (400 mg, 0.40 mmol/gram) was placed in a glass 20 mL peptide synthesis vessel and treated with neat dimethylaminopropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImImOpPy-γ-hmPyPyPy-β-Dp is recovered upon lyophilization of the appropriate fractions as a white powder (97 mg, 49% recovery). UV ($H_2O$) $\lambda_{max}$ 246, 316 (66,000); $^1$H NMR (DMSO-$d_6$) δ 10.24 (s, 1H), 10.14 (s, 1H), 9.99 (s, 1H), 9.94 (s, 1H), 9.88 (s, 1H), 9.4 (br s, 1H), 9.25 (s, 1H), 9.11 (s, 1H), 8.05 (m, 3H), 7.60 (s, 1H), 7.46 (s, 1H), 7.41 (s, 1H), 7.23 (d, 1H), 7.21 (d, 1H), 7.19 (d, 1H), 7.13 (m, 2H), 7.11 (m, 2H), 7.02 (d, 1H), 6.83 (m, 2H), 3.96 (s, 6H), 3.90 (s, 3H), 3.81 (m, 6H), 3.79 (s, 3H), 3.75 (d, 9H), 3.33 (q, 2H, J=5.4 Hz), 3.33 (q, 2H, J=5.5 Hz), 3.08 (q, 2H, J=6.0 Hz), 2.96 (quintet, 2H, J=5.6 Hz), 2.70 (d, 6H, J=4.5 Hz), 2.32 (m, 4H), 1.71 (m, 4H); MALDI-TOF-MS (monoisotopic), 1253.5 (1253.6 calc. for $C_{58}H_{72}N_{22}O_{11}$).

ImImHpPy-γ-ImPyPyPy. In order to remove the methoxy protecting group, a sample of ImimOpPy-γ-ImPyPyPy-β-Dp (5 mg, 3.9 μmol) was treated with sodium thiophenoxide at 100° C. for 2 h, DMF (100 μL) and thiophenol (500 μL) were placed in a (13×100 mm) disposable Pyrex screw cap culture tube. A 60% dispersion of sodium hydride in mineral oil (100 mg) was slowly added. Upon completion of the addition of the sodium hydride, ImImOpPy-γ-ImPyPyPy-β-Dp (5 mg) dissolved in DMF (500 μL) was added. The solution was agitated, and placed in a 100° C. heat block, and deprotected for 2 h. Upon completion of the reaction the culture tube was cooled to 0° C., and 7 ml of a 20% (wt/v) solution of trifluoroacetic acid added. The aqueous layer is separated from the resulting biphasic solution and purified by reversed phase HPLC. ImHpPy-γ-ImPyPyPy-β-Dp is recovered as a white powder upon lyophilization of the appropriate fractions (3.8 mg, 77% recovery). UV ($H_2O$) o 246, 312 (66,000); $^1$H NMR (DMSO-$d_6$) δ 10.34 (s, 1H), 10.24 (s, 1H), 10.00 (s, 2H), 9.93 (s, 1H), 9.83 (s, 1H), 9.4 (br s, 1H), 9.04 (s, 1H), 8.03 (m, 3H), 7.58 (s, 1H), 7.44 (s, 1H), 7.42 (s, 1H), 7.23 (s, 1H), 7.20 (m, 3H), 7.12 (m, 2H), 7.05 (d, 1H), 7.02 (d, 1H), 6.83 (s, 1H), 6.79 (s, 1H), 3.96 (s, 6H), 3.90 (s, 3H), 3.81 (s, 6H), 3.79 (s, 3H), 3.75 (d, 6H), 3.33 (q, 2H, J=5.4 Hz), 3.14 (q, 2H, J=5.4 Hz), 3.08 (q, 2H, J=6.1 Hz), 2.99 (quintet, 2H, J=5.4 Hz), 2.69 (d, 6H, J=4.2 Hz), 2.31 (m, 4H), 1.72 (m, 4H); MALDI-TOF-MS (monoisotopic), 1239.6 (1239.6 calc. for $C_{57}H_{71}N_{22}O_{11}$)

ImImPy-γ-ImOpPyPy-β-Dp. ImImPyPy-γ-ImOpPyPy-β-Pam-Resin was synthesized in a stepwise fashion by machine-assisted solid phase methods from Boc-β-Pam-Resin (0.66 mmol/g) as described for ImImOpPy-γ-ImPyPyPy-β-Dp. A sample of ImImPyPy-γ-ImopPyPy-β-Pam-Resin (400 mg, 0.40 mmol/gram) was placed in a glass 20 mL peptide synthesis vessel and treated with neat dimethylaminopropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImImPyPy-γ-ImOpPyPy-β-Dp is recovered upon lyophilization of the appropriate fractions as a white powder (101 mg, 50% recovery). UV ($H_2O$)$\lambda_{max}$ 246, 316 (66,000); MALDI-TOF-MS (monoisotopic), 1253.6 (1253.6 calc. for $C_{58}H_{72}N_{22}O_{11}$).

ImImPyPy-γ-ImHpPyPy. A sample of ImImPyPy-γ-ImOpPyPy-β-Dp (5 mg, 3.9 μmol) was treated with sodium thiophenoxide and purified by reversed phase HPLC as described for ImImHpPy-γ-ImPyPyPy-β-Dp. ImImPyPy-γ-ImHpPyPy-β-Dp is recovered upon lyophilization of the appropriate fractions as a white powder (3.2 mg, 66% recovery). UV ($H_2O$) L 246, 312 (66,000); MALDI-TOF-MS (monoisotopic), 1239.6 (1239.6 calc. for $C_{57}H_{71}N_{22}O_1$).

ImPyPy-γ-OpPyPy-β-Dp. ImPyPy-γ-OpPyPy-β-Pam-Resin was synthesized in a stepwise fashion by machine-assisted solid phase methods from Boc-β-Pam-Resin (0.66 mmol/g). Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. 3-hydroxypyrrole Boc amino acid (0.7 mmol) was incorporated by placing the amino acid (0.5 mmol) and HBTU (0.5 mmol) in a machine synthesis cartridge. Upon automated delivery of DMF (2 mL) and DIEA (1 mL) activation occurs. A sample of ImPyPy-γ-OpPyPy-β-Pam-Resin (400 mg, 0.45 mmol/gram) was placed in a glass 20 mL peptide synthesis vessel and treated with neat dimethylaminopropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImImPyPy-γ-OpPyPy-β-Dp is recovered upon lyophilization of the appropriate fractions as a white powder (45 mg, 25% recovery). UV ($H_2O$) $\lambda_{max}$ 246, 310 (50,000); $^1$H NMR (DMSO-$d_6$) δ 10.45 (s, 1H), 9.90 (s, 1H), 9.82 (s, 1H), 9.5 (br s, 1H), 9.38 (s, 1H), 9.04 (s, 1H), 8.02 (m, 3H), 7.37 (s, 1H), 7.25 (m, 2H), 7.15 (d, 1H, J=1.6 Hz), 7.11 (m, 2H), 7.09 (d, 1H), 7.03 (s, 1H), 6.99 (d, 1H), 6.87 (d, 1H), 6.84 (d, 1H), 3.96 (s, 3H), 3.81 (s, 6H), 3.76 (s, 3H), 3.74 (s, 1H), 3.34 (q, 2H, J=5.6 Hz), 3.20 (q, 2H, J=5.8 Hz), 3.09 (q, 2H, J6.1 Hz), 2.97 (quintet, 2H, J=5.3 Hz), 2.70 (d, 6H, J=3.9 Hz), 2.34 (m, 4H), 1.73 (m, 4H); MALDI-TOF-MS (monoisotopic), 1007.6 (1007.5 calc. for $C_{48}H_{63}N_{16}O_9$).

ImPyPy-γ-HpPyPy. In order to remove the methoxy protecting group, a sample of ImPyPy-γ-OpPyPy-β-Dp (5 mg, 4.8 μmol) was treated with sodium thiophenoxide at 100° C. for 2 h. DMF (1000 μL) and thiophenol (500 μL) were placed in a (13×100 mm) disposable Pyrex screw cap culture tube. A 60% dispersion of sodium hydride in mineral oil (100 mg) was slowly added. Upon completion of the addition of the sodium hydride, ImImPyPy-γ-ImOpPyPy-β-Dp (5 mg) dissolved in DMF (500 μL) was added. The solution was agitated, and placed in a 100° C. heat block, and deprotected for 2 h. Upon completion of the reaction the culture tube was cooled to 0° C., and 7 ml of a 20% (wt/v) solution of trifluoroacetic acid added. The aqueous layer is separated from the resulting biphasic solution and purified by reversed phase HPLC. ImImpPy-γ-ImHpPyPy-β-Dp is recovered as a white powder upon lyophilization of the appropriate fractions (2.5 mg, 52% recovery). UV ($H_2O$) $\lambda_{max}$ 246, 310 (50,000); $^1$H NMR (DMSO-$d_6$) δ 10.44 (s, 1H), 10.16 (s, 1H), 9.90 (s, 1H), 9.77 (s, 1H), 9.5 (br s, 1H), 9.00 (s, 1H), 8.03 (m, 3H), 7.37 (s, 1H), 7.26 (m, 2H), 7.14 (d, 1H, J=1.7 Hz), 7.26 (m, 2H), 7.02 (d, 1H), 6.93 (d, 1H), 6.88 (d, 1H), 6.82 (d, 1H), 6.72 (d, 1H), 3.96 (s, 3H), 3.81 (s, 6H), 3.77 (s, 3H), 3.76 (s, 3H), 3.74 (s, 1H), 3.36 (q, 2H, J=5.4 Hz), 3.22 (q, 2H, J=5.9 Hz), 3.09 (q, 2H, J=5.5 Hz), 2.98 (quintet, 2H, J=5.3 Hz), 2.70 (d, 6H, J=4.3 Hz), 2.34 (s, 4H), 1.78 (m, 4H); MALDI-TOF-MS (monoisotopic), 994.2 (993.5 calc. for $C_{47}H_{61}N_{16}O_9$).

TABLE 5

Mass spectral characterization of Op and Hp polyamides, synthesized and purified as described for ImImOpPy-γ-ImPyPyPy-β-Dp and ImImHpPy-γ-ImPyPyPy-β-Dp.

| POLYAMIDE | FORMULA | (M + H)CALCD | FOUND |
| --- | --- | --- | --- |
| ImOpPy-γ-PyPyPy-β-Dp | $C_{48}H_{63}N_{16}O_9$ | 1007.5 | 1007.5 |
| ImHpPy-γ-PyPyPy-β-Dp | $C_{47}H_{61}N_{16}O_9$ | 993.5 | 993.2 |
| ImPyOp-γ-PyPyPy-β-Dp | $C_{48}H_{63}N_{16}O_9$ | 1007.5 | 1007.5 |
| ImPyHp-γ-PyPyPy-β-Dp | $C_{47}H_{61}N_{16}O_9$ | 993.5 | 993.4 |
| ImPyPy-γ-OpPyPy-β-Dp | $C_{48}H_{63}N_{16}O_9$ | 1007.5 | 1007.6 |
| ImPyPy-γ-HpPyPy-β-Dp | $C_{47}H_{61}N_{16}O_9$ | 993.5 | 993.2 |
| ImPyPy-γ-PyOpPy-β-Dp | $C_{48}H_{63}N_{16}O_9$ | 1007.5 | 1007.5 |
| ImPyPy-γ-PyHpPy-β-Dp | $C_{47}H_{61}N_{16}O_9$ | 993.5 | 993.4 |
| ImOpOp-γ-PyPyPy-β-Dp | $C_{49}H_{65}N_{16}O_{10}$ | 1037.5 | 1037.5 |
| ImHpHp-γ-PyPyPy-β-Dp | $C_{47}H_{61}N_{16}O_{10}$ | 1009.5 | 1009.4 |
| ImImOpPy-γ-ImPyPyPy-β-Dp | $C_{58}H_{72}N_{22}O_{11}$ | 1253.6 | 1253.5 |
| ImImHpPy-γ-ImPyPyPy-β-Dp | $C_{57}H_{71}N_{22}O_{11}$ | 1239.6 | 1239.6 |
| ImImPyPy-γ-ImOpPyPy-β-Dp | $C_{58}H_{72}N_{16}O_{11}$ | 1253.6 | 1253.6 |
| ImImPyPy-γ-ImHpPyPy-β-Dp | $C_{57}H_{71}N_{22}O_{11}$ | 1239.6 | 1239.6 |
| ImOpPyPy-γ-ImOpPyPy-β-Dp | $C_{60}H_{76}N_{21}O_{12}$ | 1282.6 | 1282.6 |
| ImHpPyPy-γ-ImHpPyPy-β-Dp | $C_{58}H_{72}N_{21}O_{12}$ | 1254.6 | 1254.6 |
| ImImOpPy-γ-ImOpPyPy-β-Dp | $C_{59}H_{75}N_{22}O_{12}$ | 1283.6 | 1283.6 |
| ImImHpPy-γ-ImHpPyPy-β-Dp | $C_{57}H_{71}N_{22}O_{12}$ | 1255.6 | 1255.5 |
| ImOpPyPy-γ-PyPyPyPy-β-Dp | $C_{60}H_{75}N_{20}O_{11}$ | 1251.6 | 1251.5 |
| ImPyPyPy-γ-PyPyOpPy-β-Dp | $C_{60}H_{75}N_{20}O_{11}$ | 1251.6 | 1251.5 |
| ImImPyPy-γ-ImPyOpPy-β-Dp | $C_{58}H_{72}N_{22}O_{11}$ | 1253.6 | 1253.7 |
| ImOpPyPyPy-γ-ImOpPyPyPy-β-Dp | $C_{72}H_{88}N_{25}O_{14}$ | 1526.7 | 1526.6 |
| ImHpPyPyPy-γ-ImHpPyPyPy-β-Dp | $C_{70}H_{84}N_{25}O_{14}$ | 1498.7 | 1498.0 |
| ImImPyPyPy-γ-ImOpPyPyPy-β-Dp | $C_{71}H_{87}N_{26}O_{14}$ | 1527.7 | 1527.7 |

EXAMPLE 3

Determination of Polyamide Binding Affinity and Sequence Specificity

Representative footprint titration experiments are shown in FIGS. 3 and 10. A 252-bp DNA fragment which is typically used for the footprint titration experiments provides 247 possible 6-bp binding sites for an eight-ring hairpin polyamide. Thus, in addition to providing DNA binding affinities, the footprint titration experiments also reveal DNA binding sequence-specificity. The DNA binding sequence specificity of polyamides which differ by a single Py/Py, Hp/Py, or Py/Hp pair for sites which differ by a single A·T or T·A base pair are described in Tables 1, 6, and 7.

Quantitative DNase I Footprint Titrations All reactions were executed in a total volume of 400 μL (Brenowitz, M. et al., 1986). A polyamide stock solution or $H_2O$ (for reference lanes) was added to an assay buffer containing 3'-$^{32}$P radiolabeled restriction fragment (20,000 cpm), affording final solution conditions of 10 mM Tris-HCl, 10 mM KCl, 10 mM $MgCl_2$, 5 mM $CaCl_2$, pH 7.0, and either (i) a suitable concentration range of polyamide, or (ii) no polyamide (for reference lanes). The solutions were allowed to equilibrate for 24 hours at 22° C. Footprinting reactions were initiated by the addition of 10 μL of a stock solution of DNase I (at the appropriate concentration to give 55% intact DNA) containing 1 mM dithiothreitol and allowed to proceed for 7 minutes at 22° C. The reactions were stopped by the addition of 50 μL of a solution containing 2.25 M NaCl, 150 mM EDTA, 23 μM base pair calf thymus DNA, and 0.6 mg/ml glycogen, and ethanol precipitated. The reactions were resuspended in 1×TBE/80% formamide loading buffer, denatured by heating at 85° C. for 15 minutes, and placed on ice. The reaction products were separated by electrophoresis on an 8% polyacrylamide gel (5% crosslinking, 7 M urea) in 1×TBE at 2000 V for 1.5 h. Gels were dried on a slab dryer and then exposed to a storage phosphor screen at 22° C.

Photostimuable storage phosphor imaging plates (Kodak Storage Phosphor Screen SO230 obtained from Molecular Dynamics) were pressed flat against dried gel samples and exposed in the dark at 22° C. for 12–24 hours. A Molecular Dynamics 400S PhosphorImager was used to obtain all data from the storage screens (Johnston et al., 1990). The data were analyzed by performing volume integration of the target site and reference blocks using the ImageQuant v. 3.3 software running on a Compaq Pentium 80.

Quantitative DNase I Footprint Titration Data Analysis was performed by taking a background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($\theta_{app}$) of the sites were calculated using the equation:

$$\theta_{app} = 1 - \frac{I_{site} / I_{ref}}{I^o_{site} / I^o_{ref}} \quad (1)$$

where $I_{site}^o$ and $I_{ref}^o$ are the site and reference intensities, respectively, from a DNase I control lane to which no polyamide was added.

The ($[L]_{tot}$, $\theta_{app}$) data were fit to a Langmuir binding isotherm (eq. 2, n=1) by minimizing the difference between $\theta_{app}$ and $\theta_{fit}$, using the modified Hill equation:

$$\theta_{fit} = \theta_{min} + (\theta_{max} - \theta_{min}) \frac{K_a^n [L]_{tot}^n}{1 + K_a^n [L]_{tot}^n} \quad (2)$$

where $[L_{tot}]$ is the total polyamide concentration, $K_a$ is the equilibrium association constant, and $\theta_{min}$ and $\theta_{max}$ are the experimentally determined site saturation values when the site is unoccupied or saturated, respectively. The data were fit using a nonlinear least-squares fitting procedure of KaleidaGraph software (v. 3.0.1, Abelbeck Software) with $K_a$, $\theta_{max}$, and $\theta_{min}$ as the adjustable parameters. The goodness of fit of the binding curve to the data points is evaluated by the correlation coefficient, with R>0.97 as the criterion for an acceptable fit. Four sets of acceptable data were used in determining each association constant. All lanes from a gel were used unless a visual inspection revealed a data point to be obviously flawed relative to neighboring points. The data were normalized using the following equation:

$$\theta_{norm} = \frac{\theta_{app} - \theta_{min}}{\theta_{max} - \theta_{min}} \quad (3)$$

TABLE 6

Discrimination of 5'-TGTAA-3' and 5'-TGTTA-3'*

[Table 6 shows ring-pairing diagrams for Py/Py, Py/Hp, and Hp/Py polyamide pairs binding to 5'-TGTAA-3' and 5'-TGTTA-3' sites, with dissociation constants:

Py/Py: $K_d = 0.014\,\mu M$ (TGTAA), $K_d = 0.007\,\mu M$ (TGTTA), $K_{rel} = 2.0$
Py/Hp: $K_d = 0.20\,\mu M$ (TGTAA), $K_d = 0.56\,\mu M$ (TGTTA), $K_{rel} = 0.36$
Hp/Py: $K_d = 4.0\,\mu M$ (TGTAA), $K_d = 0.28\,\mu M$ (TGTTA), $K_{rel} = 14$]

*The reported equilibrium dissociation constants are the mean values obtained from two DNase I footprint titration experiments on a 3'[32]P labeled 370-bp pDEH1 EcoRI/PvuII DNA restriction fragment[13]. The assays were carried out at 22° C., pH 7.0 in the presence of 10 mM Tris · HCl, 10 mM KCl, 10 mM MgCl$_2$, and 5 mM CaCl$_2$.
†Ring pairing opposite T · A and A · T in the third position.
‡Calculated as $K_d$(5'-TGTAA-3')/$K_d$(5'-TGTTA-3').

TABLE 7

Discrimination of 5'-TGTTT-3' and 5'-TGATT-3'*

[Table 7 shows ring-pairing diagrams for Py/Py, Hp/Py, and Py/Hp polyamide pairs binding to 5'-TGATT-3' and 5'-TGTTT-3' sites, with dissociation constants:

Py/Py: $K_d = 0.026\,\mu M$ (TGATT), $K_d = 0.005\,\mu M$ (TGTTT), $K_{rel} = 5.2$
Hp/Py: $K_d = 0.53\,\mu M$ (TGATT), $K_d = 0.008\,\mu M$ (TGTTT), $K_{rel} = 66$
Py/Hp: $K_d = 0.33\,\mu M$ (TGATT), $K_d = 0.59\,\mu M$ (TGTTT), $K_{rel} = 0.56$]

*The reported equilibrium dissociation constants are the mean values obtained from two DNase I footprint titration experiments. The assays were carried out at 22° C., pH 7.0 in the presence of 10 mM Tris · HCl, 10 mM KCl, 10 mM MgCl$_2$, and 5 mM CaCl$_2$.

TABLE 7-continued

Discrimination of 5'-TGTTT-3' and 5'-TGATT-3'*

| Pair† | 5'-TGATT-3' | 5'-TGTTT-3' | $K_{rel}$‡ |
|---|---|---|---|

†Ring pairing opposite T · A and A · T in the third position.
‡Calculated as $K_d$(5'-TGATT-3')/$K_d$(5'-TGTTT-3').

EXAMPLE 5

Preparation of a Bifunctional Hp-Py-Im-Polyamide

ImImOpPy-γ-ImPyPyPy-β-Dp-NH$_2$. ImImOpPy-γ-ImPyPyPy-β-Pam-Resin was synthesized in a stepwise fashion by machine-assisted solid phase methods from Boc-β-Pam-Resin (0.66 mmol/g). Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. 3-hydroxypyrrole-Boc-amino acid (0.7 mmol) was incorporated by placing the amino acid (0.5 mmol) and HBTU (0.5 mmol) in a machine synthesis cartridge. Upon automated delivery of DMF (2 mL) and DIEA (1 mL) activation occurs. A sample of ImImOpPy-γ-ImPyPyPy-β-Pam-Resin (400 mg, 0.40 mmol/gram) was placed in a glass 20 mL peptide synthesis vessel and treated with neat 3,3'-diamino-N-methyldipropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImImOpPy-γ-ImPyPyPy-β-Dp-NH$_2$ is recovered upon lyophilization of the appropriate fractions as a white powder (93 mg, 46% recovery). UV (H$_2$O) $\lambda_{max}$ 246, 316 (66,000); $^1$H NMR (DMSO-d$_6$) δ 10.34 (s, 1H), 10.30 (br s, 1H), 10.25 (s, 1H), 9.96 (s, 1H), 9.95 (s, 1H), 9.89 (s, 1H), 9.24 (s, 1H), 9.11 (s, 1H), 8.08 (t, 1H, J=5.6 Hz), 8.0 (m, 5H), 7.62 (s, 1H), 7.53 (s, 1H), 7.42 (s, 1H), 7.23 (d, 1H, J=1.2 Hz), 7.21 (m, 2H), 7.15 (m, 2H), 7.13 (d, 1H), 7.11 (m, 2H), 7.04 (d, 1H), 6.84 (m, 3H), 3.98 (s, 3H), 3.97 (s, 3H), 3.92 (s, 3H), 3.82 (m, 6H), 3.80 (s, 3H), 3.77 (d, 6H), 3.35 (q, 2H, J=5.8 Hz), 3.0–3.3 (m, 8H), 2.86 (q, 2H, J=5.4 Hz), 2.66 (d, 3H, J=4.5 Hz), 2.31 (m, 4H), 1.94 (quintet, 2H, J=6.2 Hz), 1.74 (m, 4H); MALDI-TOF-MS (monoisotopic), 1296.0 (1296.6 calc. for C$_{60}$H$_{78}$N$_{23}$O$_{11}$).

ImImOpPy-γ-ImPyPyPy-β-Dp-EDTA. Excess EDTA-dianhydride (50 mg) was dissolved in DMSOINMP (1 mL) and DIEA (1 mL) by heating at 55° C. for 5 min. The dianhydride solution was added to ImOpPy-γ-ImPyPyPy-β-NH$_2$ (13 mg, 10 μmol) dissolved in DMSO (750 μL). The mixture was heated (55° C., 25 min.) and the remaining EDTA-anhydride hydrolyzed (0.1M NaOH, 3 mL, 55° C., 10 min). Aqueous TFA (0.1% wt/v) was added to adjust the total volume to 8 mL and the solution purified directly by reversed phase HPLC to provide ImImOpPy-γ-ImPyPyPy-β-Dp-EDTA as a white powder upon lyophilization of the appropriate fractions (5.5 mg, 40% recovery). MALDI-TOF-MS (monoisotopic), 1570.9 (1570.7 calc. for C$_{70}$H$_{92}$N$_{25}$O$_{18}$).

ImImHpPy-γ-ImPyPyPy-β-Dp-EDTA. In order to remove the methoxy protecting group, a sample of ImImOpPy-γ-ImPyPyPy-β-Dp-EDTA (5 mg, 3.1 μmol) was treated with sodium thiophenoxide at 100° C. for 2 h. DMF (1000 μL) and thiophenol (500 μL) were placed in a (13×100 mm) disposable Pyrex screw cap culture tube. A 60% dispersion of sodium hydride in mineral oil (100 mg) was slowly added. Upon completion of the addition of the sodium hydride, ImImOpPy-γ-ImPyPyPy-β-Dp-EDTA (5 mg) dissolved in DMF (500 μL) was added. The solution was agitated, and placed in a 100° C. heat block, and deprotected for 2 h. Upon completion of the reaction the culture tube was cooled to 0° C., and 7 ml of a 20% (wt/v) solution of trifluoroacetic acid added. The aqueous layer is separated from the resulting biphasic solution and purified by reversed phase HPLC. ImImHpPy-γ-ImPyPyPy-β-Dp-EDTA is recovered as a white powder upon lyophilization of the appropriate fractions (3.2 mg, 72% recovery). UV (H$_2$O) $\lambda_{max}$ 246, 312 (66,000); MALDI-TOF-MS (monoisotopic), 1556.6 (1556.7 calc. for C$_{69}$H$_{90}$N$_{25}$O$_{18}$).

ImImPyPy-γ-ImOpPyPy-β-Dp-NH$_2$. ImImPyPy-γ-ImOpPyPy-β-Pam-Resin was synthesized in a stepwise fashion by machine-assisted solid phase methods from Boc-β-Pam-Resin (0.66 mmol/g). Baird, E. E. & Dervan, P. B. describes the solid phase synthesis of polyamides containing imidazole and pyrrole amino acids. *J. Am. Chem. Soc.* 118, 6141–6146 (1996); also see PCT US 97/003332. 3-hydroxypyrrole-Boc-amino acid (0.7 mmol) was incorporated by placing the amino acid (0.5 mmol) and HBTU (0.5 mmol) in a machine synthesis cartridge. Upon automated delivery of DMF (2 mL) and DIEA (1 mL) activation occurs. A sample of ImImPyPy-γ-ImOpPyPy-β-Pam-Resin (400 mg, 0.40 mmol/gram) was placed in a glass 20 mL peptide synthesis vessel and treated with neat 3,3'-diamino-N-methyldipropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImImPyPy-γ-ImOpPyPy-β-Dp-NH$_2$ is recovered upon lyophilization of the appropriate fractions as a white powder (104 mg, 54% recovery). UV (H$_2$O) $\lambda_{max}$ 246, 316 (66,000); MALDI-TOF-MS (monoisotopic), 1296.6 (1296.6 calc. for C$_{60}$H$_{78}$N$_{23}$O$_{11}$).

ImimPyPy-γ-ImOpPyPy-β-Dp-EDTA. Excess EDTA-dianhydride (50 mg) was dissolved in DMSOINMP (1 mL) and DIEA (1 mL) by heating at 55° C. for 5 min. The dianhydride solution was added to ImImPyPy-γ-ImOpPyPy-β-NH$_2$ (13 mg, 10 μmol) dissolved in DMSO (750 μL). The mixture was heated (55° C., 25 min.) and the remaining EDTA-anhydride hydrolyzed (0.1M NaOH, 3 mL, 55° C., 10 min). Aqueous TFA (0.1% wt/v) was added to adjust the total volume to 8 mL and the solution purified directly by reversed phase HPLC to provide ImImPyPy-γ-ImOpPyPy-β-Dp-EDTA as a white powder upon lyophilization of the appropriate fractions (5.9 mg, 42% recovery). MALDI-TOF-MS (monoisotopic), 1570.8 (1570.7 calc. for C$_{70}$H$_{92}$N$_{25}$O$_{18}$).

ImImPyPy-γ-ImHpPyPy-β-Dp-EDTA. In order to remove the methoxy protecting group, a sample of ImImPyPy-γ-ImOpPyPy-β-Dp-EDTA (5 mg, 3.1 μmol) was treated with sodium thiophenoxide at 100° C. for 2 h. DMF (1000 μL) and thiophenol (500 μL) were placed in a (13×100 mm) disposable Pyrex screw cap culture tube. A 60% dispersion of sodium hydride in mineral oil (100 mg) was slowly added. Upon completion of the addition of the sodium hydride, ImImPyPy-γ-ImOpPyPy-β-Dp-EDTA (5 mg) dissolved in DMF (500 μL) was added. The solution was agitated, and placed in a 100° C. heat block, and deprotected for 2 h. Upon completion of the reaction the culture tube was cooled to 0° C., and 7 ml of a 20% (wt/v) solution of trifluoroacetic acid added. The aqueous layer is separated from the resulting biphasic solution and purified by reversed phase HPLC. ImImPyPy-γ-ImHpPyPy-β-Dp-EDTA is recovered as a white powder upon lyophilization of the appropriate fractions (3.2 mg, 72% recovery). UV (H$_2$O)

$\lambda_{max}$ 246, 312 (66,000); MALDI-TOF-MS (monoisotopic), 1555.9 (1556.7 calc. for $C_{69}H_{90}N_{25}O_{18}$).

EXAMPLE 6

Determination of Polyamide Binding Orientation

Affinity cleavage experiments using hairpin polyamides modified with EDTA·Fe(II) at either the C-terminus or on the γ-turn, were used to determine polyamide binding orientation and stoichiometry. The results of affinity cleavage experiments are consistent only with recognition of 6-bp by an 8-ring hairpin complex and rule out any extended 1:1 or overlapped complex formation. In addition, affinity cleavage experiments reveal hairpin formation supporting the claim that it is the Hp/Py and Py/Hp pairing which form at both match and mismatch sites to discriminate A·T from T·A.

Affinity cleavage reactions were executed in a total volume of 40 μL. A stock solution of polyamide or $H_2O$ was added to a solution containing labeled restriction fragment (20,000 cpm), affording final solution conditions of 25 mM Tris-Acetate, 20 mM NaCl, 100 μM/bp calf thymus DNA, and pH 7.0. Solutions were incubated for a minimum of 4 hours at 22° C. Subsequently, 4 μL of freshly prepared 100 μM $Fe(NH_4)_2(SO_4)_2$ was added and the solution allowed to equilibrate for min. Cleavage reactions were initiated by the addition of 4 μL of 100 mM dithiothreitol, allowed to proceed for 30 min at 22° C., then stopped by the addition of 10 μL of a solution containing 1.5 M NaOAc (pH 5.5), 0.28 mg/mL glycogen, and 14 μM base pairs calf thymus DNA, and ethanol precipitated. The reactions were resuspended in 1×TBE/80% formamide loading buffer, denatured by heating at 85° C. for 15 min, and placed on ice. The reaction products were separated by electrophoresis on an 8% polyacrylamide gel (5% cross-link, 7 M urea) in 1×TBE at 2000 V for 1.5 hours. Gels were dried and exposed to a storage phosphor screen. Relative cleavage intensities were determined by volume integration of individual cleavage bands using ImageQuant software.

EXAMPLE 7

Improvement to Polyamide Sequence Specificity

The polyamides of this invention provide improved specificity relative to existing polyamide technology. Turner, J. T., Baird, E. E., and Dervan, P. B. describe the recognition of seven base pair sequences in the minor groove of DNA by ten-ring pyrrole-imidazole polyamide hairpins *J. Am. Chem. Soc.* 1997 119, 7636. For example, quantitative DNaseI footprint titrations reveal that the 10-ring hairpin ImPyPyPyPy-γ-ImPyPyPyPy-β-Dp binds a 5'-TGTAACA-3-sequence with an equlibrium dissociation constant of 0.083 nM, and 18-fold specificity versus a single base mismatch site. A number of other sites are also bound on the 252-bp DNA fragment used for the footprint titration experiments. (FIG. 13). Introduction of a Hp/Py and Py/Hp pair in the 10-ring polyamide, ImHpPyPyPy-γ-ImHpPyPyPy-β-Dp, to recognize a TEA and APT within the 7-bp target sequence, increases the sequence-specificty. For example, a single base mismatch site 5'-TGGAACA-3 is discriminated by >5000-fold (FIG. 13, Table 8). In fact all 245 7-bp mismatch sites present on the restriction fragment are discriminated >5000-fold by the polyamide ImHpPyPyPy-γ-ImHpPyPyPy-β-Dp (FIG. 13). For cases where three A,T base pairs are present in succession it is preferred to substitute Py/Py in place of at least one Hp/Py or Py/Hp to provide for recognition of A·T and T·A at a single position.

TABLE 8

Equilibrium dissociation constants*

| Polyamide† | 5'-TGGTCA-3' | 5'-TGGACA-3' | $K_{rel}$‡ |
|---|---|---|---|
| Py/Py | 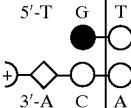 $K_d$ = 0.083 nM | 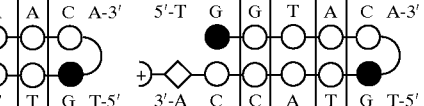 $K_d$ = 1.5 nM | 18 |
| Hp/Py | 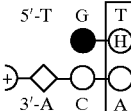 $K_d$ = 0.2 nM | 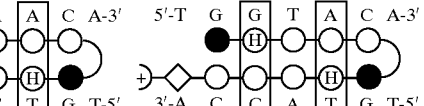 $K_d$ > 1000 nM | >5000 |

*The reported dissociation constants are the average values obtained from three DNase I footprint titration experiments. The standard deviation for each data set is less than 15% of the reported number. Assays were carried out in the presence of 10 mM Tris · HCl, 10 mM KCl, 10 mM MgCl2, and 5 mM CaCl2 at pH 7.0 and 22° C.
†Ring pairing opposite T · A and A · T in the fourth position.
‡Calculated as $K_d$(5'-TGGTACA-3')/$K_d$(5'-TGTAACA-3').

EXAMPLE 8

Use of Pairing Code

There are 256 possible four base pair combinations of A, T, G, and C. Of these, there are a possible 240 four base pair sequences which contain at least 1 A·T or T·A base pair and therefore can advantageously use an Hp/Py, or Py/Hp carboxamide binding. Polyamides binding to any of these sequences can be designed in accordance with the code of TABLE 2. Table 9 lists the sixteen eight-ring hairpin polyamides (1–16) which recognize the sixteen 5'-WGTNNW-3' sequences (W=A or T, X=A, G, C, or T). Table 10 lists the sixteen eight-ring hairpin polyamides (17–32) which recognize the sixteen 5'-WGANNW-3' sequences (17–32). Table 11 lists the twelve eight-ring hairpin polyamides (33–44) which recognize twelve 5'-WGGNNW-3' sequences which contain at least one A,T base pair. Table 11 lists the four eight-ring hairpin polyamides (G1–G4) which target the four 5'-WGGNNW-3' sequences (G1–G4) which contain exclusively G·C base pairs. Table 12 lists the twelve eight-ring hairpin polyamides (45–56) which recognize twelve 5'-WGCNNW-3' sequences which contain at least one A,T base pair. Table 12 lists the four eight-ring hairpin polyamides (G5–G8) which target the four 5'-WGCNNW-3' sequences (G5–G8) which contain exclusively G·C base pairs. Table 13 lists the sixteen eight-ring hairpin polyamides (57–72) which recognize the sixteen 5'-WTTNNW-3' sequences (57–72). Table 14 lists the sixteen eight-ring hairpin polyamides (73–88) which recognize the sixteen 5'-WTANNW-3' sequences (73–88); Table 15 lists the sixteen eight-ring hairpin polyamides (89–104) which recognize the sixteen 5'-WTGNNW-3' sequences (89–104). Table 16 lists the sixteen eight-ring hairpin polyamides (105–120) which recognize the sixteen 5'-WTCNNW-3' sequences (105–120). Table 17 lists the sixteen eight-ring hairpin polyamides (121–136) which recognize the sixteen 5'-WATNNW-3' sequences (121–136). Table 18 lists the sixteen eight-ring hairpin polyamides (137-f52) which recognize the sixteen 5'-WAANNW-3' sequences (137–152). Table 19 lists the sixteen eight-ring hairpin polyamides (153–168) which recognize the sixteen 5'-WAGNNW-3' sequences (153–168). Table 20 lists the sixteen eight-ring hairpin polyamides (169–184) which recognize the sixteen 5'-WACNNW-3' sequences (169–184). Table 21 lists the sixteen eight-ring hairpin polyamides (185–200) which recognize the sixteen 5'-WCTNNW-3' sequences (185–200). Table 22 lists the sixteen 7 eight-ring hairpin polyamides (201–216) which recognize the sixteen 5'-WCANNW-3' sequences (201–216). Table 23 lists the twelve eight-ring hairpin polyamides (217–228) which recognize the twelve 5'-WCGNNW-3' sequences which contain at least one A,T base pair. Table 23 lists the four eight-ring hairpin polyamides (G9–G12) which target the four 5'-WCGNNW-3' sequences (G9–G12) which contain exclusively C·G base pairs. Table 24 lists the twelve eight-ring hairpin polyamides (229–240) which recognize the twelve 5'-WCCNNW-3' sequences which contain at least one A,T base pair. Table 24 lists the four eight-ring hairpin polyamides (G13–G16) which target the four 5'-WCCNNW-3' sequences (G13–G16) which contain exclusively C·G base pairs.

TABLE 9

8-ring Hairpin Polyamides for recognition of 6-bp 5'-WGTNNW-3'

| DNA sequence | aromatic amino acid sequence |
|---|---|
| 1) 5'-W G T T T W-3' | 1) ImHpHpHp-γ-PyPyPyPy |
| 2) 5'-W G T T A W-3' | 2) ImHpHpPy-γ-HpPyPyPy |
| 3) 5'-W G T T G W-3' | 3) ImHpHpIm-γ-PyPyPyPy |
| 4) 5'-W G T T C W-3' | 4) ImHpHpPy-γ-ImPyPyPy |
| 5) 5'-W G T A T W-3' | 5) ImHpPyHp-γ-PyPyHpPy |
| 6) 5'-W G T A A W-3' | 6) ImHpPyPy-γ-HpPyHpPy |
| 7) 5'-W G T A G W-3' | 7) ImHpPyIm-γ-PyPyHpPy |
| 8) 5'-W G T A C W-3' | 8) ImHpPyPy-γ-ImPyHpPy |
| 9) 5'-W G T G T W-3' | 9) ImHpImHp-γ-PyPyPyPy |
| 10) 5'-W G T G A W-3' | 10) ImHpImPy-γ-HpPyPyPy |
| 11) 5'-W G T G G W-3' | 11) ImHpImIm-γ-PyPyPyPy |
| 12) 5'-W G T G C W-3' | 12) ImHpImPy-γ-ImPyPyPy |
| 13) 5'-W G T C T W-3' | 13) ImHpPyHp-γ-PyImPyPy |
| 14) 5'-W G T C A W-3' | 14) ImHpPyPy-γ-HpImPyPy |

TABLE 9-continued 8-ring Hairpin Polyamides for recognition of 6-bp 5'-WGTNNW-3'

| DNA sequence | aromatic amino acid sequence |
|---|---|
| 15) 5'-W G T C G W-3' | 15) ImHpPyIm-γ-PyImPyPy |
| 16) 5'-W G T C C W-3' | 16) ImHpPyPy-γ-ImImPyPy |

TABLE 10

8-ring Hairpin Polyamides for recognition of 6-bp 5'-WGANNW-3'

| DNA sequence | aromatic amino acid sequence |
|---|---|
| 17) 5'-W G A T T W-3' | 17) ImPyHpHp-γ-PyPyHpPy |
| 18) 5'-W G A T A W-3' | 18) ImPyHpPy-γ-HpPyHpPy |
| 19) 5'-W G A T G W-3' | 19) ImPyHpIm-γ-PyPyHpPy |
| 20) 5'-W G A T C W-3' | 20) ImPyHpPy-γ-ImPyHpPy |
| 21) 5'-W G A A T W-3' | 21) ImPyPyHp-γ-PyHpHpPy |
| 22) 5'-W G A A A W-3' | 22) ImPyPyPy-γ-HpHpHpPy |
| 23) 5'-W G A A G W-3' | 23) ImPyPyIm-γ-PyHpHpPy |
| 24) 5'-W G A A C W-3' | 24) ImPyPyPy-γ-ImHpHpPy |
| 25) 5'-W G A G T W-3' | 25) ImPyImHp-γ-PyPyHpPy |
| 26) 5'-W G A G A W-3' | 26) ImPyImPy-γ-HpPyHpPy |
| 27) 5'-W G A G G W-3' | 27) ImPyImIm-γ-PyPyHpPy |
| 28) 5'-W G A G C W-3' | 28) ImPyImPy-γ-ImPyHpPy |
| 29) 5'-W G A C T W-3' | 29) ImPyPyHp-γ-PyImHpPy |
| 30) 5'-W G A C A W-3' | 30) ImPyPyPy-γ-HpImHpPy |
| 31) 5'-W G A C G W-3' | 31) ImPyPyIm-γ-PyImHpPy |
| 32) 5'-W G A C C W-3' | 32) ImPyPyPy-γ-ImImHpPy |

TABLE 11

8-ring Hairpin Polyamides for recognition of 6-bp 5'-WGGNNW-3'

| DNA sequence | aromatic amino acid sequence |
|---|---|
| 33) 5'-W G G T T W-3' | 33) ImImHpHp-γ-PyPyPyPy |
| 34) 5'-W G G T A W-3' | 34) ImImHpPy-γ-HpPyPyPy |
| 35) 5'-W G G T G W-3' | 35) ImImHpIm-γ-PyPyPyPy |
| 36) 5'-W G G T C W-3' | 36) ImImHpPy-γ-ImPyPyPy |
| 37) 5'-W G G A T W-3' | 37) ImImPyHp-γ-PyHpPyPy |
| 38) 5'-W G G A A W-3' | 38) ImImPyPy-γ-HpHpPyPy |
| 39) 5'-W G G A G W-3' | 39) ImImPyIm-γ-PyHpPyPy |
| 40) 5'-W G G A C W-3' | 40) ImImPyPy-γ-ImHpPyPy |
| 41) 5'-W G G T W-3' | 41) ImImImHp-γ-PyPyPyPy |
| 42) 5'-W G G G A W-3' | 42) ImImImPy-γ-HpPyPyPy |
| 43) 5'-W G G C T w-3' | 43) ImImPyHp-γ-PyImPyPy |
| 44) 5'-W G G C A W-3' | 44) ImImPyPy-γ-HpImPyPy |
| G1) 5'-W G G G G W-3' | G1) ImImImIm-γ-PyPyPyPy |
| G2) 5'-W G G G C W-3' | G2) ImImImPy-γ-ImPyPyPy |
| G3) 5'-W G G C G W-3' | G3) ImImPyIm-γ-PyImPyPy |
| G4) 5'-W G G C C W-3' | G4) ImImPyPy-γ-ImImPyPy |

TABLE 12

8-ring Hairpin Polyamides for recognition of 6-bp 5'-WGCNNW-3'

| DNA sequence | aromatic amino acid sequence |
|---|---|
| 45) 5'-W G C T T W-3' | 45) ImPyHpHp-γ-PyPyImPy |
| 46) 5'-W G C T A W-3' | 46) ImPyHpPy-γ-HpPyImPy |
| 47) 5'-W G C T G W-3' | 47) ImPyHpIm-γ-PyPyImPy |
| 48) 5'-W G C T C W-3' | 48) ImPyHpPy-γ-ImPyImPy |
| 49) 5'-W G C A T W-3' | 49) ImPyPyHp-γ-PyHpImPy |
| 50) 5'-W G C A A W-3' | 50) ImPyPyPy-γ-HpHpImPy |
| 51) 5'-W G C A G W-3' | 51) ImPyPyIm-γ-PyHpImPy |
| 52) 5'-W G C A C W-3' | 52) ImPyPyPy-γ-ImHpImPy |
| 53) 5'-W G C G T W-3' | 53) ImPyImHp-γ-PyPyImPy |
| 54) 5'-W G C G A W-3' | 54) ImOyImPy-γ-HpPyImPy |
| 55) 5'-W G C C T W-3' | 55) ImPyPyHp-γ-PyImImPy |

TABLE 12-continued 8-ring Hairpin Polyamides for recognition of 6-bp 5'-WGCNNW-3'

| DNA sequence | aromatic amino acid sequence |
|---|---|
| 56) 5'-W G C C A W-3' | 56) ImPyPyPy-γ-HpImImPy |
| G5) 5'-W G C G G W-3' | G5) ImPyImIm-γ-PyPyImPy |
| G6) 5'-W G C G C W-3' | G6) ImPyImPy-γ-ImPyImPy |
| G7) 5'-W G C C G W-3' | G7) ImPyPyIm-γ-PyImImPy |
| G8) 5'-W G C C C W-3' | G8) ImPyPyPy-γ-ImImImPy |

TABLE 13

8-ring Hairpin Polyamides for recognition of 6-bp 5'-WTTNNW-3'

| DNA sequence | aromatic amino acid sequence |
|---|---|
| 57) 5'-W T T T T W-3' | 57) HpHpHpHp-γ-PyPyPyPy |
| 58) 5'-W T T T A W-3' | 58) HpHpHpPy-γ-HpPyPyPy |
| 59) 5'-W T T T G W-3' | 59) HPHpHpIm-γ-PyPyPyPy |
| 60) 5'-W T T T C W-3' | 60) HpHpHpPy-γ-ImPyPyPy |
| 61) 5'-W T T A T W-3' | 61) HpHpPyHp-γ-PyHpPyPy |
| 62) 5'-W T T A A W-3' | 62) HpHpPyPy-γ-HpHpPyPy |
| 63) 5'-W T T A G W-3' | 63) HpHpPyIm-γ-PyHpPyPy |
| 64) 5'-W T T A C W-3' | 64) HpHpPyPy-γ-ImHpPyPy |
| 65) 5'-W T T G T W-3' | 65) HpHpImHp-γ-PyPyPyPy |
| 66) 5'-W T T G A W-3' | 66) HpHpImPy-γ-HpPyPyPy |
| 67) 5'-W T T G G W-3' | 67) HpHpImIm-γ-PyPyPyPy |
| 68) 5'-W T T G C W-3' | 68) HpHpImPy-γ-ImPyPyPy |
| 69) 5'-W T T C T W-3' | 69) HpHpPyHp-γ-PyImPyPy |
| 70) 5'-W T T C A W-3' | 70) HpHpPyPy-γ-HpImPyPy |
| 71) 5'-W T T C G W-3' | 71) HpHpPyIm-γ-PyImPyPy |
| 72) 5'-W T T C C W-3' | 72) HpHpPyPy-γ-ImImPyPy |

TABLE 14

8-ring Hairpin Polyamides for recognition of 6-bp 5'-WTANNW-3'

| DNA sequence | aromatic amino acid sequence |
|---|---|
| 73) 5'-W T A T T W-3' | 73) HpPyHpHp-γ-PyPyHpPy |
| 74) 5'-W T A T A W-3' | 74) HpPyHpPy-γ-HpPyHpPy |
| 75) 5'-W T A T G W-3' | 75) HpPyHpIm-γ-PyPyHpPy |
| 76) 5'-W T A T C W-3' | 76) HpPyHpPy-γ-ImPyHpPy |
| 77) 5'-W T A A T W-3' | 77) HpPyPyHp-γ-PyHpHpPy |
| 78) 5'-W T A A A W-3' | 78) HpPyPyPy-γ-HpHpHpPy |
| 79) 5'-W T A A G W-3' | 79) HpPyPyIm-γ-PyHpHpPy |
| 80) 5'-W T A A C W-3' | 80) HpPyPyPy-γ-ImHpHpPy |
| 81) 5'-W T A G T W-3' | 81) HpPyImHp-γ-PyPyHpPy |
| 82) 5'-W T A G A W-3' | 82) HpPyImPy-γ-HpPyHpPy |
| 83) 5'-W T A G G W-3' | 83) HpPyImIm-γ-PyPyHpPy |
| 84) 5'-W T A G C W-3' | 84) HpPyImPy-γ-ImPyHpPy |
| 85) 5'-W T A C T W-3' | 85) HpPyPyHp-γ-PyImHpPy |
| 86) 5'-W T A C A W-3' | 86) HpPyPyPy-γ-HpImHpPy |
| 87) 5'-W T A C G W-3' | 87) HpPyPyIm-γ-PyImHpPy |
| 88) 5'-W T A C C W-3' | 88) HpPyPyPy-γ-ImImHpPy |

TABLE 15

8-ring Hairpin Polyamides for recognition of 6-bp 5'-WTGNNW-3'

| DNA sequence | aromatic amino acid sequence |
|---|---|
| 89) 5'-W T G T T W-3' | 89) HpImHpHp-γ-PyPyPyPy |
| 90) 5'-W T G T A W-3' | 90) HpImHpPy-γ-HpPyPyPy |
| 91) 5'-W T G T G W-3' | 91) HpImHpIm-γ-PyPyPyPy |
| 92) 5'-W T G T C W-3' | 92) HpImHpPy-γ-ImPyPyPy |
| 93) 5'-W T G A T W-3' | 93) HpImPyHp-γ-PyHpPyPy |
| 94) 5'-W T G A A W-3' | 94) HpImPyPy-γ-HpHpPyPy |
| 95) 5'-W T G A G W-3' | 95) HpImPyIm-γ-PyHpPyPy |
| 96) 5'-W T G A C W-3' | 96) HpImPyPy-γ-ImHpPyPy |
| 97) 5'-W T G G T W-3' | 97) HpImImHp-γ-PyPyPyPy |
| 98) 5'-W T G G A W-3' | 98) HpImImPy-γ-HpPyPyPy |
| 99) 5'-W T G C T W-3' | 99) HpImPyHp-γ-PyImPyPy |
| 100) 5'-W T G C A W-3' | 100) HpImPyPy-γ-HpImPyPy |
| 101) 5'-W T G G G W-3' | 101) HpImImIm-γ-ImPyPyPy |
| 102) 5'-W T G G C W-3' | 102) HpImImPy-γ-ImPyPyPy |
| 103) 5'-W T G C G W-3' | 103) HpImPyIm-γ-PyImPypy |
| 104) 5'-W T G C C W-3' | 104) HpImPyPy-γ-ImImPyPy |

TABLE 16

8-ring Hairpin Polyamides for recognition of 6-bp 5'-WTCNNW-3'

| DNA sequence | aromatic amino acid sequence |
|---|---|
| 105) 5'-W T C T T W-3' | 105) HpPyHpHp-γ-PyPyImPy |
| 106) 5'-W T C T A W-3' | 106) HpPyHpPy-γ-HpPyImPy |
| 107) 5'-W T C T G W-3' | 107) HpPyHpIm-γ-PyPyImPy |
| 108) 5'-W T C T C W-3' | 108) HpPyHpPy-γ-ImPyImPy |
| 109) 5'-W T C A T W-3' | 109) HpPyPyHp-γ-PyHpImPy |
| 110) 5'-W T C A A W-3' | 110) HpPyPyPy-γ-HpHpImPy |
| 111) 5'-W T C A G W-3' | 111) HpPyPyIm-γ-PyHpImPy |
| 112) 5'-W T C A C W-3' | 112) HpPyPyPy-γ-ImHpImPy |
| 113) 5'-W T C G T W-3' | 113) HpPyImHp-γ-PyPyImPy |
| 114) 5'-W T C G A W-3' | 114) HpPyImPy-γ-HpPyImPy |
| 115) 5'-W T C C T W-3' | 115) HpPyPyHp-γ-PyImImPy |
| 116) 5'-W T C C A W-3' | 116) HpPyPyPy-γ-HpImImPy |
| 117) 5'-W T C G G W-3' | 117) HpPyImIm-γ-PyPyImPy |
| 118) 5'-W T C G C W-3' | 118) HpPyImPy-γ-ImPyImPy |
| 119) 5'-W T C C G W-3' | 119) HpPyPyIm-γ-PyImImPy |
| 120) 5'-W T C C C W-3' | 120) HpPyPyPy-γ-ImImImPy |

TABLE 17

8-ring Hairpin Polyamides for recognition of 6-bp 5'-WATNNW-3'

| DNA sequence | aromatic amino acid sequence |
|---|---|
| 121) 5'-W A T T T W-3' | 121) PyHpHpHp-γ-PyPyPyHp |
| 122) 5'-W A T T A W-3' | 122) PyHpHpPy-γ-HpPyPyHp |
| 123) 5'-W A T T G W-3' | 123) PyHpHpIm-γ-PyPyPyHp |
| 124) 5'-W A T T C W-3' | 124) PyHpHpPy-γ-ImPyPyHp |
| 125) 5'-W A T A T W-3' | 125) PyHpPyHp-γ-PyHpPyHp |
| 126) 5'-W A T A A W-3' | 126) PyHpPyPy-γ-HpHpPyHp |
| 127) 5'-W A T A G W-3' | 127) PyHpPyIm-γ-PyHpPyHp |
| 128) 5'-W A T A C W-3' | 128) PyHpPyPy-γ-ImHpPyHp |
| 129) 5'-W A T G T W-3' | 129) PyHpImHp-γ-PyPyPyHp |
| 130) 5'-W A T G A W-3' | 130) PyHpImPy-γ-HpPyPyHp |
| 131) 5'-W A T G G W-3' | 131) PyHpImIm-γ-PyPyPyHp |
| 132) 5'-W A T G C W-3' | 132) PyHpImPy-γ-ImPyPyHp |
| 133) 5'-W A T C T W-3' | 133) PyHpPyHp-γ-PyImPyHp |
| 134) 5'-W A T C A W-3' | 134) PyHpPyPy-γ-HpImPyHp |
| 135) 5'-W A T C G W-3' | 135) PyHpPyIm-γ-PyImPyHp |
| 136) 5'-W A T C C W-3' | 136) PyHpPyPy-γ-ImImPyHp |

TABLE 18

8-ring Hairpin Polyamides for recognition of 6-bp 5'-WAANNW-3'

| DNA sequence | aromatic amino acid sequence |
|---|---|
| 137) 5'-W A A T T W-3' | 137) PyPyHpHp-γ-PyPyHpHp |
| 138) 5'-W A A T A W-3' | 138) PyPyHpPy-γ-HpPyHpHp |
| 139) 5'-W A A T G W-3' | 139) PyPyHpIm-γ-PyPyHpHp |
| 140) 5'-W A A T C W-3' | 140) PyPyHpPy-γ-ImPyHpHp |
| 141) 5'-W A A A T W-3' | 141) PyPyPyHp-γ-PyHpHpHp |
| 142) 5'-W A A A A W-3' | 142) PyPyPyPy-γ-HpHpHpHp |
| 143) 5'-W A A A G W-3' | 143) PyPyPyIm-γ-PyHpHpHp |
| 144) 5'-W A A A C W-3' | 144) PyPyPyPy-γ-ImHpHpHp |
| 145) 5'-W A A G T W-3' | 145) PyPyImHp-γ-PyPyHpHp |
| 146) 5'-W A A G A W-3' | 146) PyPyImPy-γ-HpPyHpHp |
| 147) 5'-W A A G G W-3' | 147) PyPyImIm-γ-PyPyHpHp |
| 148) 5'-W A A G C W-3' | 148) PyPyImPy-γ-ImPyHpHp |
| 149) 5'-W A A C T W-3' | 149) PyPyPyHp-γ-PyImHpHp |
| 150) 5'-W A A C A W-3' | 150) PyPyPyPy-γ-HpImHpHp |

TABLE 18-continued 8-ring Hairpin Polyamides for recognition of 6-bp 5'-WAANNW-3'

| DNA sequence | aromatic amino acid sequence |
|---|---|
| 151) 5'-W A A C G W-3' | 151) PyPyPyIm-γ-PyImHpHp |
| 152) 5'-W A A C C W-3' | 152) PyPyPyPy-γ-ImImHpHp |

TABLE 19

8-ring Hairpin Polyamides for recognition of 6-bp 5'-WAGNNW-3'

| DNA sequence | aromatic amino acid sequence |
|---|---|
| 153) 5'-W A G T T W-3' | 153) PyImHpHp-γ-PyPyPyHp |
| 154) 5'-W A G T A W-3' | 154) PyImHpPy-γ-HpPyPyHp |
| 155) 5'-W A G T G W-3' | 155) PyImHpIm-γ-PyPyPyHp |
| 156) 5'-W A G T C W-3' | 156) PyImHpPy-γ-ImPyPyHp |
| 157) 5'-W A G A T W-3' | 157) PyImPyHp-γ-PyHpPyHp |
| 158) 5'-W A G A A W-3' | 158) PyImPyPy-γ-HpHpPyHp |
| 159) 5'-W A G A G W-3' | 159) PyImPyIm-γ-PyHpPyHp |
| 160) 5'-W A G A C W-3' | 160) PyImPyPy-γ-ImHpPyHp |
| 161) 5'-W A G G T W-3' | 161) PyImImHp-γ-PyPyPyHp |
| 162) 5'-W A G G A W-3' | 162) PyImImPy-γ-HpPyPyHp |
| 163) 5'-W A G C T W-3' | 163) PyImPyHp-γ-PyImPyHp |
| 164) 5'-W A G C A W-3' | 164) PyImPyPy-γ-HpImPyHp |
| 165) 5'-W A G G G W-3' | 165) PyImImIm-γ-PyPyPyHp |
| 166) 5'-W A G G C W-3' | 166) PyImImPy-γ-ImPyPyHp |
| 167) 5'-W A G C G W-3' | 167) PyImPyIm-γ-PyImPyHp |
| 168) 5'-W A G C C W-3' | 168) PyImPyPy-γ-ImImPyHp |

TABLE 20

8-ring Hairpin Polyamides for recognition of 6-bp 5'-WACNNW-3'

| DNA sequence | aromatic amino acid sequence |
|---|---|
| 169) 5'-W A C T T W-3' | 169) PyPyHpHp-γ-PyPyImHp |
| 170) 5'-W A C T A W-3' | 170) PyPyHpPy-γ-HpPyImHp |
| 171) 5'-W A C T G W-3' | 171) PyPyHpIm-γ-PyPyImHp |
| 172) '-W A C T C W-3' | 172) PyPyHpPy-γ-ImPyImHp |
| 173) 5'-W A C A T W-3' | 173) PyPyPyHp-γ-PyHpImHp |
| 174) 5'-W A C A A W-3' | 174) PyPyPyPy-γ-HpHpImHp |
| 175) 5'-W A C A G W-3' | 175) PyPyPyIm-γ-PyHpImHp |
| 176) 5'-W A C A C W-3' | 176) PyPyPyPy-γ-ImHpImHp |
| 177) 5'-W A C G T W-3' | 177) PyPyImHp-γ-PyPyImHp |

TABLE 20-continued 8-ring Hairpin Polyamides for recognition of 6-bp 5'-WACNNW-3'

| DNA sequence | aromatic amino acid sequence |
| --- | --- |
| 178) 5'-W A C G A W-3' | 178) PyPyImPy-γ-HpPyImHp |
| 179) 5'-W A C C T W-3' | 179) PyPyPyHp-γ-PyImImHp |
| 180) 5'-W A C C A W-3' | 180) PyPyPyPy-γ-HpImImHp |
| 181) 5'-W A C G G W-3' | 181) PyPyImIm-γ-PyPyImHp |
| 182) 5'-W A C G C W-3' | 182) PyPyImPy-γ-ImPyImHp |
| 183) 5'-W A C C G W-3' | 183) PyPyPyIm-γ-PyImImHp |
| 184) 5'-W A C C C W-3' | 184) PyPyPyPy-γ-ImImImH |

TABLE 21

8-ring Hairpin Polyamides for recognition of 6-bp 5'-WCTNNW-3'

| DNA sequence | aromatic amino acid sequence |
| --- | --- |
| 185) 5'-W C T T T W-3' | 185) PyHpHpHp-γ-PyPyPyIm |
| 186) 5'-W C T T A W-3' | 186) PyHpHpPy-γ-HpPyPyIm |
| 187) 5'-W C T T G W-3' | 187) PyHpHpIm-γ-PyPyPyIm |
| 188) 5'-W C T T C W-3' | 188) PyHpHpPy-γ-ImPyPyIm |
| 189) 5'-W C T A T W-3' | 189) PyHpPyHp-γ-PyHpPyIm |
| 190) 5'-W C T A A W-3' | 190) PyHpPyPy-γ-HpHpPyIm |
| 191) 5'-W C T A G W-3' | 191) PyHpPyIm-γ-PyHpPyIm |
| 192) 5'-W C T A C W-3' | 192) PyHpPyPy-γ-ImHpPyIm |
| 193) 5'-W C T G T W-3' | 193) PyHpImHp-γ-PyPyPyIm |
| 194) 5'-W C T G A W-3' | 194) PyHpImPy-γ-HpPyPyIm |
| 195) 5'-W C T G G W-3' | 195) PyHpImIm-γ-PyPyPyIm |
| 196) 5'-W C T G C W-3' | 196) PyHpImPy-γ-ImPyPyIm |
| 197) 5'-W C T C T W-3' | 197) PyHpPyHp-γ-PyImPyIm |
| 198) 5'-W C T C A W-3' | 198) PyHpPyPy-γ-HpImPyIm |
| 199) 5'-W C T C G W-3' | 199) PyHpPyIm-γ-PyImPyIm |
| 200) 5'-W C T C C W-3' | 200) PyHpPyPy-γ-ImImPyIm |

TABLE 22

8-ring Hairpin Polyamides for recognition of 6-bp 5'-WCANNW-3'

| DNA sequence | aromatic amino acid sequence |
| --- | --- |
| 201) 5'-W C A T T W-3' | 201) PyPyHpHp-γ-PyPyHpIm |
| 202) 5'-W C A T A W-3' | 202) PyPyHpPy-γ-HpPyHpIm |
| 203) 5'-W C A T G W-3' | 203) PyPyHpIm-γ-PyPyHpIm |
| 204) 5'-W C A T C W-3' | 204) |

TABLE 22-continued 8-ring Hairpin Polyamides for recognition of 6-bp 5'-WCANNW-3'

| DNA sequence | aromatic amino acid sequence |
| --- | --- |
| 205) 5'-W C A T C W-3' | 205) PyPyHpPy-γ-ImPyHpIm |
| 206) 5'-W C A A T W-3' | 206) PyPyPYHp-γ-PyHpHpIm |
| 207) 5'-W C A A A W-3' | 207) PyPyPyPy-γ-HpHpHpIm |
| 208) 5'-W C A A G W-3' | 208) PyPyPyIm-γ-PyHpHpIm |
| 209) 5'-W C A A C W-3' | 209) PyPyPyPy-γ-ImHpHpIm |
| 210) 5'-W C A G T W-3' | 210) PyPyImHp-γ-PyPyHpIm |
| 211) 5'-W C A G A W-3' | 211) PyPyImPy-γ-HpPyHpIm |
| 212) 5'-W C A G G W-3' | 212) PyPyImIm-γ-PyPyHpIm |
| 213) 5'-W C A G C W-3' | 213) PyPyImPy-γ-ImPyHpIm |
| 214) 5'-W C A C T W-3' | 214) PyPyPyHp-γ-PyImHpIm |
| 215) 5'-W C A C A W-3' | 215) PyPYPyPy-γ-HpImHpIm |
| 216) 5'-W C A C G W-3' | 216) PyPyPyIm-γ-PyImHpIm |
| 5'-W C A C C W-3' | PyPyPyPy-γ-ImImHpIm |

TABLE 23

8-ring Hairpin Polyamides for recognition of 6-bp 5'-WCGNNW-3'

| DNA sequence | aromatic amino acid sequence |
| --- | --- |
| 217) 5'-W C G T T W-3' | 217) PyImHpHp-γ-PyPyPyIm |
| 218) 5'-W C G T A W-3' | 218) PyImHpPy-γ-HpPyPyIm |
| 219) 5'-W C G T G W-3' | 219) PyImHpIm-γ-PyPyPyIm |
| 220) 5'-W C G T C W-3' | 220) PyImHpPy-γ-ImPyPyIm |
| 221) 5'-W C G A T W-3' | 221) PyImPyHp-γ-PyHpPyIm |
| 222) 5'-W C G A A W-3' | 222) PyImPyPy-γ-HpHpPyIm |
| 223) 5'-W C G A G W-3' | 223) PyImPyIm-γ-PyHpPyIm |
| 224) 5'-W C G A C W-3' | 224) PyImPyPy-γ-ImHpPyIm |
| 225) 5'-W C G G T W-3' | 225) PyImImHp-γ-PyPyPyIm |
| 226) 5'-W C G G A W-3' | 226) PyImImPy-γ-HpPyPyIm |
| 227) 5'-W C G G C W-3' | 227) PyImPyHp-γ-PyImPyIm |
| 228) 5'-W C G C A W-3' | 228) PyImPyPy-γ-HpImPyIm |
| G9) 5'-W C G G G W-3' | G9) PyImImIm-γ-PyPyPyIm |
| G10) 5'-W C G G C W-3' | G10) PyImImPy-γ-ImPyPyIm |
| G11) 5'-W C G C G W-3' | G11) PyImPyIm-γ-PyImPyIm |
| G12) 5'-W C G C C W-3' | G12) PyImPyPy-γ-ImImPyIm |

TABLE 24

8-ring Hairpin Polyamides for recognition of 6-bp 5'-WCCNNW-3'

| DNA sequence | aromatic amino acid sequence |
|---|---|
| 229)<br>5'-W C C T T W-3' | 229)<br>PyPyHpHp-γ-PyPyImIm |
| 230)<br>5'-W C C T A W-3' | 230)<br>PyPyHpPy-γ-HpPyImIm |
| 231)<br>5'-W C C T G W-3' | 231)<br>PyPyHpIm-γ-PyPyImIm |
| 232)<br>5'-W C C T C W-3' | 232)<br>PyPyHpPy-γ-ImPyImIm |
| 233)<br>5'-W C C A T W-3' | 233)<br>PyPyPyHp-γ-PyHpImIm |
| 234)<br>5'-W C C A A W-3' | 234)<br>PyPyPyPy-γ-HpHpImIm |
| 235)<br>5'-W C C A G W-3' | 235)<br>PyPyPyIm-γ-PyHpImIm |
| 236)<br>5'-W C C A C W-3' | 236)<br>PyPyPyPy-γ-ImHpImIm |
| 237)<br>5'-W C C G T W-3' | 237)<br>PyPyImHp-γ-PyPyImIm |
| 238)<br>5'-W C C G A W-3' | 238)<br>PyPyImPy-γ-HpPyImIm |
| 239)<br>5'-W C C C T W-3' | 239)<br>PyPyPyHp-γ-PyImImIm |
| 240)<br>5'-W C C C A W-3' | 240)<br>PyPyPyPy-γ-HpImImIm |
| G13)<br>5'-W C C G G W-3' | G13)<br>PyPyImIm-γ-PyPyImIm |
| G14)<br>5'-W C C G C W-3' | G14)<br>PyPyImPy-γ-ImPyImIm |
| G15)<br>5'-W C C C G W-3' | G15)<br>PyPyPyIm-γ-PyImImIm |
| G16)<br>5'-W C C C C W-3' | G16)<br>PyPyPyPy-γ-ImImImIm |

EXAMPLE 9

Aliphatic/aromatic Amino Acid Pairing for Recognition of the DNA Minor Groove

Selective placement of an aliphatic β-alanine (β) residue paired side-by-side with either a pyrrole (Py) or imidazole (Im) aromatic amino acid is found to compensate for sequence composition effects for recognition of the minor groove of DNA by hairpin pyrrole-imidazole polyamides. A series of polyamides were prepared which contain pyrrole and imidazole aromatic amino acids, as well as γ-aminobutyric acid (γ) "turn" and β-alanine "spring" aliphatic amino acid residues. The binding affinities and specificities of these polyamides are regulated by the placement of paired β/β Py/β and Im/β residues. Quantitative footprint titrations demonstrate that replacing two Py/Py pairings in a 12-ring hairpin (6-γ-6) with two Py/β pairings affords 10-fold enhanced affinity and similar sequence specificity for an 8-bp target sequence.

TABLE 25

Equilibrium association constants ($M^{-1}$) for polyamides.[a–c]

| Polyamide | 5'-TGTTAACA-3' | 5'-TGTGAACA-3' | Specificity[d] |
|---|---|---|---|
|  | $2.5 \times 10^9$ | $3.9 \times 10^8$ | 6 |
|  | $1.3 \times 10^9$ | $2.0 \times 10^8$ | 7 |
|  | $1.7 \times 10^{10}$ | $2.7 \times 10^9$ | 6 |
|  | $\mathbf{1.2 \times 10^{11}}$ | $2.2 \times 10^9$ | 55 |
|  | $6.6 \times 10^9$ | $2.5 \times 10^8$ | 26 |
|  | $4.5 \times 10^{10}$ | $7.7 \times 10^9$ | 6 |

TABLE 25-continued

Equilibrium association constants (M$^{-1}$) for polyamides.[a-c]

| Polyamide | 5'-TGTTAACA-3' | 5'-TGTGAACA-3' | Specificity[d] |
|---|---|---|---|
| (structure) | 2.7 × 10$^{10}$ | 5.7 × 10$^9$ | 5 |
| (structure) | ≤1 × 10$^8$ | ≤1 × 10$^8$ | 1 |

[a]Values reported are the mean values obtained from three DNase I footprint titration experiments.
[b]The assays were carried out at 22° C. at pH 7.0 in the presence of 10 mM Tris-HCl, 10 mM KCl, 10 mM MgCl$_2$, and 5 mM CaCl$_2$.
[c]Match site association constants and specificities higher than the parent hairpin are shown in boldtype.
[d]Specificity is calculated as K$_a$(match)/K$_a$(mismatch).

The 6-γ-6 hairpin ImPyImPyPyPy-γ-ImPyPyPyPyPy-β-Dp, which contains six consecutive amino acid pairings, is unable to discriminate a single-base-pair mismatch site 5'-TGTTAACA-3' from a 5'-TGTGAACA-3' match site. The hairpin polyamide Im-β-ImPyPyPy-γ-ImPyPyPy-β-Py-β-Dp binds to the 8-bp match sequence 5'-TGTGAACA-3' with an equilibrium association constant of K$_a$=2.4×10$^{10}$ M$^{-1}$ and >48-fold specificity versus the 5'-TGTTAACA-3' single-base-pair mismatch site.

TABLE 26

Equilibrium association constants (M$^{-1}$) for polyamides.[a-c]

| Polyamide | 5'-TGTTAACA-3' | 5'-TGTGAACA-3' | Specificity[d] |
|---|---|---|---|
| (structure) | 2.5 × 10$^9$ | 3.9 × 10$^8$ | 6 |
| (structure) | 6.6 × 10$^9$ | 2.5 × 10$^8$ | 26 |
| (structure) | 5 × 10$^9$ | 5 × 10$^9$ | 1 |
| (structure) | ≤5 × 10$^8$ | 2.4 × 10$^{10}$ | ≥48 |

[a]Values reported for 1, 5, and 10 are the mean values obtained from three DNase I footprint titration experiments.
[b]The assays were carried out at 22° C. at pH 7.0 in the presence of 10 mM Tris-HCl, 10 mM KCl, 10 mM MgCl$_2$, and 5 mM CaCl$_2$.
[c]Match site association constants and specificities higher than parent hairpins are shown in boldtype.
[d]Specificity is calculated as K$_a$(match)/K$_a$(mismatch).

Modeling indicates that the β-alanine residue relaxes ligand curvature, providing for optimal hydrogen bond formation between the floor of the minor groove and both Im-residues within the Im-β-Im polyamide subunit. This observation provided the basis for design of a hairpin polyamide, Im-β-ImPy-Im-γ-ImPy-β-Dp, which incorporates Im/β pairings to recognize a "problematic" 5'-GCGC-3' sequence at subnanomolar concentrations.

TABLE 27

Equilibrium association constants ($M^{-1}$) for polyamides.[a-b]

| Polyamide | 5'-TGCGCA-3' | 5'-TGGCCA-3' | 5'-TGGGGA-3' |
|---|---|---|---|
| (structure 1) | $3.7 \times 10^7$ | $<10^7$ | $<10^7$ |
| (structure 2) | $3.7 \times 10^9$ | $1.4 \times 10^8$ | $1.1 \times 10^8$ |

[a]Values reported are the mean values obtained from a minimum of three DNase I footprint titration experiments.
[b]The assays were carried out at 22° C. at pH 7.0 in the presence of 10 mM Tris-HCl, 10 mM KCl, 10 mM $MgCl_2$, and 5 mM $CaCl_2$.

These results identify Im/β and β/Im pairings that respectively discriminate G·C and C·G from A·T/T·A as well as Py/β and β/Py pairings that discriminate A·T/T·A from G·C/C·G. These aliphatic/aromatic amino acid pairings will facilitate the design of hairpin polyamides which recognize both a larger binding site size as well as a more diverse sequence repertoire.

EXAMPLE 10

Polyamide Biotin Conjugates

Bifunctional conjugates prepared between sequence specific DNA binding polyamides and biotin are useful for a variety of applications. First, such compounds can be readily attached to a variety of matrices through the strong interaction of biotin with the protein streptavidin. Readily available strepdavidin-derivatized matrices include magnetic beads for separations as well as resins for chromatography.

A number of such polyamide-biotin conjugates have been synthesized by solid phase synthetic methods outlined in detail above. Following resin cleavage with a variety of diamines, the polyamides were reacted with various biotin carboxylic acid derivatives to yield bifunctional conjugates. The bifunctional conjugates were purified by HPLC and characterized by MALDI-TOF mass spectroscopy and $^1$H NMR.

The scheme for the synthesis of an exemplary biotin-polyamide conjugate is shown below.

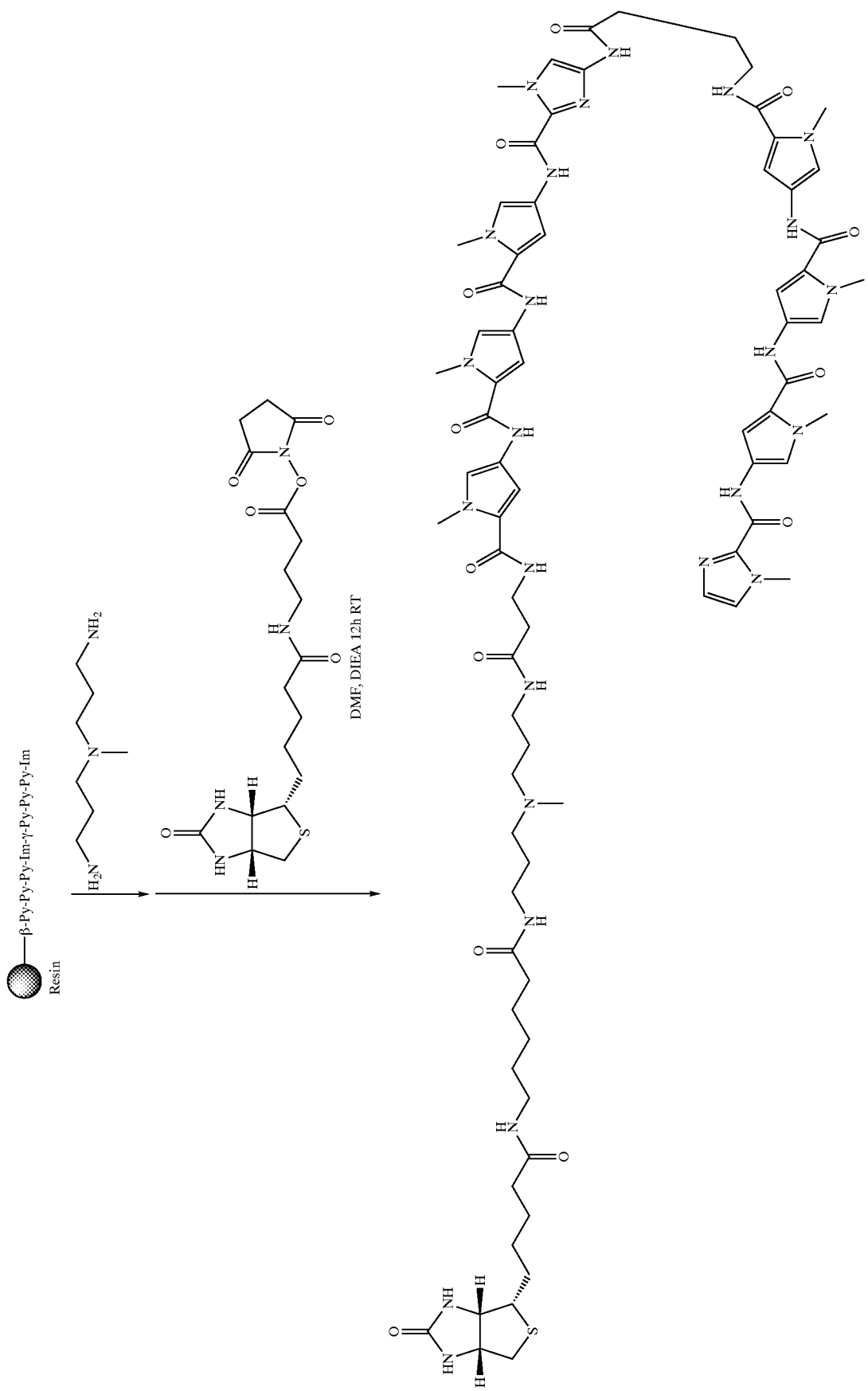

The foregoing is intended to be illustrative of the present invention, but not limiting. Numerous variations and modifications of the present invention may be effected without departing from the true spirit and scope of the invention.

What is claimed is:

1. A polyamide comprising:
at least three consecutive carboxamide pairs that bind in a sequence-specific manner to an equal number of consecutive DNA base pairs in a duplex DNA sequence, at least one of which consecutive DNA base pairs is an A·T or T·A DNA base pair, wherein said polyamide comprises a 3-hydroxy-N-methylpyrrole ("Hp")/N-methylpyrrole ("Py") carboxamide pair to bind to each T·A base pair in said consecutive DNA base pairs and a Py/Hp carboxamide pair to bind to each A·T DNA base pair in said consecutive DNA base pairs.

2. The polyamide of claim 1 wherein at least four consecutive carboxamide pairs bind to at least four DNA base pairs.

3. The polyamide of claim 1 wherein at least five consecutive carboxamide pairs bind to at least five DNA base pairs.

4. The polyamide of claim 1 wherein at least six consecutive carboxamide pairs bind to at least six DNA base pairs.

5. The polyamide of claim 1 wherein the A·T or T·A base pair has a G·C or C·G base pair on either side.

6. The polyamide of claim 1 wherein the duplex DNA sequence is a regulatory sequence.

7. The polyamide of claim 1 wherein the duplex DNA sequence is a promoter sequence.

8. The polyamide of claim 1 wherein the duplex DNA sequence is a coding sequence.

9. The polyamide of claim 1 wherein the duplex DNA sequence is a non-coding sequence.

10. The polyamide of claim 1 wherein the binding of the carboxamide pairs to the DNA base pairs modulates the expression of a gene.

11. A composition comprising an effective amount of the polyamide of claim 1 and a pharmologically suitable excipient.

12. A diagnostic kit comprising the polyamide of claim 1.

13. A polyamide according to claim 1 having the formula:

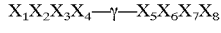

wherein γ is —NH—CH$_2$—CH$_2$—CH$_2$—CONH— or —NH—CH$_2$—CH$_2$—CH(NH$_2$)—CONH—; and X$_4$/X$_5$, X$_3$/X$_6$, X$_2$/X$_7$, and X$_1$/X$_8$ represent carboxamide binding pairs selected from the group consisting of Hp/Py, Py/HP, N-methylimidazole ("Im")/Py, Py/Im, Im/β-alanine, β-alanine/Im, Py/β-alanine, β-alanine/Py, and β-alanine/β-alanine.

14. The polyamide of claim 13 comprising at least one β-alanine.

15. The polyamide of claim 13 wherein dimethylaminopropylamide is covalently bound to X$_1$ or X$_8$.

16. A polyamide according to claim 13 selected from the group consisting of ImHpHpHp-γ-PyPyPyPy, ImHpHpPy-γ-HpPyPyPy, ImHpHpIm-γ-PyPyPyPy, ImHpHpPy-γ-ImPyPyPy, ImHpPyHp-γ-PyHpPyPy, ImHpPyPy-γ-HpHpPyPy, ImHpPyIm-γ-PyHpPyPy, ImHpPyPy-γ-ImHpPyPy, ImHpImHp-γ-PyPyPyPy, ImHpImPy-γ-HpPyPyPy, ImHpImIm-γ-PyPyPyPy, ImHpImPy-γ-ImPyPyPy, ImHpPyHp-γ-PyImPyPy, ImHpPyPy-γ-HpImPyPy, ImHpPyIm-γ-PyImPyPy, ImHpPyPy-γ-ImImPyPy, ImImPyPy, ImPyHpHp-γ-PyPyHpPy, ImPyHpPy-γ-HpPyHpPy, ImPyHpPy-γ-ImPyHpPy, ImPyHpIm-γ-PyPyHpPy, ImPyHpPy-γ-
ImPyHpPy, ImPyPyHp-γ-PyHpHpPy, ImPyPyPy-γ-HpHpHpPy, ImPyPyIm-γ-PyHpHpPy, ImPyPyPy-γ-ImHpHpPy, ImPyImHp-γ-PyPyHpPy, ImPyImPy-γ-HpPyHpPy, ImPyImIm-γ-PyPyHpPy, ImPyImPy-γ-ImPyHpPy, ImPyPyHp-γ-PyImHpPy, ImPyPyPy-γ-HpImHpPy, ImPyPyIm-γ-PyImHpPy, ImPyPyPy-γ-ImImHpPy, ImImHpPy-γ-PyPyPyPy, ImImHpIm-γ-PyPyPyPy, ImImHpPy-γ-ImPyPyPy, ImImPyHp-γ-PyHpPyPy, ImImPyPy-γ-HpHpPyPy, ImImPyIm-γ-PyHpPyPy, ImImPyPy-γ-ImHpPyPy, ImImImHp-γ-PyPyPyPy, ImImPyHp-γ-PyImPyPy, ImImPyPy-γ-HpImPyPy, ImImPyIm-γ-PyImPyPy, ImImPyPy-γ-ImImPyPy, ImPyHpHp-γ-PyPyImPy, ImPyHpPy-γ-HpPyImPy, ImPyHpIm-γ-PyPyImPy, ImPyHpPy-γ-ImPyImPy, ImPyPyPy-γ-HpHpImPy, ImPyPyIm-γ-PyHpImPy, ImPyPyPy-γ-ImHpImPy, ImPyImHp-γ-PyPyImPy, ImPyImPy-γ-HpPyImPy, ImPyImIm-γ-PyPyImPy, ImPyImPy-γ-ImPyImPy, ImPyPyPy-γ-ImImImPy, HpHpHpHp-γ-PyPyPyPy, HpHpHpPy-γ-HpPyPyPy, HpHpHpIm-γ-PyPyPyPy, HpHpHpPy-γ-ImPyPyPy, HpHpPyHp-γ-PyHpPyPy, HpHpPyPy-γ-HpHpPyPy, HpHpPyIm-γ-PyHpPyPy, HpHpPyPy-γ-ImHpPyPy, HpHpImHp-γ-PyPyPyPy, HpHpImPy-γ-HpPyPyPy, HpHpImIm-γ-PyPyPyPy, HpHpPyHp-γ-PyImPyPy, HpHpPyPy-γ-HpImPyPy, HpHpPyIm-γ-PyImPyPy, HpHpPyPy-γ-ImImPyPy, HpPyHpHp-γ-PyPyHpPy, HpPyHpPy-γ-HpPyHpPy, HpPyHpIm-γ-PyPyHpPy, HpPyHpPy-γ-ImPyHpPy, HpPyPyHp-γ-PyHpHpPy, HpPyPyPy-γ-HpHpHpPy, HpPyPyIm-γ-PyHpHpPy, HpPyPyPy-γ-ImHpHpPy, HpPyImHp-γ-PyPyHpPy, HpPyImPy-γ-HpPyHpPy, HpPyImIm-γ-PyPyHpPy, HpPyImPy-γ-ImPyHpPy, HpPyPyHp-γ-PyImHpPy, HpPyPyPy-γ-HpImHpPy, HpPyPyIm-γ-PyImHpPy, HpPyPyPy-γ-ImImHpPy, HpImHpHp-γ-PyPyPyPy, HpImHpPy-γ-HpPyPyPy, HpImHpIm-γ-PyPyPyPy, HpImHpPy-γ-ImPyPyPy, HpImPyHp-γ-PyHpPyPy, HpImPyPy-γ-HpHpPyPy, HpImPyIm-γ-PyHpPyPy, HpImPyPy-γ-ImHpPyPy, HpImImHp-γ-PyPyPyPy, HpImImPy-γ-HpPyPyPy, HpImImIm-γ-PyPyPyPy, HpImPyHp-γ-PyImPyPy, HpImPyPy-γ-HpImPyPy, HpImPyIm-γ-PyImPyPy, HpPyHpHp-γ-PyPyImPy, HpPyHpPy-γ-HpPyImPy, HpPyHpIm-γ-PyPyImPy, HpPyHpPy-γ-ImPyImPy, HpPyPyHp-γ-PyHpImPy, HpPyPyPy-γ-HpHpImPy, HpPyPyIm-γ-PyHpImPy, HpPyPyPy-γ-ImHpImPy, HpPyImHp-γ-PyPyImPy, HpPyImPy-γ-HpPyImPy, HpPyImIm-γ-PyPyImPy, HpPyImPy-γ-ImPyImPy, HpPyPyHp-γ-PyImImPy, HpPyPyPy-γ-HpImImPy, HpPyPyIm-γ-PyImImPy, HpPyPyPy-γ-ImImImPy, PyHpHpHp-γ-HpPyPyHp, PyHpHpIm-γ-PyPyPyHp, PyHpHpPy-γ-ImPyPyHp, PyHpPyHp-γ-HpHpPyHp, PyHpPyIm-γ-PyHpPyHp, PyHpPyPy-γ-ImHpPyHp, PyHpImHp-γ-HpPyPyHp, PyHpImPy-γ-PyPyPyHp, PyHpImIm-γ-PyPyPyHp, PyHpImPy-γ-ImPyPyHp, PyHpPyHp-γ-HpImPyHp, PyHpPyIm-γ-PyImPyHp, PyHpPyPy-γ-ImImPyHp, PyPyHpHp-γ-HpPyHpHp, PyPyHpIm-γ-PyPyHpHp, PyPyHpPy-γ-ImPyHpHp, PyPyPyHp-γ-HpHpHpHp, PyPyPyIm-γ-PyHpHpHp, PyPyPyPy-γ-ImHpHpHp, PyPyImHp-γ-HpPyHpHp, PyPyImPy-γ-PyPyHpHp, PyPyImIm-γ-PyPyHpHp, PyPyImPy-γ-ImPyHpHp, PyPyPyHp-γ-HpImHpHp, PyPyPyIm-γ-PyImHpHp, PyPyPyPy-γ-HpPyHpHp, PyPyImIm-γ-

PyPyHpHp, PyPyImPy-γ-ImPyHpHp, PyPyPyHp-γ-PyImHpHp, PyPyPyPy-γ-HpImHpHp, PyPyPyIm-γ-PyImHpHp, PyPyPyPy-γ-ImImHpHp, PyImHpHp-γ-PyPyPyHp, PyImHpPy-γ-HpPyPyHp, PyImHpIm-γ-PyPyPyHp, PyImHpPy-γ-ImPyPyHp, PyImPyHp-γ-PyHpPyHp, PyImPyPy-γ-HpHpPyHp, PyImPyIm-γ-PyHpPyHp, PyImPyPy-γ-ImHpPyHp, PyImImHp-γ-PyPyPyHp, PyImImPy-γ-HpPyPyHp, PyImPyHp-γ-PyImPyHp, PyImPyPy-γ-HpImPyHp, PyImImIm-γ-PyPyPyHp, PyImImPy-γ-ImPyPyHp, PyImPyIm-γ-PyImPyHp, PyImPyPy-γ-ImImPyHp, PyPyHpHp-γ-PyPyImHp, PyPyHpPy-γ-HpPyImHp, PyPyHpIm-γ-PyPyImHp, PyPyHpPy-γ-ImPyImHp, PyPyPyHp-γ-PyHpImHp, PyPyPyPy-γ-HpHpImHp, PyPyPyIm-γ-PyHpImHp, PyPyPyPy-γ-ImHpImHp, PyPyImHp-γ-PyPyImHp, PyPyImPy-γ-HpPyImHp, PyPyPyHp-γ-PyImImHp, PyPyPyPy-γ-HpImImHp, PyPyImIm-γ-PyPyImHp, PyPyImPy-γ-ImPyImHp, PyPyPyIm-γ-PyImImHp, PyPyPyPy-γ-ImImImHp, PyHpHpHp-γ-PyPyPyIm, PyHpHpPy-γ-HpPyPyIm, PyHpHpIm-γ-PyPyPyIm, PyHpHpPy-γ-ImPyPyIm, PyHpPyHp-γ-PyHpPyIm, PyHpPyPy-γ-HpHpPyIm, PyHpPyIm-γ-PyHpPyIm, PyHpPyPy-γ-ImHpPyIm, PyHpImHp-γ-PyPyPyIm, PyHpImPy-γ-HpPyPyIm, PyHpImIm-γ-PyPyPyIm, PyHpImPy-γ-ImPyPyIm, PyHpPyHp-γ-PyImPyIm, PyHpPyPy-γ-HpImPyIm, PyHpPyIm-γ-PyImPyIm, PyHpPyPy-γ-ImImPyIm, PyPyHpHp-γ-PyPyHpIm, PyPyHpPy-γ-HpPyHpIm, PyPyHpIm-γ-PyPyHpIm, PyPyHpPy-γ-ImPyHpIm, PyPyPyHp-γ-PyHpHpIm, PyPyPyPy-γ-HpHpHpIm, PyPyPyIm-γ-PyHpHpIm, PyPyPyPy-γ-ImHpHpIm, PyPyImHp-γ-PyPyHpIm, PyPyImPy-γ-HpPyHpIm, PyPyImIm-γ-PyPyHpIm, PyPyImPy-γ-ImPyHpIm, PyPyPyHp-γ-PyImHpIm, PyPyPyPy-γ-HpImHpIm, PyPyPyIm-γ-PyImHpIm, PyPyPyPy-γ-ImImHpIm, PyImHpHp-γ-PyPyPyIm, PyImHpPy-γ-HpPyPyIm, PyImImIm-γ-PyPyPyIm, PyImHpPy-γ-ImPyPyIm, PyImPyHp-γ-PyHpPyIm, PyImPyPy-γ-HpHpPyIm, PyImPyIm-γ-PyHpPyIm, PyImPyPy-γ-ImHpPyIm, PyImImHp-γ-PyPyPyIm, PyImImPy-γ-HpPyPyIm, PyImPyHp-γ-PyImPyIm, PyImPyPy-γ-HpImPyIm, PyImImIm-γ-PyPyPyIm, PyImImPy-γ-ImPyPyIm, PyImPyIm-γ-PyImPyIm, PyImPyPy-γ-ImImPyIm, PyPyHpHp-γ-PyPyImIm, PyPyHpPy-γ-HpPyImIm, PyPyHpIm-γ-PyPyImIm, PyPyHpPy-γ-ImPyImIm, PyPyPyHp-γ-PyHpImIm, PyPyPyPy-γ-HpHpImIm, PyPyPyIm-γ-PyHpImIm, PyPyPyPy-γ-ImHpImIm, PyPyImHp-γ-PyPyImIm, PyPyImPy-γ-HpPyImIm, PyPyPyHp-γ-PyImImIm, PyPyPyPy-γ-HpImImIm, PyPyImIm-γ-PyPyImIm, PyPyImPy-γ-ImPyImIm, PyPyPyIm-γ-PyImImIm, and PyPyPyPy-γ-ImImImIm.

17. A polyamide according to claim 1 selected from the group consisting of ImPyPy-γ-HpPyPy-(β-alanine)-dimethylaminopropylamide, ImPyHp-γ-PyPyPy-(β-alanine)-dimethylaminopropylamide, ImHpPy-γ-PyPyPy-(β-alanine)-dimethylaminopropylamide, ImPyPyPy-γ-PyHpPy-(β-alanine)-dimethylaminopropylamide, ImImHpPy-γ-ImImPyPy-(β-alanine)-dimethylaminopropylamide, ImImPyPy-γ-ImHpPyPy-(β-alanine)-dimethylaminopropylamide, ImHpPyPy-γ-ImHpPyPy-(β-alanine)-dimethylaminopropylamide, ImHpPyPyPy-γ-ImHpPyPyPy-(β-alanine)-dimethylaminopropylamide, ImImPyPyPy-γ-ImHpHpPyPy-(β-alanine)-dimethylaminopropylamide, wherein γ is —NH—$CH_2$—$CH_2$—$CH_2$—CONH—.

* * * * *

UNITED STATES PATENT AND TRADEMARK OFFICE
CERTIFICATE OF CORRECTION

PATENT NO.   : 6,472,537 B1
DATED        : October 29, 2002
INVENTOR(S)  : Eldon E. Baird and Peter B Dervan It is certified that error appears in the above-identified patent and that said Letters Patent is hereby corrected as shown below:

Column 46,
Line 10, after "ImImPyIm-γ-PyHpPyPy" insert -- ImImPyPy-γ-ImHpPyPy --

Column 48,
Line 2, delete "PyImImIm-γ-" and substitute -- PyImHpIm-γ- --

Signed and Sealed this

Eighteenth Day of March, 2003

JAMES E. ROGAN
*Director of the United States Patent and Trademark Office*